(12) United States Patent
Weyer et al.

(10) Patent No.: US 7,879,794 B2
(45) Date of Patent: Feb. 1, 2011

(54) METHODS FOR CONTROLLING BINGE EATING DISORDERS

(75) Inventors: Christian Weyer, San Diego, CA (US); Kevin D. Laugero, Davis, CA (US); Christine M. Mack, San Diego, CA (US); David G. Parkes, Del Mar, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 117 days.

(21) Appl. No.: 11/910,214

(22) PCT Filed: Mar. 31, 2006

(86) PCT No.: PCT/US2006/011768

§ 371 (c)(1),
(2), (4) Date: May 29, 2008

(87) PCT Pub. No.: WO2006/105345

PCT Pub. Date: Oct. 5, 2006

(65) Prior Publication Data

US 2009/0062193 A1 Mar. 5, 2009

Related U.S. Application Data

(60) Provisional application No. 60/667,335, filed on Mar. 31, 2005, provisional application No. 60/666,681, filed on Mar. 31, 2005, provisional application No. 60/675,441, filed on Apr. 28, 2005, provisional application No. 60/760,583, filed on Jan. 20, 2006.

(51) Int. Cl.
*A61K 38/00* (2006.01)
(52) U.S. Cl. .................................. 514/1.1; 530/325
(58) Field of Classification Search ........................ None
See application file for complete search history.

(56) References Cited

U.S. PATENT DOCUMENTS

| 5,175,145 | A | 12/1992 | Cooper |
| 5,234,906 | A | 8/1993 | Young |
| 5,405,831 | A | 4/1995 | MacIntyre |
| 5,677,279 | A | 10/1997 | Young |
| 6,114,304 | A | 9/2000 | Kolterman |
| 7,101,853 | B2 | 9/2006 | Young |
| 2003/0130177 | A1 | 7/2003 | Kolterman |
| 2004/0022807 | A1 | 2/2004 | Duft |
| 2005/0197287 | A1 | 9/2005 | Mack |

FOREIGN PATENT DOCUMENTS

| WO | WO2006/105527 | 8/2006 |
| WO | WO2006/083254 | 10/2006 |

OTHER PUBLICATIONS

Dingemans et al., Int. J. Obesity 26: 299-307, 2002.*
Reda et al., Obesity Res. 10: 1087-1091, 2002.*
Halford, Jason, et al. "The Psychopharmacology of Appetite: Targets . . . " (2003) Current Medicinal Chemistry CNS Agents vol. 3, N4.4.: 283-310.
Morley, J.E. et al., "Effects of Amylin on Appetite Regulation and Memory", (1995) Candian Journ. of Physiol. and Pharma., Ottawa Ont. CA vol. 73:1042-1046.
Ratner, Robert E. et al., "Adjunctive Therapy with the Amylin Analogue . . . " (2002) Diabetes Tech & Thera. vol. 4 #1 pp. 51-61.
Roh, et al., "Intermedin Is a Calcitonin/Calcitonin Gene-related Peptide Family" (2004) J. Biol. Chem. 279:726-7274.
Rushing, P.A., et al., Program No. 309.11, 2001 Neuroscience Meeting Planner, San Diego, CA: Society for Neuroscience, 2001. Online: *Enhanced Effect of Adiposity Signals in Dopamine-3 Receptor Knockout Mice.*
U.S. Appl. No. 60/543,275, Soares [Amylin Pharmaceuticals].
Fairburn & Wilson, *Binge Eating: Nature, Assessment and Treatment*, Chapter 1, Binge Eating: Definition and Classification, Fairbum & Cooper, Eds., NY (1993).
Stunkard, *Psychiatric Quarterly* 33:284-295 (1959) "Eating Patterns and Obesity".
Stunkard, *Binge Eating: Nature, Assessment and Treatment*, Chapter 2, Fairburn & Cooper, Eds., NY (1993) "A History of Binge Eating".
Telch and Agras, *Intl J. Eating Disorders* 15:53-61 (1994) "Obesity, Binge Eating and Psychopathology: Are They Related?".

\* cited by examiner

*Primary Examiner*—Robert Landsman
*Assistant Examiner*—Gyan Chandra

(57) ABSTRACT

Compositions and methods for preventing, treating or controlling conditions or disorders associated with obesity, diet, and nutrition are provided. The methods provided generally involve the administration of an amylin or an amylin agonist to a subject in order to prevent, treat or controlling conditions or disorders associated with obesity, diet, and nutrition.

20 Claims, 15 Drawing Sheets

SEQUENCE LISTING

<160> NUMBER OF SEQ ID NOS: 253

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Rattus norvegicus

<400> SEQUENCE: 2

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: residues 2 and 7 are independently selected
      amino acid residues having side chains which are chemically bonded
      to each other to form an intramolecular linkage
<220> FEATURE:
<221> NAME/KEY: MISC_FEATURE
<222> LOCATION: (1)..(1)
<223> OTHER INFORMATION: Lys, Ala, Ser, or hydrogen
<220> FEATURE:
<221> NAME/KEY: MISC_FEATURE
<222> LOCATION: (2)..(2)
<223> OTHER INFORMATION: variable amino acid
<220> FEATURE:
<221> NAME/KEY: MISC_FEATURE
<222> LOCATION: (7)..(7)
<223> OTHER INFORMATION: variable amino acid
<220> FEATURE:
<221> NAME/KEY: MISC_FEATURE
<222> LOCATION: (13)..(13)
<223> OTHER INFORMATION: Ala, Ser or Thr
<220> FEATURE:
<221> NAME/KEY: MISC_FEATURE
<222> LOCATION: (17)..(17)
<223> OTHER INFORMATION: Val, Leu or Ile
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
<220> FEATURE:

```
<221> NAME/KEY: MISC_FEATURE
<222> LOCATION: (20)..(20)
<223> OTHER INFORMATION: Ser, Thr, Gln or Asn
<220> FEATURE:
<221> NAME/KEY: MISC_FEATURE
<222> LOCATION: (21)..(21)
<223> OTHER INFORMATION: Asn, Gln or His
<220> FEATURE:
<221> NAME/KEY: MISC_FEATURE
<222> LOCATION: (23)..(23)
<223> OTHER INFORMATION: Phe, Leu or Tyr
<220> FEATURE:
<221> NAME/KEY: MISC_FEATURE
<222> LOCATION: (25)..(25)
<223> OTHER INFORMATION: Ala or Pro
<220> FEATURE:
<221> NAME/KEY: MISC_FEATURE
<222> LOCATION: (26)..(26)
<223> OTHER INFORMATION: Ile, Val, Ala or Leu
<220> FEATURE:
<221> NAME/KEY: MISC_FEATURE
<222> LOCATION: (28)..(28)
<223> OTHER INFORMATION: Ser, Pro, Leu, Ile or Thr
<220> FEATURE:
<221> NAME/KEY: MISC_FEATURE
<222> LOCATION: (29)..(29)
<223> OTHER INFORMATION: Ser, Pro or Thr
<220> FEATURE:
<221> NAME/KEY: MISC_FEATURE
<222> LOCATION: (31)..(31)
<223> OTHER INFORMATION: Asn, Asp, or Gln

<400> SEQUENCE: 3

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
                20                  25                  30

Gly Ser Asn Thr Tyr
        35

<210> SEQ ID NO 4
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 4

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
                20                  25                  30

Ser Asn Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
                20                  25                  30

Gly Ser Asn Thr Tyr
```

```
<210> SEQ ID NO 6
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 6
```

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

```
<210> SEQ ID NO 7
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 7
```

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

```
<210> SEQ ID NO 8
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 8
```

Cys Asn Thr Ala Thr Cys Ala Thr Gln Arg Leu Ala Asn Phe Leu Val
1               5                   10                  15

His Arg Ser Asn Asn Phe Gly Pro Ile Leu Pro Ser Thr Asn Val Gly
            20                  25                  30

Ser Asn Thr Tyr
        35

```
<210> SEQ ID NO 9
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 9
```

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

```
<210> SEQ ID NO 10
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 10

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 11
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 11

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Ser Asn Val Gly
            20                  25                  30

Ser Asn Thr Tyr
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 12

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Ser Asn Val Gly
            20                  25                  30

Ser Asn Thr Tyr
        35

<210> SEQ ID NO 13
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 13

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 14
<211> LENGTH: 37
<212> TYPE: PRT
```

<213> ORGANISM: Artificial Sequence
<220> FEATURE:
<223> OTHER INFORMATION: Synthetic peptide construct

<400> SEQUENCE: 14

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
        35

<210> SEQ ID NO 15
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 15

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 16
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 16

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 17

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 18

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 19

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 20

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 21

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35

<210> SEQ ID NO 22
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 22

```
Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 23
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 23

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
            35

<210> SEQ ID NO 24
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 24

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
            35

<210> SEQ ID NO 25
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 25

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
            35

<210> SEQ ID NO 26
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 26

Lys Cys Asn Thr Ala Thr Cys Ala Thr Gln Arg Leu Thr Asn Phe Leu
1               5                   10                  15
```

```
Val His Ser Ser His Asn Leu Gly Ala Ala Leu Leu Pro Thr Asp Val
            20                  25                  30

Gly Ser Asn Thr Tyr
        35

<210> SEQ ID NO 27
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 27

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

<210> SEQ ID NO 28
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 28

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

<210> SEQ ID NO 29
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 29

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 30
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 30

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30
```

```
<210> SEQ ID NO 31
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 31

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 32
<211> LENGTH: 47
<212> TYPE: PRT
<213> ORGANISM: Homo sapiens

<400> SEQUENCE: 32

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 33
<211> LENGTH: 40
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: absent, SEQ ID NO:34, any of one or more
      consecutive amino acids of SEQ ID NO:34, N-aryl, or N-acyl with a
      substituent selected from a C1-C18 alkyl, a substituted alkyl or a
      heteroaryl moiety
<220> FEATURE:
<221> NAME/KEY: MISC_FEATURE
<222> LOCATION: (2)..(2)
<223> OTHER INFORMATION: M, S, C, substituted L, K, D, or E, where the
      side chain can be linked via an amide bond, or any amino acid that
      can form a bond with X at position 8
<220> FEATURE:
<221> NAME/KEY: MISC_FEATURE
<222> LOCATION: (3)..(3)
<223> OTHER INFORMATION: V, D, L, G, N, A, or S
<220> FEATURE:
<221> NAME/KEY: MISC_FEATURE
<222> LOCATION: (4)..(4)
<223> OTHER INFORMATION: V, D, L, G, N, A, S or T
<220> FEATURE:
<221> NAME/KEY: MISC_FEATURE
<222> LOCATION: (5)..(5)
<223> OTHER INFORMATION: V, D, L, G, N, A, or S
<220> FEATURE:
<221> NAME/KEY: MISC_FEATURE
<222> LOCATION: (6)..(6)
<223> OTHER INFORMATION: V, D, L, G, N, A, S, or absent
<220> FEATURE:
<221> NAME/KEY: MISC_FEATURE
<222> LOCATION: (7)..(7)
<223> OTHER INFORMATION: T, S, Hse, Ahb or Ahp
```

```
<220> FEATURE:
<221> NAME/KEY: MISC_FEATURE
<222> LOCATION: (8)..(8)
<223> OTHER INFORMATION: M, S, C, substituted L, K, D, or E, or any
      amino acid that can form a bond with X at position 2
<220> FEATURE:
<221> NAME/KEY: MISC_FEATURE
<222> LOCATION: (21)..(21)
<223> OTHER INFORMATION: M, G, P, A, or absent
<220> FEATURE:
<221> NAME/KEY: MISC_FEATURE
<222> LOCATION: (22)..(22)
<223> OTHER INFORMATION: M, G, P, A, or absent
<220> FEATURE:
<221> NAME/KEY: MISC_FEATURE
<222> LOCATION: (23)..(23)
<223> OTHER INFORMATION: M, G, P, A, or absent
<220> FEATURE:
<221> NAME/KEY: MISC_FEATURE
<222> LOCATION: (24)..(24)
<223> OTHER INFORMATION: M, G, P, A, or absent
<220> FEATURE:
<221> NAME/KEY: MISC_FEATURE
<222> LOCATION: (25)..(25)
<223> OTHER INFORMATION: M, G, P, A, or absent
<220> FEATURE:
<221> NAME/KEY: MISC_FEATURE
<222> LOCATION: (26)..(26)
<223> OTHER INFORMATION: R or absent; when absent, X at position 27 is
      absent
<220> FEATURE:
<221> NAME/KEY: MISC_FEATURE
<222> LOCATION: (27)..(27)
<223> OTHER INFORMATION: Q or absent; when absent, X at position 26 is
      absent
<220> FEATURE:
<221> NAME/KEY: MISC_FEATURE
<222> LOCATION: (28)..(28)
<223> OTHER INFORMATION: D or E
<220> FEATURE:
<221> NAME/KEY: MISC_FEATURE
<222> LOCATION: (33)..(33)
<223> OTHER INFORMATION: D or E

<400> SEQUENCE: 33

Xaa Xaa Xaa Xaa Xaa Xaa Xaa Xaa Gln Val Gln Asn Leu Ser His Arg
1               5                   10                  15

Leu Trp Gln Leu Xaa Xaa Xaa Xaa Xaa Xaa Xaa Xaa Ser Ala Pro Val
                20                  25                  30

Xaa Pro Ser Ser Pro His Ser Tyr
            35                  40

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide construct

<400> SEQUENCE: 34

Thr Gln Ala Gln Leu Leu Arg Val Gly
1               5

<210> SEQ ID NO 35
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Q or absent
```

```
<220> FEATURE:
<221> NAME/KEY: MISC_FEATURE
<222> LOCATION: (2)..(2)
<223> OTHER INFORMATION: V or absent
<220> FEATURE:
<221> NAME/KEY: MISC_FEATURE
<222> LOCATION: (13)..(13)
<223> OTHER INFORMATION: M, G, P, A, or absent
<220> FEATURE:
<221> NAME/KEY: MISC_FEATURE
<222> LOCATION: (14)..(14)
<223> OTHER INFORMATION: M, G, P, A, or absent
<220> FEATURE:
<221> NAME/KEY: MISC_FEATURE
<222> LOCATION: (15)..(15)
<223> OTHER INFORMATION: M, G, P, A, or absent
<220> FEATURE:
<221> NAME/KEY: MISC_FEATURE
<222> LOCATION: (16)..(16)
<223> OTHER INFORMATION: M, G, P, A, or absent
<220> FEATURE:
<221> NAME/KEY: MISC_FEATURE
<222> LOCATION: (17)..(17)
<223> OTHER INFORMATION: M, G, P, A, or absent
<220> FEATURE:
<221> NAME/KEY: MISC_FEATURE
<222> LOCATION: (18)..(18)
<223> OTHER INFORMATION: R or absent; when absent, X at position 19 is
      absent
<220> FEATURE:
<221> NAME/KEY: MISC_FEATURE
<222> LOCATION: (19)..(19)
<223> OTHER INFORMATION: Q or absent; when absent, X at position 18 is
      absent
<220> FEATURE:
<221> NAME/KEY: MISC_FEATURE
<222> LOCATION: (20)..(20)
<223> OTHER INFORMATION: D or E
<220> FEATURE:
<221> NAME/KEY: MISC_FEATURE
<222> LOCATION: (25)..(25)
<223> OTHER INFORMATION: D or E

<400> SEQUENCE: 35

Xaa Xaa Gln Asn Leu Ser His Arg Leu Trp Gln Leu Xaa Xaa Xaa Xaa
1               5                   10                  15

Xaa Xaa Xaa Xaa Ser Ala Pro Val Xaa Pro Ser Ser Pro His Ser Tyr
            20                  25                  30

<210> SEQ ID NO 36
<211> LENGTH: 41
<212> TYPE: PRT
<213> ORGANISM: Artificial Sequence
<220> FEATURE:
<223> OTHER INFORMATION: Synthetic peptide construct

<400> SEQUENCE: 36

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr
        35                  40

<210> SEQ ID NO 37
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 37
```

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
            35

<210> SEQ ID NO 38
<211> LENGTH: 38
<212> TYPE: PRT
<213> ORGANISM: Artificial Sequence
<220> FEATURE:
<223> OTHER INFORMATION: Synthetic peptide construct

<400> SEQUENCE: 38

Cys Val Leu Gly Thr Cys Gln Val Gln Asn Leu Ser His Arg Leu Trp
1               5                   10                  15

Gln Leu Met Gly Pro Ala Gly Arg Gln Asp Ser Ala Pro Val Asp Pro
            20                  25                  30

Ser Ser Pro His Ser Tyr
            35

<210> SEQ ID NO 39
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 39

Gln Val Gln Asn Leu Ser His Arg Leu Trp Gln Leu Met Gly Pro Ala
1               5                   10                  15

Gly Arg Gln Asp Ser Ala Pro Val Asp Pro Ser Ser Pro His Ser Tyr
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 40

Val Gln Asn Leu Ser His Arg Leu Trp Gln Leu Met Gly Pro Ala Gly
1               5                   10                  15

Arg Gln Asp Ser Ala Pro Val Asp Pro Ser Ser Pro His Ser Tyr
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 41

Val Gln Asn Leu Ser His Arg Leu Gln Leu Met Gly Pro Ala Gly Arg
1               5                   10                  15

Gln Asp Ser Ala Pro Val Asp Pro Ser Ser Pro His Ser Tyr
            20                  25                  30

<210> SEQ ID NO 42

<211> LENGTH: 42
<212> TYPE: PRT
<213> ORGANISM: Artificial Sequence
<220> FEATURE:
<223> OTHER INFORMATION: Synthetic peptide construct

<400> SEQUENCE: 42

Thr Gln Ala Gln Leu Leu Arg Val Gly Cys Val Leu Gly Thr Cys Gln
1               5                   10                  15
Val Gln Asn Leu Ser His Arg Leu Trp Gln Leu Arg Gln Asp Ser Ala
            20                  25                  30
Pro Val Asp Pro Ser Ser Pro His Ser Tyr
        35                  40

<210> SEQ ID NO 43
<211> LENGTH: 40
<212> TYPE: PRT
<213> ORGANISM: Artificial Sequence
<220> FEATURE:
<223> OTHER INFORMATION: Synthetic peptide construct

<400> SEQUENCE: 43

Thr Gln Ala Gln Leu Leu Arg Val Gly Cys Val Leu Gly Thr Cys Gln
1               5                   10                  15
Val Gln Asn Leu Ser His Arg Leu Trp Gln Leu Asp Ser Ala Pro Val
            20                  25                  30
Asp Pro Ser Ser Pro His Ser Tyr
        35                  40

<210> SEQ ID NO 44
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 44

Val Gly Cys Val Leu Gly Thr Cys Gln Val Gln Asn Leu Ser His Arg
1               5                   10                  15
Leu Trp Gln Leu Arg Gln Asp Ser Ala Pro Val Asp Pro Ser Ser Pro
            20                  25                  30
His Ser Tyr
        35

<210> SEQ ID NO 45
<211> LENGTH: 33
<212> TYPE: PRT
<213> ORGANISM: Artificial Sequence
<220> FEATURE:
<223> OTHER INFORMATION: Synthetic peptide construct

<400> SEQUENCE: 45

Cys Val Leu Gly Thr Cys Gln Val Gln Asn Leu Ser His Arg Leu Trp
1               5                   10                  15
Gln Leu Arg Gln Glu Ser Ala Pro Val Glu Pro Ser Ser Pro His Ser
            20                  25                  30
Tyr

<210> SEQ ID NO 46
<211> LENGTH: 48
<212> TYPE: PRT
<213> ORGANISM: Artificial Sequence
<220> FEATURE:

<223> OTHER INFORMATION: Synthetic peptide construct

<400> SEQUENCE: 46

Thr Gln Ala Gln Leu Leu Arg Val Gly Cys Ser Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45

<210> SEQ ID NO 47
<211> LENGTH: 47
<212> TYPE: PRT
<213> ORGANISM: Artificial Sequence
<220> FEATURE:
<223> OTHER INFORMATION: Synthetic peptide construct

<400> SEQUENCE: 47

Thr Gln Ala Gln Leu Leu Arg Val Gly Cys Asn Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 48
<211> LENGTH: 42
<212> TYPE: PRT
<213> ORGANISM: Artificial Sequence
<220> FEATURE:
<223> OTHER INFORMATION: Synthetic peptide construct

<400> SEQUENCE: 48

Arg Val Gly Cys Gly Asn Leu Ser Thr Cys Gln Val Gln Asn Leu Ser
1               5                   10                  15

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

<210> SEQ ID NO 49
<211> LENGTH: 47
<212> TYPE: PRT
<213> ORGANISM: Artificial Sequence
<220> FEATURE:
<223> OTHER INFORMATION: Synthetic peptide construct

<400> SEQUENCE: 49

Thr Gln Ala Gln Leu Leu Arg Val Gly Cys Asp Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 50
<211> LENGTH: 48
<212> TYPE: PRT
<213> ORGANISM: Artificial Sequence
<220> FEATURE:
<223> OTHER INFORMATION: Synthetic peptide construct

<400> SEQUENCE: 50

```
Thr Gln Ala Gln Leu Leu Arg Val Gly Cys Gly Asn Leu Ser Thr Cys
1               5                   10                  15

Gln Val Gln Asn Leu Ser His Arg Leu Trp Gln Leu Met Gly Pro Ala
                20                  25                  30

Gly Arg Gln Asp Ser Ala Pro Val Asp Pro Ser Ser Pro His Ser Tyr
            35                  40                  45
```

<210> SEQ ID NO 51
<211> LENGTH: 47
<212> TYPE: PRT
<213> ORGANISM: Artificial Sequence
<220> FEATURE:
<223> OTHER INFORMATION: Synthetic peptide construct

<400> SEQUENCE: 51

```
Thr Gln Ala Gln Leu Leu Arg Val Gly Met Val Leu Gly Thr Met Gln
1               5                   10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
            35                  40                  45
```

<210> SEQ ID NO 52
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 52

```
Gly Met Val Leu Gly Thr Met Gln Val Gln Asn Leu Ser His Arg Leu
1               5                   10                  15

Trp Gln Leu Met Gly Pro Ala Gly Arg Gln Asp Ser Ala Pro Val Asp
                20                  25                  30

Pro Ser Ser Pro His Ser Tyr
            35
```

<210> SEQ ID NO 53
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 53

```
Val Gly Met Val Leu Gly Thr Met Gln Val Gln Asn Leu Ser His Arg
1               5                   10                  15

Leu Trp Gln Leu Arg Gln Asp Ser Ala Pro Val Asp Pro Ser Ser Pro
                20                  25                  30

His Ser Tyr
        35
```

<210> SEQ ID NO 54
<211> LENGTH: 42
<212> TYPE: PRT
<213> ORGANISM: Artificial Sequence
<220> FEATURE:
<223> OTHER INFORMATION: Synthetic peptide construct

<400> SEQUENCE: 54

```
Arg Val Gly Cys Gly Asn Leu Ser Thr Cys Gln Val Gln Asn Leu Ser
1               5                   10                  15
```

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

<210> SEQ ID NO 55
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 55

Val Gly Cys Gly Asn Leu Ser Thr Cys Gln Val Gln Asn Leu Ser His
1               5                   10                  15

Arg Leu Trp Gln Leu Arg Gln Asp Ser Ala Pro Val Asp Pro Ser Ser
            20                  25                  30

Pro His Ser Tyr
        35

<210> SEQ ID NO 56
<211> LENGTH: 34
<212> TYPE: PRT
<213> ORGANISM: Artificial Sequence
<220> FEATURE:
<223> OTHER INFORMATION: Synthetic peptide construct

<400> SEQUENCE: 56

Val Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 57
<211> LENGTH: 34
<212> TYPE: PRT
<213> ORGANISM: Artificial Sequence
<220> FEATURE:
<223> OTHER INFORMATION: Synthetic peptide construct

<400> SEQUENCE: 57

Gly Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 58
<211> LENGTH: 47
<212> TYPE: PRT
<213> ORGANISM: Artificial Sequence
<220> FEATURE:
<223> OTHER INFORMATION: Synthetic peptide construct

<400> SEQUENCE: 58

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Glu Ser Ala Pro Val Glu Pro Ser Ser Pro His Ser Tyr

<210> SEQ ID NO 59
<211> LENGTH: 47
<212> TYPE: PRT
<213> ORGANISM: Artificial Sequence
<220> FEATURE:
<223> OTHER INFORMATION: Synthetic peptide construct

<400> SEQUENCE: 59

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Glu Pro Ser Ser Pro His Ser Tyr
        35                  40                  45

<210> SEQ ID NO 60
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 60

Gly Thr Met Gln Val Gln Asn Leu Ser His Arg Leu Trp Gln Leu Arg
1               5                   10                  15

Gln Asp Ser Ala Pro Val Glu Pro Ser Ser Pro His Ser Tyr
            20                  25                  30

<210> SEQ ID NO 61
<211> LENGTH: 40
<212> TYPE: PRT
<213> ORGANISM: Artificial Sequence
<220> FEATURE:
<223> OTHER INFORMATION: Synthetic peptide construct

<400> SEQUENCE: 61

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Glu Pro Ser Ser Pro His Ser Tyr
        35                  40

<210> SEQ ID NO 62
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 62

Val Gly Cys Val Leu Gly Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 63
<211> LENGTH: 34
<212> TYPE: PRT

```
<213> ORGANISM: Artificial Sequence
<220> FEATURE:
<223> OTHER INFORMATION: Synthetic peptide construct

<400> SEQUENCE: 63

Gly Cys Asn Thr Ala Thr Cys Gln Val Gln Asn Leu Ser His Arg Leu
1               5                   10                  15

Trp Gln Leu Arg Gln Asp Ser Ala Pro Val Glu Pro Ser Ser Pro His
            20                  25                  30

Ser Tyr

<210> SEQ ID NO 64
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 64

Gly Cys Ser Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 65
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 65

Gly Cys Gly Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 66
<211> LENGTH: 34
<212> TYPE: PRT
<213> ORGANISM: Artificial Sequence
<220> FEATURE:
<223> OTHER INFORMATION: Synthetic peptide construct

<400> SEQUENCE: 66

Gly Cys Val Leu Gly Thr Cys Gln Val Gln Asn Leu Ser His Arg Leu
1               5                   10                  15

Trp Gln Leu Arg Gln Glu Ser Ala Pro Val Glu Pro Ser Ser Pro His
            20                  25                  30

Ser Tyr

<210> SEQ ID NO 67
<211> LENGTH: 11
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
```

```
<222> LOCATION: (1)..(1)
<223> OTHER INFORMATION: Lys, Arg or absent
<220> FEATURE:
<221> NAME/KEY: MISC_FEATURE
<222> LOCATION: (2)..(2)
<223> OTHER INFORMATION: Cys or absent
<220> FEATURE:
<221> NAME/KEY: MISC_FEATURE
<222> LOCATION: (3)..(3)
<223> OTHER INFORMATION: SEQ. ID. NO.68 or Z-XSerThr where X is L, V,
      M or I, Z is an alkanoyl group of about 1 to about 8 carbon atoms
      or absent; if Z-XSerThr, then X at position 1 and X at position 2
      are both absent
<220> FEATURE:
<221> NAME/KEY: MISC_FEATURE
<222> LOCATION: (4)..(4)
<223> OTHER INFORMATION: Cys or Ala
<220> FEATURE:
<221> NAME/KEY: MISC_FEATURE
<222> LOCATION: (5)..(5)
<223> OTHER INFORMATION: AlaThr, AlaSer, SerMet, GluThr or ValThr
<220> FEATURE:
<221> NAME/KEY: MISC_FEATURE
<222> LOCATION: (6)..(6)
<223> OTHER INFORMATION: Gln, Ala or Asn
<220> FEATURE:
<221> NAME/KEY: MISC_FEATURE
<222> LOCATION: (7)..(7)
<223> OTHER INFORMATION: ArgLeuAla, HisLeuAla, ArgIleAla, LysIleAla,
      ArgMetAla, HisMetAla, LysMetAla or ArgLeuThr
<220> FEATURE:
<221> NAME/KEY: MISC_FEATURE
<222> LOCATION: (8)..(8)
<223> OTHER INFORMATION: Asn, Ala or Gln
<220> FEATURE:
<221> NAME/KEY: MISC_FEATURE
<222> LOCATION: (9)..(9)
<223> OTHER INFORMATION: PheLeu, PheIle, PheMet, TyrLeu, TyrIle, TyrMet,
      TrpIle or TrpMet
<220> FEATURE:
<221> NAME/KEY: MISC_FEATURE
<222> LOCATION: (10)..(10)
<223> OTHER INFORMATION: Val, Ala, Ile, Met, Leu, PentylGly, or
      t-butylGly
<220> FEATURE:
<221> NAME/KEY: MISC_FEATURE
<222> LOCATION: (11)..(11)
<223> OTHER INFORMATION: SEQ ID NO:69, 70, 71, 72, 73, 74, 75, 76, 77,
      78, 79, ArgSer, LysSer, HisSer, ArgThr, ProSer or Arg

<400> SEQUENCE: 67

Xaa Xaa Xaa Xaa Xaa Xaa Xaa Xaa Xaa Xaa Xaa
1               5                   10

<210> SEQ ID NO 68
<211> LENGTH: 4
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Asn, Gln or Asp
<220> FEATURE:
<221> NAME/KEY: MISC_FEATURE
<222> LOCATION: (2)..(2)
<223> OTHER INFORMATION: Thr, Ser, Met, Val, Leu or Ile
<220> FEATURE:
<221> NAME/KEY: MISC_FEATURE
<222> LOCATION: (3)..(3)
<223> OTHER INFORMATION: Ala or Val
<220> FEATURE:
<221> NAME/KEY: MISC_FEATURE
<222> LOCATION: (4)..(4)
<223> OTHER INFORMATION: Thr or Ser
```

```
<400> SEQUENCE: 68

Xaa Xaa Xaa Xaa
1

<210> SEQ ID NO 69
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 69

Arg Ser Ser Gly Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 70

Lys Ser Ser Gly Tyr
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 71

His Ser Ser Gly Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 72

Pro Ser Ser Gly Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 73

Arg Ser Arg Gly Tyr
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 74
```

```
Arg Thr Ser Gly Tyr
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 75

Arg Ala Ser Gly Tyr
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 76

Ala Ser Ser Gly Tyr
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 77

Arg Ser Ala Gly Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic peptide construct

<400> SEQUENCE: 78

His Ser Ala Gly Tyr
1               5

<210> SEQ ID NO 79
<211> LENGTH: 4
<212> TYPE: PRT
<213> ORGANISM: Artificial Sequence
<220> FEATURE:
<223> OTHER INFORMATION: Synthetic peptide construct

<400> SEQUENCE: 79

Arg Ser Gly Tyr
1

<210> SEQ ID NO 80
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
```

```
<223> OTHER INFORMATION: A, C, hC, D, E, F, I, L, K, hK, R, hR, S, Hse,
      T, G, Q, N, M, Y, W, P, Hyp, H, V or absent
<220> FEATURE:
<221> NAME/KEY: MISC_FEATURE
<222> LOCATION: (2)..(2)
<223> OTHER INFORMATION: variable amino acid
<220> FEATURE:
<221> NAME/KEY: MISC_FEATURE
<222> LOCATION: (3)..(3)
<223> OTHER INFORMATION: A, D, E, N, Q, G, V, R, K, hK, hR, H, I, L, M,
      or absent
<220> FEATURE:
<221> NAME/KEY: MISC_FEATURE
<222> LOCATION: (4)..(4)
<223> OTHER INFORMATION: A, I, L, S, Hse, T, V, M, or absent
<220> FEATURE:
<221> NAME/KEY: MISC_FEATURE
<222> LOCATION: (5)..(5)
<223> OTHER INFORMATION: A, S, T, Hse, Y, V,  I, L, or M
<220> FEATURE:
<221> NAME/KEY: MISC_FEATURE
<222> LOCATION: (6)..(6)
<223> OTHER INFORMATION: T, A, S, Hse, Y, V, I, L, or M
<220> FEATURE:
<221> NAME/KEY: MISC_FEATURE
<222> LOCATION: (7)..(7)
<223> OTHER INFORMATION: variable amino acid
<220> FEATURE:
<221> NAME/KEY: MISC_FEATURE
<222> LOCATION: (8)..(8)
<223> OTHER INFORMATION: A, V, I, L, F, or M
<220> FEATURE:
<221> NAME/KEY: MISC_FEATURE
<222> LOCATION: (9)..(9)
<223> OTHER INFORMATION: L, T, S, Hse, V, I, or M
<220> FEATURE:
<221> NAME/KEY: MISC_FEATURE
<222> LOCATION: (10)..(10)
<223> OTHER INFORMATION: G, H, Q, K, R, N, hK, or hR
<220> FEATURE:
<221> NAME/KEY: MISC_FEATURE
<222> LOCATION: (11)..(11)
<223> OTHER INFORMATION: K, R, Q, N, hK, hR, or H
<220> FEATURE:
<221> NAME/KEY: MISC_FEATURE
<222> LOCATION: (12)..(12)
<223> OTHER INFORMATION: L, I, V, F, M, W, or Y
<220> FEATURE:
<221> NAME/KEY: MISC_FEATURE
<222> LOCATION: (13)..(13)
<223> OTHER INFORMATION: A, F, Y, N, Q, S, Hse, or T
<220> FEATURE:
<221> NAME/KEY: MISC_FEATURE
<222> LOCATION: (14)..(14)
<223> OTHER INFORMATION: A, D, E, G, N, K, Q, R, H, hR, or hK
<220> FEATURE:
<221> NAME/KEY: MISC_FEATURE
<222> LOCATION: (15)..(15)
<223> OTHER INFORMATION: A, D, E, F, L, S, Y, I, V, or M
<220> FEATURE:
<221> NAME/KEY: MISC_FEATURE
<222> LOCATION: (16)..(16)
<223> OTHER INFORMATION: L, F, M, V, Y, or I
<220> FEATURE:
<221> NAME/KEY: MISC_FEATURE
<222> LOCATION: (17)..(17)
<223> OTHER INFORMATION: H, Q, N, S, Hse, T, or V
<220> FEATURE:
<221> NAME/KEY: MISC_FEATURE
<222> LOCATION: (18)..(18)
<223> OTHER INFORMATION: K, hK, R, hR, H, u (Cit), or n (Orn)
<220> FEATURE:
<221> NAME/KEY: MISC_FEATURE
<222> LOCATION: (19)..(19)
<223> OTHER INFORMATION: F, L, S, Hse,V, I, T, or absent
<220> FEATURE:
<221> NAME/KEY: MISC_FEATURE
<222> LOCATION: (20)..(20)
<223> OTHER INFORMATION: H, R, K, hR, hK, N, Q, or absent
```

-continued

```
<220> FEATURE:
<221> NAME/KEY: MISC_FEATURE
<222> LOCATION: (21)..(21)
<223> OTHER INFORMATION: T, S, Hse, V, I, L, Q, N, or absent
<220> FEATURE:
<221> NAME/KEY: MISC_FEATURE
<222> LOCATION: (22)..(22)
<223> OTHER INFORMATION: F, L, M, V, Y, or I
<220> FEATURE:
<221> NAME/KEY: MISC_FEATURE
<222> LOCATION: (23)..(23)
<223> OTHER INFORMATION: P or Hyp
<220> FEATURE:
<221> NAME/KEY: MISC_FEATURE
<222> LOCATION: (24)..(24)
<223> OTHER INFORMATION: P, Hyp, R, K, hR, hK, or H
<220> FEATURE:
<221> NAME/KEY: MISC_FEATURE
<222> LOCATION: (25)..(25)
<223> OTHER INFORMATION: T, S, Hse, V, I, L, F, or Y
<220> FEATURE:
<221> NAME/KEY: MISC_FEATURE
<222> LOCATION: (26)..(26)
<223> OTHER INFORMATION: N, Q, D, or E
<220> FEATURE:
<221> NAME/KEY: MISC_FEATURE
<222> LOCATION: (27)..(27)
<223> OTHER INFORMATION: T, V, S, F, I, or L
<220> FEATURE:
<221> NAME/KEY: MISC_FEATURE
<222> LOCATION: (28)..(28)
<223> OTHER INFORMATION: G or A
<220> FEATURE:
<221> NAME/KEY: MISC_FEATURE
<222> LOCATION: (29)..(29)
<223> OTHER INFORMATION: S, Hse, T, V, I, L, or Y
<220> FEATURE:
<221> NAME/KEY: MISC_FEATURE
<222> LOCATION: (30)..(30)
<223> OTHER INFORMATION: E, G, K, N, D, R, hR, hK, H, or Q
<220> FEATURE:
<221> NAME/KEY: MISC_FEATURE
<222> LOCATION: (31)..(31)
<223> OTHER INFORMATION: A, T, S, Hse, V, I, L, F, or Y
<220> FEATURE:
<221> NAME/KEY: MISC_FEATURE
<222> LOCATION: (32)..(32)
<223> OTHER INFORMATION: F, P, Y, Hse, S, T, or Hyp

<400> SEQUENCE: 80

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: A, C, D, F, I, K, S, T, or absent
<220> FEATURE:
<221> NAME/KEY: MISC_FEATURE
<222> LOCATION: (2)..(2)
<223> OTHER INFORMATION: C, D, S, or absent
<220> FEATURE:
<221> NAME/KEY: MISC_FEATURE
<222> LOCATION: (3)..(3)
<223> OTHER INFORMATION: A, D, N, or absent
<220> FEATURE:
<221> NAME/KEY: MISC_FEATURE
<222> LOCATION: (4)..(4)
```

```
<223> OTHER INFORMATION: A, L, T, or absent
<220> FEATURE:
<221> NAME/KEY: MISC_FEATURE
<222> LOCATION: (5)..(5)
<223> OTHER INFORMATION: A or S
<220> FEATURE:
<221> NAME/KEY: MISC_FEATURE
<222> LOCATION: (6)..(6)
<223> OTHER INFORMATION: T, A, S or V
<220> FEATURE:
<221> NAME/KEY: MISC_FEATURE
<222> LOCATION: (7)..(7)
<223> OTHER INFORMATION: C, K or A
<220> FEATURE:
<221> NAME/KEY: MISC_FEATURE
<222> LOCATION: (8)..(8)
<223> OTHER INFORMATION: A, V, L, or M
<220> FEATURE:
<221> NAME/KEY: MISC_FEATURE
<222> LOCATION: (9)..(9)
<223> OTHER INFORMATION: L or T
<220> FEATURE:
<221> NAME/KEY: MISC_FEATURE
<222> LOCATION: (10)..(10)
<223> OTHER INFORMATION: G, H or Q
<220> FEATURE:
<221> NAME/KEY: MISC_FEATURE
<222> LOCATION: (11)..(11)
<223> OTHER INFORMATION: K, R, Q, or hArg
<220> FEATURE:
<221> NAME/KEY: MISC_FEATURE
<222> LOCATION: (12)..(12)
<223> OTHER INFORMATION: L, W or Y
<220> FEATURE:
<221> NAME/KEY: MISC_FEATURE
<222> LOCATION: (13)..(13)
<223> OTHER INFORMATION: A, F, N, Q, S, or T
<220> FEATURE:
<221> NAME/KEY: MISC_FEATURE
<222> LOCATION: (14)..(14)
<223> OTHER INFORMATION: A, D, E, G, N, K, Q, or R
<220> FEATURE:
<221> NAME/KEY: MISC_FEATURE
<222> LOCATION: (15)..(15)
<223> OTHER INFORMATION: A, D, E, F, L, S, or Y
<220> FEATURE:
<221> NAME/KEY: MISC_FEATURE
<222> LOCATION: (16)..(16)
<223> OTHER INFORMATION: L or F
<220> FEATURE:
<221> NAME/KEY: MISC_FEATURE
<222> LOCATION: (17)..(17)
<223> OTHER INFORMATION: H, Q, S, or V
<220> FEATURE:
<221> NAME/KEY: MISC_FEATURE
<222> LOCATION: (18)..(18)
<223> OTHER INFORMATION: K, R, hArg, u (Cit), or n (Orn)
<220> FEATURE:
<221> NAME/KEY: MISC_FEATURE
<222> LOCATION: (19)..(19)
<223> OTHER INFORMATION: F, L, S, or absent
<220> FEATURE:
<221> NAME/KEY: MISC_FEATURE
<222> LOCATION: (20)..(20)
<223> OTHER INFORMATION: H, Q or absent
<220> FEATURE:
<221> NAME/KEY: MISC_FEATURE
<222> LOCATION: (21)..(21)
<223> OTHER INFORMATION: T, N or absent
<220> FEATURE:
<221> NAME/KEY: MISC_FEATURE
<222> LOCATION: (22)..(22)
<223> OTHER INFORMATION: F, L, M, V, or Y
<220> FEATURE:
<221> NAME/KEY: MISC_FEATURE
<222> LOCATION: (24)..(24)
<223> OTHER INFORMATION: P or R
<220> FEATURE:
<221> NAME/KEY: MISC_FEATURE
```

```
<222> LOCATION: (27)..(27)
<223> OTHER INFORMATION: T or V
<220> FEATURE:
<221> NAME/KEY: MISC_FEATURE
<222> LOCATION: (30)..(30)
<223> OTHER INFORMATION: E, G, K, or N
<220> FEATURE:
<221> NAME/KEY: MISC_FEATURE
<222> LOCATION: (31)..(31)
<223> OTHER INFORMATION: A or T
<220> FEATURE:
<221> NAME/KEY: MISC_FEATURE
<222> LOCATION: (32)..(32)
<223> OTHER INFORMATION: F, P or Y

<400> SEQUENCE: 81

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: A, C, F, I, K, S, or absent
<220> FEATURE:
<221> NAME/KEY: MISC_FEATURE
<222> LOCATION: (2)..(2)
<223> OTHER INFORMATION: C, D, or S
<220> FEATURE:
<221> NAME/KEY: MISC_FEATURE
<222> LOCATION: (3)..(3)
<223> OTHER INFORMATION: A, D, or N
<220> FEATURE:
<221> NAME/KEY: MISC_FEATURE
<222> LOCATION: (4)..(4)
<223> OTHER INFORMATION: A, L, or T
<220> FEATURE:
<221> NAME/KEY: MISC_FEATURE
<222> LOCATION: (5)..(5)
<223> OTHER INFORMATION: A or S
<220> FEATURE:
<221> NAME/KEY: MISC_FEATURE
<222> LOCATION: (7)..(7)
<223> OTHER INFORMATION: C or K
<220> FEATURE:
<221> NAME/KEY: MISC_FEATURE
<222> LOCATION: (8)..(8)
<223> OTHER INFORMATION: A or V
<220> FEATURE:
<221> NAME/KEY: MISC_FEATURE
<222> LOCATION: (9)..(9)
<223> OTHER INFORMATION: L or T
<220> FEATURE:
<221> NAME/KEY: MISC_FEATURE
<222> LOCATION: (10)..(10)
<223> OTHER INFORMATION: G, H, or Q
<220> FEATURE:
<221> NAME/KEY: MISC_FEATURE
<222> LOCATION: (11)..(11)
<223> OTHER INFORMATION: K, R, or hArg
<220> FEATURE:
<221> NAME/KEY: MISC_FEATURE
<222> LOCATION: (13)..(13)
<223> OTHER INFORMATION: A, F, N, S, or T
<220> FEATURE:
<221> NAME/KEY: MISC_FEATURE
<222> LOCATION: (14)..(14)
<223> OTHER INFORMATION: A, D, E, G, N, Q, or R
<220> FEATURE:
```

```
<221> NAME/KEY: MISC_FEATURE
<222> LOCATION: (15)..(15)
<223> OTHER INFORMATION: A, E, F, L, S, or Y
<220> FEATURE:
<221> NAME/KEY: MISC_FEATURE
<222> LOCATION: (17)..(17)
<223> OTHER INFORMATION: H, S, or V
<220> FEATURE:
<221> NAME/KEY: MISC_FEATURE
<222> LOCATION: (18)..(18)
<223> OTHER INFORMATION: K, R, hArg, u (Cit), or n (Orn)
<220> FEATURE:
<221> NAME/KEY: MISC_FEATURE
<222> LOCATION: (19)..(19)
<223> OTHER INFORMATION: F, L, or S
<220> FEATURE:
<221> NAME/KEY: MISC_FEATURE
<222> LOCATION: (20)..(20)
<223> OTHER INFORMATION: H or Q
<220> FEATURE:
<221> NAME/KEY: MISC_FEATURE
<222> LOCATION: (21)..(21)
<223> OTHER INFORMATION: T or N
<220> FEATURE:
<221> NAME/KEY: MISC_FEATURE
<222> LOCATION: (22)..(22)
<223> OTHER INFORMATION: F, L, M, V, or Y
<220> FEATURE:
<221> NAME/KEY: MISC_FEATURE
<222> LOCATION: (24)..(24)
<223> OTHER INFORMATION: P or R
<220> FEATURE:
<221> NAME/KEY: MISC_FEATURE
<222> LOCATION: (27)..(27)
<223> OTHER INFORMATION: T or V
<220> FEATURE:
<221> NAME/KEY: MISC_FEATURE
<222> LOCATION: (30)..(30)
<223> OTHER INFORMATION: E, G, K, or N
<220> FEATURE:
<221> NAME/KEY: MISC_FEATURE
<222> LOCATION: (31)..(31)
<223> OTHER INFORMATION: A or T
<220> FEATURE:
<221> NAME/KEY: MISC_FEATURE
<222> LOCATION: (32)..(32)
<223> OTHER INFORMATION: F, P or Y

<400> SEQUENCE: 82

Xaa Xaa Xaa Xaa Xaa Thr Xaa Xaa Xaa Xaa Xaa Leu Xaa Xaa Xaa Leu
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: A, C, D, F, K, T, or absent
<220> FEATURE:
<221> NAME/KEY: MISC_FEATURE
<222> LOCATION: (2)..(2)
<223> OTHER INFORMATION: A, C, D, S, or absent
<220> FEATURE:
<221> NAME/KEY: MISC_FEATURE
<222> LOCATION: (3)..(3)
<223> OTHER INFORMATION: A, D, N, or absent
<220> FEATURE:
<221> NAME/KEY: MISC_FEATURE
<222> LOCATION: (4)..(4)
<223> OTHER INFORMATION: A, L, T, or absent
```

```
<220> FEATURE:
<221> NAME/KEY: MISC_FEATURE
<222> LOCATION: (5)..(5)
<223> OTHER INFORMATION: A or S
<220> FEATURE:
<221> NAME/KEY: MISC_FEATURE
<222> LOCATION: (6)..(6)
<223> OTHER INFORMATION: A, S, T or V
<220> FEATURE:
<221> NAME/KEY: MISC_FEATURE
<222> LOCATION: (7)..(7)
<223> OTHER INFORMATION: A, C or K
<220> FEATURE:
<221> NAME/KEY: MISC_FEATURE
<222> LOCATION: (8)..(8)
<223> OTHER INFORMATION: A, L, M, or V
<220> FEATURE:
<221> NAME/KEY: MISC_FEATURE
<222> LOCATION: (9)..(9)
<223> OTHER INFORMATION: L or T
<220> FEATURE:
<221> NAME/KEY: MISC_FEATURE
<222> LOCATION: (10)..(10)
<223> OTHER INFORMATION: G, H, or Q
<220> FEATURE:
<221> NAME/KEY: MISC_FEATURE
<222> LOCATION: (11)..(11)
<223> OTHER INFORMATION: K, Q, or R
<220> FEATURE:
<221> NAME/KEY: MISC_FEATURE
<222> LOCATION: (12)..(12)
<223> OTHER INFORMATION: L, W, or Y
<220> FEATURE:
<221> NAME/KEY: MISC_FEATURE
<222> LOCATION: (13)..(13)
<223> OTHER INFORMATION: A, N, Q, S, or T
<220> FEATURE:
<221> NAME/KEY: MISC_FEATURE
<222> LOCATION: (14)..(14)
<223> OTHER INFORMATION: A, D, E, G, K, N, Q, or R
<220> FEATURE:
<221> NAME/KEY: MISC_FEATURE
<222> LOCATION: (15)..(15)
<223> OTHER INFORMATION: A, D, E, F, L, S, or Y
<220> FEATURE:
<221> NAME/KEY: MISC_FEATURE
<222> LOCATION: (16)..(16)
<223> OTHER INFORMATION: F or L
<220> FEATURE:
<221> NAME/KEY: MISC_FEATURE
<222> LOCATION: (17)..(17)
<223> OTHER INFORMATION: H, Q, S or V
<220> FEATURE:
<221> NAME/KEY: MISC_FEATURE
<222> LOCATION: (18)..(18)
<223> OTHER INFORMATION: K or R
<220> FEATURE:
<221> NAME/KEY: MISC_FEATURE
<222> LOCATION: (19)..(19)
<223> OTHER INFORMATION: F, L, S, or absent
<220> FEATURE:
<221> NAME/KEY: MISC_FEATURE
<222> LOCATION: (20)..(20)
<223> OTHER INFORMATION: H, K, Q, or absent
<220> FEATURE:
<221> NAME/KEY: MISC_FEATURE
<222> LOCATION: (21)..(21)
<223> OTHER INFORMATION: Q, T, or absent
<220> FEATURE:
<221> NAME/KEY: MISC_FEATURE
<222> LOCATION: (22)..(22)
<223> OTHER INFORMATION: F, L, or Y
<220> FEATURE:
<221> NAME/KEY: MISC_FEATURE
<222> LOCATION: (24)..(24)
<223> OTHER INFORMATION: P or R
<220> FEATURE:
<221> NAME/KEY: MISC_FEATURE
<222> LOCATION: (27)..(27)
```

```
<223> OTHER INFORMATION: T or V
<220> FEATURE:
<221> NAME/KEY: MISC_FEATURE
<222> LOCATION: (30)..(30)
<223> OTHER INFORMATION: E, K or N
<220> FEATURE:
<221> NAME/KEY: MISC_FEATURE
<222> LOCATION: (31)..(31)
<223> OTHER INFORMATION: A or T
<220> FEATURE:
<221> NAME/KEY: MISC_FEATURE
<222> LOCATION: (32)..(32)
<223> OTHER INFORMATION: F, Y, or absent

<400> SEQUENCE: 83

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 84
<211> LENGTH: 4
<212> TYPE: PRT
<213> ORGANISM: Artificial Sequence
<220> FEATURE:
<223> OTHER INFORMATION: Synthetic peptide construct

<400> SEQUENCE: 84

Leu Gln Thr Tyr
1

<210> SEQ ID NO 85
<211> LENGTH: 32
<212> TYPE: PRT
<213> ORGANISM: Oncorhynchus sp.

<400> SEQUENCE: 85

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 86

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 87

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
```

20 25 30

<210> SEQ ID NO 88
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 88

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 89

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 90

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 91
<211> LENGTH: 34
<212> TYPE: PRT
<213> ORGANISM: Artificial Sequence
<220> FEATURE:
<223> OTHER INFORMATION: Synthetic peptide construct

<400> SEQUENCE: 91

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Asn Val Gly Ser Asn
            20                  25                  30

Thr Tyr

<210> SEQ ID NO 92
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 92

Ala Cys Asn Thr Ala Thr Cys Val Leu Gly Arg Leu Ser Gln Glu Leu

```
                1               5                  10                  15
His Arg Leu Gln Thr Tyr Pro Arg Thr Asn Thr Gly Ser Asn Thr Tyr
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 93

Lys Cys Ala Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 94

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 95

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 96

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 97
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 97
```

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 98
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 98

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 99

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 100
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 100

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 101
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 101

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
                20                  25                  30

<210> SEQ ID NO 102
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 102

```
Lys Cys Asn Thr Ala Thr Cys Ala Thr Gln Arg Leu Ser Gln Glu Leu
1               5                   10                  15

Arg Lys Leu Gln Thr Tyr Pro Arg Thr Asn Thr Gly Ser Asn Thr Tyr
            20                  25                  30
```

<210> SEQ ID NO 103
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 103

```
Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 104
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Acetyl-Cys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 104

```
Cys Xaa Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 105
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Acetyl-Lys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 105

```
Lys Xaa Asn Thr Ala Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 106
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 106

Ser Thr Ala Val Leu Xaa Xaa Leu Ser Gln Glu Leu Xaa Xaa Leu Gln
1               5                   10                  15

Thr Tyr Pro Arg Thr Asn Thr Gly Ser Asn Thr Tyr
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 107

Ser Thr Ala Val Leu Xaa Xaa Leu Ser Gln Glu Leu Xaa Xaa Leu Gln
1               5                   10                  15

Thr Tyr Pro Arg Thr Asn Val Gly Ser Asn Thr Tyr
            20                  25

<210> SEQ ID NO 108
<211> LENGTH: 28
<212> TYPE: PRT
<213> ORGANISM: Artificial Sequence
<220> FEATURE:
<223> OTHER INFORMATION: Synthetic peptide construct

```
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 108

Ser Thr Ala Val Leu Xaa Xaa Leu Ser Gln Glu Leu Xaa Xaa Leu Gln
1               5                   10                  15

Thr Tyr Pro Pro Thr Asn Val Gly Ser Asn Thr Tyr
            20                  25

<210> SEQ ID NO 109
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 109

Ser Thr Ala Val Leu Xaa Xaa Leu Ser Gln Glu Leu Xaa Xaa Leu Gln
1               5                   10                  15

Thr Leu Pro Pro Thr Asn Val Gly Ser Asn Thr Tyr
            20                  25

<210> SEQ ID NO 110
<211> LENGTH: 14
<212> TYPE: PRT
<213> ORGANISM: Artificial Sequence
<220> FEATURE:
<223> OTHER INFORMATION: Synthetic peptide construct

<400> SEQUENCE: 110

Leu Leu Gln Gln Trp Gln Lys Leu Leu Gln Lys Leu Lys Gln
1               5                   10
```

<210> SEQ ID NO 111
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 111

Lys Cys Asn Thr Ala Thr Cys Leu Leu Gln Gln Trp Gln Lys Leu Leu
1               5                   10                  15

Gln Lys Leu Lys Gln Leu Pro Arg Thr Asn Thr Gly Ser Asn Thr Tyr
            20                  25                  30

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide construct

<400> SEQUENCE: 112

Leu Leu Gln Gln Leu Gln Lys Leu Leu Gln Lys Leu Lys Gln Tyr
1               5                   10                  15

<210> SEQ ID NO 113
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 113

Lys Cys Asn Thr Ala Thr Cys Leu Leu Gln Gln Leu Gln Lys Leu Leu
1               5                   10                  15

Gln Lys Leu Lys Gln Tyr Pro Arg Thr Asn Thr Gly Ser Asn Thr Tyr
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 114

Lys Cys Asn Thr Ala Ser Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 115

Lys Cys Asn Thr Ala Val Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 116
<211> LENGTH: 29

```
<212> TYPE: PRT
<213> ORGANISM: Artificial Sequence
<220> FEATURE:
<223> OTHER INFORMATION: Synthetic peptide construct

<400> SEQUENCE: 116

Lys Cys Asn Thr Ala Thr Cys Val Leu Gly Arg Leu Ser Gln Glu Leu
1               5                   10                  15

His Arg Leu Pro Arg Thr Asn Thr Gly Ser Asn Thr Tyr
            20                  25

<210> SEQ ID NO 117
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 117

Lys Cys Asn Thr Ala Thr Cys Val Leu Gly Arg Leu Ser Gln Glu Leu
1               5                   10                  15

His Leu Pro Arg Thr Asn Thr Gly Ser Asn Thr Tyr
            20                  25

<210> SEQ ID NO 118
<211> LENGTH: 27
<212> TYPE: PRT
<213> ORGANISM: Artificial Sequence
<220> FEATURE:
<223> OTHER INFORMATION: Synthetic peptide construct

<400> SEQUENCE: 118

Lys Cys Asn Thr Ala Thr Cys Val Leu Gly Arg Leu Ser Gln Glu Leu
1               5                   10                  15

Tyr Pro Arg Thr Asn Thr Gly Ser Asn Thr Tyr
            20                  25

<210> SEQ ID NO 119
<211> LENGTH: 26
<212> TYPE: PRT
<213> ORGANISM: Artificial Sequence
<220> FEATURE:
<223> OTHER INFORMATION: Synthetic peptide construct

<400> SEQUENCE: 119

Lys Cys Asn Thr Ala Thr Cys Val Leu Gly Arg Leu Ser Gln Glu Tyr
1               5                   10                  15

Pro Arg Thr Asn Thr Gly Ser Asn Thr Tyr
            20                  25

<210> SEQ ID NO 120
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 120

Lys Cys Asn Thr Ala Thr Cys Val Leu Gly Arg Leu Ser Gln Tyr Pro
1               5                   10                  15

Arg Thr Asn Thr Gly Ser Asn Thr Tyr
            20                  25

<210> SEQ ID NO 121
```

```
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 121

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: D-Thr

<400> SEQUENCE: 122

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Acetyl-Lys
<220> FEATURE:
<221> NAME/KEY: MOD_RES
<222> LOCATION: (11)..(11)
<223> OTHER INFORMATION: Lys(PEG5000)
<220> FEATURE:
<221> NAME/KEY: MOD_RES
<222> LOCATION: (18)..(18)
<223> OTHER INFORMATION: Lys(PEG5000)

<400> SEQUENCE: 123

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
```

<222> LOCATION: (1)..(1)
<223> OTHER INFORMATION: Acetyl-Ala
<220> FEATURE:
<221> NAME/KEY: MOD_RES
<222> LOCATION: (11)..(11)
<223> OTHER INFORMATION: Lys(PEG5000)

<400> SEQUENCE: 124

Ala Cys Asn Thr Ala Thr Cys Val Leu Gly Xaa Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Acetyl-Ala
<220> FEATURE:
<221> NAME/KEY: MOD_RES
<222> LOCATION: (18)..(18)
<223> OTHER INFORMATION: Lys(PEG5000)

<400> SEQUENCE: 125

Ala Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 126
<211> LENGTH: 26
<212> TYPE: PRT
<213> ORGANISM: Artificial Sequence
<220> FEATURE:
<223> OTHER INFORMATION: Synthetic peptide construct

<400> SEQUENCE: 126

Lys Cys Asn Thr Ala Thr Cys Val Leu Gly Arg Leu Ser Gln Glu Leu
1               5                   10                  15

His Arg Leu Gln Thr Gly Ser Asn Thr Tyr
            20                  25

<210> SEQ ID NO 127
<211> LENGTH: 26
<212> TYPE: PRT
<213> ORGANISM: Artificial Sequence
<220> FEATURE:
<223> OTHER INFORMATION: Synthetic peptide construct

<400> SEQUENCE: 127

Lys Cys Asn Thr Ala Thr Cys Val Leu Gly Arg Leu Ser Gln Glu Leu
1               5                   10                  15

His Arg Leu Gln Thr Gly Ser Asn Thr Tyr
            20                  25

<210> SEQ ID NO 128
<211> LENGTH: 32
<212> TYPE: PRT
<213> ORGANISM: Artificial Sequence
<220> FEATURE:
<223> OTHER INFORMATION: Synthetic peptide construct

```
<400> SEQUENCE: 128

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 129

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 130

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 131

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 132

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Synthetic peptide construct
```

```
<220> FEATURE:
<221> NAME/KEY: MOD_RES
<222> LOCATION: (6)..(6)
<223> OTHER INFORMATION: Hse
<220> FEATURE:
<221> NAME/KEY: MOD_RES
<222> LOCATION: (6)..(6)

<400> SEQUENCE: 133

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Ahb

<400> SEQUENCE: 134

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Ahp

<400> SEQUENCE: 135

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Thr(OPO3H2)

<400> SEQUENCE: 136

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 137
<211> LENGTH: 28
```

<212> TYPE: PRT
<213> ORGANISM: Artificial Sequence
<220> FEATURE:
<223> OTHER INFORMATION: Synthetic peptide construct

<400> SEQUENCE: 137

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 138
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn

<400> SEQUENCE: 138

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Cit
<220> FEATURE:
<221> NAME/KEY: MOD_RES
<222> LOCATION: (18)..(18)
<223> OTHER INFORMATION: Cit

<400> SEQUENCE: 139

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: homoLys
<220> FEATURE:
<221> NAME/KEY: MOD_RES
<222> LOCATION: (18)..(18)
<223> OTHER INFORMATION: homoLys

<400> SEQUENCE: 140

```
Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30
```

<210> SEQ ID NO 141
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: L-Octylglycine

<400> SEQUENCE: 141

```
Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr
```

<210> SEQ ID NO 142
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: N-3,6-dioxaoctanoyl-Lys

<400> SEQUENCE: 142

```
Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 143
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(7)
<223> OTHER INFORMATION: Cyclo(1-7)

<400> SEQUENCE: 143

```
Asp Ser Asn Leu Ser Thr Leu Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 144
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (2)..(7)
<223> OTHER INFORMATION: Cyclo(2-7)

-continued

<400> SEQUENCE: 144

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (2)..(7)
<223> OTHER INFORMATION: Cyclo(2-7)

<400> SEQUENCE: 145

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 146

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 147

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: N-isocaproyl-Lys

<400> SEQUENCE: 148

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr

```
                  20                  25                  30
```

<210> SEQ ID NO 149
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: homoArg
<220> FEATURE:
<221> NAME/KEY: MOD_RES
<222> LOCATION: (18)..(18)
<223> OTHER INFORMATION: homoArg

<400> SEQUENCE: 149

```
Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30
```

<210> SEQ ID NO 150
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 150

```
Phe Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 151
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 151

```
Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 152
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 152

```
Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 153
<211> LENGTH: 32
<212> TYPE: PRT
<213> ORGANISM: Artificial Sequence -continued

```
<220> FEATURE:
<223> OTHER INFORMATION: Synthetic peptide construct

<400> SEQUENCE: 153

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 154

Lys Cys Asn Thr Ala Thr Cys Ala Thr Gln Arg Leu Ala Asp Phe Leu
1               5                   10                  15

Val His Leu Gln Thr Tyr Pro Thr Asn Val Gly Ser Asn Thr Tyr
            20                  25                  30

<210> SEQ ID NO 155
<211> LENGTH: 29
<212> TYPE: PRT
<213> ORGANISM: Artificial Sequence
<220> FEATURE:
<223> OTHER INFORMATION: Synthetic peptide construct

<400> SEQUENCE: 155

Cys Asn Thr Ala Thr Cys Ala Thr Gln Arg Leu Ala Asn Phe Leu Val
1               5                   10                  15

His Leu Gln Thr Tyr Pro Thr Asn Val Gly Ser Asn Thr
            20                  25

<210> SEQ ID NO 156
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 156

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 157

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
            20                  25                  30

<210> SEQ ID NO 158
<211> LENGTH: 32
<212> TYPE: PRT
```

<213> ORGANISM: Artificial Sequence
<220> FEATURE:
<223> OTHER INFORMATION: Synthetic peptide construct

<400> SEQUENCE: 158

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 159

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 160

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 161

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Gly Ser Asn Thr Tyr
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 162

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 163
<211> LENGTH: 32

```
<212> TYPE: PRT
<213> ORGANISM: Artificial Sequence
<220> FEATURE:
<223> OTHER INFORMATION: Synthetic peptide construct

<400> SEQUENCE: 163

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 164

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 165

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 166
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser

<400> SEQUENCE: 166

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 167
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 167

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
```

-continued

```
            20                  25                  30
```

<210> SEQ ID NO 168
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 168

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 169

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 170

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 171

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 172

Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Ac-Agy
<220> FEATURE:
<221> NAME/KEY: MOD_RES
<222> LOCATION: (7)..(7)
<223> OTHER INFORMATION: Agy

<400> SEQUENCE: 173

Xaa Ser Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Ac-Lys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 174

Lys Xaa Asn Thr Ala Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 175
<211> LENGTH: 27
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib

<400> SEQUENCE: 175

Ser Thr Ala Val Leu Xaa Arg Leu Ser Gln Glu Leu Arg Leu Gln Thr
1               5                   10                  15

Tyr Pro Arg Thr Asn Thr Gly Ser Gly Thr Pro
            20                  25

<210> SEQ ID NO 176
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (14)..(14)
<223> OTHER INFORMATION: Lys(For)

<400> SEQUENCE: 176

Ser Thr Ala Val Leu Gly Xaa Leu Ser Gln Glu Leu His Xaa Leu Gln
1               5                   10                  15

Thr Tyr Pro Arg Thr Asn Thr Gly Ser Gly Thr Pro
            20                  25

<210> SEQ ID NO 177
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 177

Ser Thr Ala Val Leu Xaa Xaa Leu Ser Gln Glu Leu Xaa Xaa Leu Gln
1               5                   10                  15

Thr Tyr Pro Arg Thr Asn Thr Gly Ser Asn Thr Tyr
            20                  25

<210> SEQ ID NO 178
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib

```
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 178

Ser Thr Ala Val Leu Xaa Xaa Leu Ser Gln Glu Leu Xaa Xaa Leu Gln
1               5                   10                  15

Thr Tyr Pro Arg Thr Asn Val Gly Ser Asn Thr Tyr
            20                  25

<210> SEQ ID NO 179
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 179

Lys Cys Asn Thr Ala Thr Cys Leu Leu Gln Gln Leu Gln Lys Leu Leu
1               5                   10                  15

Gln Lys Leu Lys Gln Tyr Pro Arg Thr Asn Thr Gly Ser Asn Thr Tyr
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 180

Lys Cys Asn Thr Ala Ser Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 181

Lys Cys Asn Thr Ala Val Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 182
<211> LENGTH: 29
<212> TYPE: PRT
<213> ORGANISM: Artificial Sequence
<220> FEATURE:
<223> OTHER INFORMATION: Synthetic peptide construct

<400> SEQUENCE: 182
```

```
Lys Cys Asn Thr Ala Thr Cys Val Leu Gly Arg Leu Ser Gln Glu Leu
1               5                   10                  15

His Arg Tyr Pro Arg Thr Asn Thr Gly Ser Asn Thr Tyr
            20                  25
```

<210> SEQ ID NO 183
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 183

```
Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30
```

<210> SEQ ID NO 184
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: d-Thr

<400> SEQUENCE: 184

```
Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 185
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: dAh

<400> SEQUENCE: 185

```
Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 186
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES -continued

```
<222> LOCATION: (1)..(1)
<223> OTHER INFORMATION: Ac-Ala
<220> FEATURE:
<221> NAME/KEY: MOD_RES
<222> LOCATION: (18)..(18)
<223> OTHER INFORMATION: Lys(PEG5000)

<400> SEQUENCE: 186

Ala Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 187
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 187

Lys Cys Asn Thr Ala Thr Cys Val Leu Gly Arg Leu Ser Gln Glu Leu
1               5                   10                  15

His Arg Leu Gln Thr Leu Gln Thr Tyr Pro Arg Thr Asn Thr Gly Ser
            20                  25                  30

Asn Thr Tyr
        35

<210> SEQ ID NO 188
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 188

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30

Ser Asn Thr Tyr
        35

<210> SEQ ID NO 189
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 189

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 190
```

-continued

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 191

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 192

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 193

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Hse

<400> SEQUENCE: 194

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 195
<211> LENGTH: 32
<212> TYPE: PRT
<213> ORGANISM: Artificial Sequence

```
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Ahb

<400> SEQUENCE: 195

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Ahp

<400> SEQUENCE: 196

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (6)..(6)
<223> OTHER INFORMATION: Thr(OPO3H2)

<400> SEQUENCE: 197

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn

<400> SEQUENCE: 198

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30
```

```
<210> SEQ ID NO 199
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Cit
<220> FEATURE:
<221> NAME/KEY: MOD_RES
<222> LOCATION: (18)..(18)
<223> OTHER INFORMATION: Cit

<400> SEQUENCE: 199

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: hLys
<220> FEATURE:
<221> NAME/KEY: MOD_RES
<222> LOCATION: (18)..(18)
<223> OTHER INFORMATION: hLys

<400> SEQUENCE: 200

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 201
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: L-Octylglycine

<400> SEQUENCE: 201

Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr

<210> SEQ ID NO 202
<211> LENGTH: 31
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
```

```
<222> LOCATION: (1)..(1)
<223> OTHER INFORMATION: N-3,6-dioxaoctanoyl-Cys

<400> SEQUENCE: 202

Cys Asn Thr Ala Thr Cys Val Leu Gly Arg Leu Ser Gln Glu Leu His
1               5                   10                  15

Arg Leu Gln Thr Val Pro Arg Thr Asn Thr Gly Ser Asn Thr Tyr
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 203

Lys Cys Asn Thr Ala Thr Cys Met Leu Gly Arg Tyr Thr Gln Asp Phe
1               5                   10                  15

His Arg Leu Gln Thr Tyr Pro Arg Thr Asn Thr Gly Ser Asn Thr Tyr
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 204

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 205

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 206
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 206

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 207
<211> LENGTH: 33
<212> TYPE: PRT
```

```
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (33)..(33)
<223> OTHER INFORMATION: 9Anc

<400> SEQUENCE: 207

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 208
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (33)..(33)
<223> OTHER INFORMATION: L-octylglycine

<400> SEQUENCE: 208

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 209
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: N-isocaproyl-Lys

<400> SEQUENCE: 209

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: hArg
<220> FEATURE:
<221> NAME/KEY: MOD_RES
<222> LOCATION: (18)..(18)
<223> OTHER INFORMATION: hArg

<400> SEQUENCE: 210

Lys Cys Asn Thr Ala Thr Cys Val Leu Gly Xaa Leu Ser Gln Glu Leu
```

```
                1               5                  10                  15
His Xaa Leu Gln Thr Tyr Pro Arg Thr Asn Thr Gly Ser Asn Thr Tyr
        20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 211

Phe Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
        20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (18)..(18)
<223> OTHER INFORMATION: Cit

<400> SEQUENCE: 212

Lys Cys Asn Thr Ala Thr Cys Val Leu Gly Arg Leu Ser Gln Glu Leu
1               5                   10                  15
His Xaa Leu Gln Thr Tyr Pro Arg Thr Asn Thr Gly Ser Asn Thr Tyr
        20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (18)..(18)
<223> OTHER INFORMATION: Orn

<400> SEQUENCE: 213

Lys Cys Asn Thr Ala Thr Cys Val Leu Gly Arg Leu Ser Gln Glu Leu
1               5                   10                  15
His Xaa Leu Gln Thr Tyr Pro Arg Thr Asn Thr Gly Ser Asn Thr Tyr
        20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 214

Ile Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
        20                  25                  30

<210> SEQ ID NO 215
```

```
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Octylglycine

<400> SEQUENCE: 215

Xaa Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Cys

<400> SEQUENCE: 216

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Cit

<400> SEQUENCE: 217

Lys Cys Asn Thr Ala Thr Cys Val Leu Gly Xaa Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 218
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (33)..(33)
<223> OTHER INFORMATION: 4ABU

<400> SEQUENCE: 218

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa
```

<210> SEQ ID NO 219
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Lys
<220> FEATURE:
<221> NAME/KEY: MOD_RES
<222> LOCATION: (33)..(33)
<223> OTHER INFORMATION: 4ABU

<400> SEQUENCE: 219

Lys Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
            20                  25                  30
Xaa

<210> SEQ ID NO 220
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 220

Lys Cys Asn Thr Ser Thr Cys Ala Thr Gln Arg Leu Ala Asn Glu Leu
1               5                   10                  15
Val Arg Leu Gln Thr Tyr Pro Arg Thr Asn Val Gly Ser Glu Ala Phe
            20                  25                  30

<210> SEQ ID NO 221
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 221

Lys Cys Asn Thr Ala Thr Cys Val Leu Gly Arg Leu Ser Gln Glu Leu
1               5                   10                  15
His Arg Leu Gln Thr Tyr Pro Thr Asn Val Gly Ser Glu Ala Phe
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 222

Lys Cys Asn Thr Ala Thr Cys Val Leu Gly Arg Leu Ser Arg Ser Leu
1               5                   10                  15
His Arg Leu Gln Thr Tyr Pro Arg Thr Asn Thr Gly Ser Asn Thr Tyr
            20                  25                  30

<210> SEQ ID NO 223
<211> LENGTH: 32
<212> TYPE: PRT

<213> ORGANISM: Artificial Sequence
<220> FEATURE:
<223> OTHER INFORMATION: Synthetic peptide construct

<400> SEQUENCE: 223

Lys Cys Asn Thr Ala Thr Cys Val Thr His Arg Leu Ser Gln Glu Leu
1               5                   10                  15
His Arg Leu Gln Thr Tyr Pro Arg Thr Asn Thr Gly Ser Asn Thr Tyr
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 224

Lys Cys Asn Thr Ala Thr Cys Val Leu Gly Arg Leu Ala Asp Phe Leu
1               5                   10                  15
His Arg Leu Gln Thr Tyr Pro Arg Thr Asn Thr Gly Ser Asn Thr Tyr
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 225

Cys Asn Thr Ala Thr Cys Val Leu Gly Arg Leu Ser Gln Glu Leu His
1               5                   10                  15
Arg Leu Gln Thr Tyr Pro Arg Thr Asn Thr Gly Ser Asn Thr
            20                  25                  30

<210> SEQ ID NO 226
<211> LENGTH: 33
<212> TYPE: PRT
<213> ORGANISM: Artificial Sequence
<220> FEATURE:
<223> OTHER INFORMATION: Synthetic peptide construct

<400> SEQUENCE: 226

Lys Cys Asn Thr Ala Thr Cys Val Leu Gly Arg Leu Ser Gln Glu Leu
1               5                   10                  15
His Arg Leu Gln Asn Phe Val Pro Arg Thr Asn Thr Gly Ser Asn Thr
            20                  25                  30
Tyr

<210> SEQ ID NO 227
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 227

Lys Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Glu Thr Phe
            20                  25                  30

```
<210> SEQ ID NO 228
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 228

Ala Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 229

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Lys Ala Phe
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 230

Lys Cys Asp Thr Ala Thr Cys Val Thr His Arg Leu Ala Gly Leu Leu
1               5                   10                  15

Ser Arg Ser Gln Thr Tyr Pro Arg Thr Asn Thr Gly Ser Asn Thr Tyr
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 231

Lys Cys Asn Thr Ala Thr Cys Val Leu Gly Arg Leu Ala Asp Ala Leu
1               5                   10                  15

His Arg Leu Gln Thr Tyr Pro Arg Thr Asn Thr Gly Ser Asn Thr Tyr
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 232

Lys Cys Asn Thr Ala Thr Cys Val Leu Gly Arg Leu Ala Ala Phe Leu
1               5                   10                  15

His Arg Leu Gln Thr Tyr Pro Arg Thr Asn Thr Gly Ser Asn Thr Tyr
            20                  25                  30
```

```
<210> SEQ ID NO 233
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 233

Ser Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 234

Lys Cys Asn Thr Ala Thr Cys Val Leu Gly Arg Leu Ser Gln Glu Leu
1               5                   10                  15

His Arg Leu Gln Thr Met Pro Arg Thr Asn Thr Gly Ser Asn Thr Tyr
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 235

Lys Cys Asn Thr Ala Thr Cys Val Leu Gly Arg Leu Ser Gln Glu Leu
1               5                   10                  15

His Arg Leu Gln Thr Val Pro Arg Thr Asn Thr Gly Ser Asn Thr Tyr
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 236

Lys Cys Asn Thr Ala Thr Cys Val Leu Gly Arg Leu Asn Glu Tyr Leu
1               5                   10                  15

His Arg Leu Gln Thr Tyr Pro Arg Thr Asn Thr Gly Ser Asn Thr Tyr
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 237

Ser Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 238
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 238

```
Lys Cys Asn Thr Ala Thr Cys Val Leu Gly Arg Leu Thr Glu Phe Leu
1               5                  10                  15
His Arg Leu Gln Thr Tyr Pro Arg Thr Asn Thr Gly Ser Asn Thr Tyr
            20                  25                  30
```

<210> SEQ ID NO 239
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 239

```
Lys Cys Asn Thr Ala Thr Cys Val Leu Gly Arg Leu Ala Glu Phe Leu
1               5                  10                  15
His Arg Leu Gln Thr Tyr Pro Arg Thr Asn Thr Gly Ser Asn Thr Tyr
            20                  25                  30
```

<210> SEQ ID NO 240
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 240

```
Lys Cys Asn Thr Ala Thr Cys Val Leu Gly Arg Leu Thr Asp Tyr Leu
1               5                  10                  15
His Arg Leu Gln Thr Tyr Pro Arg Thr Asn Thr Gly Ser Asn Thr Tyr
            20                  25                  30
```

<210> SEQ ID NO 241
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 241

```
Lys Cys Asn Thr Ala Thr Cys Val Leu Gly Arg Leu Ala Gln Phe Leu
1               5                  10                  15
His Arg Leu Gln Thr Tyr Pro Arg Thr Asn Thr Gly Ser Asn Thr Tyr
            20                  25                  30
```

<210> SEQ ID NO 242
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 242

```
Lys Cys Asn Thr Ala Thr Cys Val Leu Gly Arg Leu Ala Asp Phe Leu
1               5                  10                  15
His Arg Phe Gln Thr Phe Pro Arg Thr Asn Thr Gly Ser Asn Thr Tyr
```

20                  25                  30

<210> SEQ ID NO 243
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 243

Lys Cys Asn Thr Ala Thr Cys Val Leu Gly Arg Leu Ala Asp Phe Leu
1               5                   10                  15

His Arg Phe His Thr Phe Pro Arg Thr Asn Thr Gly Ser Asn Thr Tyr
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 244

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Gly Thr Pro
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 245

Cys Asn Thr Ala Thr Cys Val Leu Gly Arg Leu Ala Asp Phe Leu His
1               5                   10                  15

Arg Leu Gln Thr Tyr Pro Arg Thr Asn Thr Gly Ser Asn Thr Tyr
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 246

Lys Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 247

Lys Cys Asn Thr Ala Thr Cys Val Leu Gly Arg Leu Phe Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 248

Lys Cys Asn Thr Ala Thr Cys Val Leu Gly Arg Leu Ala Ala Ala Leu
1               5                   10                  15

His Arg Leu Gln Thr Tyr Pro Arg Thr Asn Thr Gly Ser Asn Thr Tyr
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 249

Thr Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 250

Cys Ser Asn Leu Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 251
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 251

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 252

Cys Ser Asn Leu Ser Thr Cys Val Leu Gly Arg Leu Ser Gln Glu Leu
1               5                   10                  15

-continued

```
His Arg Leu Gln Thr Tyr Pro Arg Thr Asn Thr Gly Ser Asn Thr Tyr
            20                  25                  30

<210> SEQ ID NO 253
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 253

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

METHODS FOR CONTROLLING BINGE EATING DISORDERS

CROSS-REFERENCE TO RELATED APPLICATIONS

This application is a national application of International PCT Application No. PCT/US2006/011768, filed Mar. 31, 2006, now published as WO2006/105345, which claims priority to U.S. Provisional Application No. 60/666,681 filed Mar. 31, 2005; U.S. Provisional Application No. 60/667,335, filed Mar. 31, 2005; U.S. Provisional Application 60/675,441, filed Apr. 28, 2005 and U.S. Provisional Application No. 60/760,583, filed Jan. 20, 2006; priority to all of which is hereby claimed. All applications are hereby incorporated by reference in their entireties and for all purposes.

TECHNICAL FIELD

This disclosure relates the medical field and in particular to the fields of health, diet, and nutrition. This disclosure relates to uses of peptides, and more particularly to uses of amylin and amylin agonists.

BACKGROUND

The amylin family of peptide hormones, including amylin, calcitonin, calcitonin gene related peptide (CGRP), adrenomedullin (ADM), and intermedin (also known as "AFP-6") is a family of peptide hormones generally implicated in metabolic conditions and disorders. It has been reported that the biological actions of amylin family peptide hormones are generally mediated via binding to two closely related type II G protein-coupled receptors, the calcitonin receptor (CTR) and the calcitonin receptor like receptor (CRLR). Cloning and functional studies have shown that, CGRP, ADM, and amylin interact with different combinations of CTR or the CRLR and the receptor activity modifying protein (RAMP). It is believed that co-expression of RAMPs and either the CTR or CRLR is required to generate functional receptors for calcitonin, CGRP, ADM, and amylin. A specific receptor for AFP-6 has not been reported; however, binding studies indicate that AFP-6 binds to all the known receptors of the amylin family.

In general, amylin regulates gastric emptying, and suppress glucagon secretion and food intake, thus regulating the rate of glucose appearance in the circulation. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue. See, for example, U.S. Pat. Nos. 5,175,145, 5,677, 279, 5,405,831, 6114,304, and U.S. Pat. Application Publication Nos. 2002-0010133, 2003-0130177, 2004-0022807, and 2005-0197287.

The hormone calcitonin (CT) was named for its secretion in response to induced hypercalcemia and its rapid hypocalcemic effect. CT has an effect on plasma calcium levels and inhibits osteoclast function and is widely used for the treatment of osteoporosis. Therapeutically, salmon CT (sCT) appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptide discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake (Wimalawansa (1997) *Crit. Rev Neurobiol.* 11:167-239).

Adrenomedullin (ADM) is almost ubiquitously expressed with many more tissues containing the peptide than not. Hinson et al. (2000) *Endocrine Reviews* 21:138-167 details effects of ADM on the cardiovascular system, cellular growth, the central nervous system and the endocrine system, with a range of biological actions including vasodilation, cell growth, regulation of hormone secretion, and natriuresis.

Expression of AFP-6 (i.e., intermedin) is primarily in the pituitary and gastrointestinal tract. In in vivo studies, AFP-6 administration led to blood pressure reduction in both normal and spontaneously hypertensive rats and in vivo administration of AFP-6 in mice led to a suppression of gastric emptying and food intake (Roh et al. (2004) *J. Biol. Chem.* 279:7264-7274.)

It is estimated that about 64% of Americans are overweight or obese (roughly about 97 million adults) and it is generally believed that these numbers are increasing. Being obese or overweight may substantially increase the risk of morbidity from hypertension; dyslipidemia; type 2 diabetes; coronary heart disease; stroke; gallbladder disease; osteoarthritis; sleep apnea and respiratory problems; and endometrial, breast, prostate, and colon cancers. Higher body weights are also associated with increases in all-cause mortality. Furthermore, being obese or overweight may cause a person to have negative self-image about him or her self.

In humans, patients who are overweight or obese are considered those with a Body Mass Index (BMI) of equal or greater than 25. BMI is a common measure expressing the relationship (or ratio) of weight-to-height. It is a mathematical formula in which a person's body weight in kilograms is divided by the square of his or her height in meters (i.e., $wt/(ht)^2$). Individuals with a BMI of 25 to 29.9 are considered overweight, while individuals with a BMI of 30 to 39.9 are considered obese, and individuals with a BMI of 40 or more are considered morbidly obese. According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of overweight and obesity. These health risks increase even more as the severity of an individual's obesity increases.

For these reasons, there is an enormous interest in treating obesity. Existing therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery, such as gastric bypass. Jung et al. (1991) *Clinical Endocrinology* 35:11-20; Bray (1992) *Am. J. Clin. Nutr.* 55:538 S-544S.

In general, however, while loss of fat is desired, loss of lean body mass (protein) is not. Lean body mass is highly active metabolically and physiologically and the size is generally genetically defined and maintained. Lean body mass contains all the body protein. There is no real protein store as every protein molecule has a role in maintaining homeostasis. It is believed that loss of body protein is deleterious to the health of an individual. The majority of the protein in the lean body mass is in the skeletal muscle mass. Lean body mass is 50-60% muscle mass by weight, the rest is bone and tendon. Protein makes up the critical cell structure in muscle, viscera, red cells and connective tissue. Enzymes, which direct metabolism, and antibodies, which maintain immune function, are also proteins. Thus, it is desirable to prevent or minimize loss of lean body mass even while reducing body fat.

Caloric restriction, regardless of its form, can cause catabolism of body protein and produce negative nitrogen balance. Protein-supplemented diets, therefore, have gained popularity as a means of lessening nitrogen loss during caloric restriction. Protein-sparing modified fasting has been reported to be effective in weight reduction in adolescents. Lee et al. (1992) Clin. Pediatr. 31:234-236. However, these diets may produce only modest nitrogen sparing. A need exists for effective ways of promoting fat loss yet preserving lean body mass or minimizing its loss.

Eating is controlled by many factors, including appetite, food availability, family, peer, and cultural practices, and attempts at voluntary control. Dieting to a body weight leaner than needed for health is highly promoted by current fashion trends, sales campaigns for special foods, and in some activities and professions. Eating disorders involve serious disturbances in eating behavior, such as extreme and unhealthy reduction of food intake or severe overeating, as well as feelings of distress or extreme concern about body shape or weight. Researchers are investigating how and why initially voluntary behaviors, such as eating smaller or larger amounts of food than usual, at some point move beyond control in some people and develop into an eating disorder. Studies on the basic biology of appetite control and its alteration by prolonged overeating or starvation have uncovered enormous complexity, but in the long run have the potential to lead to new pharmacologic treatments for eating disorders.

The main types of eating disorders are anorexia nervosa and bulimia nervosa. A third type, binge-eating disorder, has been suggested but has not yet been approved as a formal psychiatric diagnosis. Eating disorders frequently develop during adolescence or early adulthood, but some reports indicate their onset can occur during childhood or later in adulthood. Eating disorders frequently co-occur with other psychiatric disorders such as depression, substance abuse, and anxiety disorders. In addition, people who suffer from eating disorders can experience a wide range of physical health complications, including serious heart conditions and kidney failure which may lead to death. Recognition of eating disorders as real and treatable diseases, therefore, is critically important.

There remains a need for effective methods and compositions for modifying body composition as well as controlling, preventing or treating obesity and eating disorders and associated conditions and disorders.

All patents, patent applications, and publications cited herein are hereby incorporated by reference in their entirety.

SUMMARY

In one aspect, methods provided include the use of amylin or an amylin agonist, including amylin analogs and amylin derivatives, in methods of controlling binge eating in a subject. In one embodiment, methods are provided for controlling binge eating, where the methods comprise administering, to a subject in need thereof, an amylin or amylin agonist in an amount effect to control or reduce binge eating by the subject. In one embodiment, methods are provided for controlling binge eating in a subject comprising administering an effective amount of amylin or an amylin agonist to the subject at times of the day when the subject is most likely to binge eat. In one embodiment, methods are provided for controlling binge eating in a subject further comprising administering to the subject at least one other drug that suppresses hunger at times of the day when the subject is not likely to binge eat. In some embodiments, the at least one other drug that suppresses hunger is sibutramine, orlistat, a PYY or PYY analog, a CB-1 antagonist such as rimonabant, a leptin or leptin analog, or phentermine. In some embodiments, the at least one other drug that suppresses hunger has a longer half-life in vivo than amylin.

In one embodiment, methods are provided for controlling binge eating, where the methods comprise administering, to a subject in need thereof, an amylin or amylin agonist in an amount effect to control or reduce binge eating by the subject in response to stressed conditions. In another embodiment, methods are provided for controlling binge eating, where the methods comprise administering, to a subject in need thereof, an amylin or amylin agonist in an amount effect to control or reduce binge eating by the subject not in response to stressed conditions.

In some embodiments in which a subject is in need of controlling binge eating, the controlling of binge eating includes a reduction in the frequency of binge eating episodes, a reduction in the duration of binge eating episodes, a reduction in the total amount consumed during a binge eating episode, a reduction in the difficulty in resisting the onset of a binge eating episode, or any combination thereof. In some embodiments in which a subject is in need of controlling binge eating, the subject eats large amounts of food when not physically hungry, subject eats food until uncomfortably full, the subject eats food when emotionally distressed, the subject has been diagnosed with an anxiety disorder such as obsessive-compulsive disorder, the said subject has been diagnosed as having impulse control problems, subject has been diagnosed as being a substance abuser such as a drug abuser or alcohol abuser, or any combination thereof.

In one aspect, methods provided include the use of amylin or an amylin agonist, including amylin analogs and amylin derivatives, for modifying food preferences of a subject. In one embodiment, methods are provided for modifying food preferences of a subject comprising administering, to a subject desirous of modifying food preferences, an amylin or an amylin agonist in an amount effective to modify the subject's food preferences as compared to the subject's food preferences in the absence of the administration.

In some embodiments, the modification of food preferences includes a decrease in the preference for high fat foods, a decrease in the intake of high fat foods, a decrease in the preference for sweet foods, a decrease in the intake of sweet foods, a decrease in the preference for chocolaty foods, a decrease in the intake of chocolaty foods, a decrease in the preference of savory foods, a decrease in the intake of savory foods, or any combination thereof. In some embodiments, the modification of food preferences includes an increase in the preference for low fat foods, an increase in the intake of low fat foods, or both.

In one embodiment, methods are provided for modifying food preferences of a subject comprising administering, to a subject desirous of modifying food preferences, an amylin or an amylin agonist in an amount effective to modify the subject's food preferences in response to stressed conditions. In one embodiment, methods are provided for modifying food preferences of a subject comprising administering, to a subject desirous of modifying food preferences, an amylin or an amylin agonist in an amount effective to modify the subject's food preferences not in response to stressed conditions.

In one aspect, methods provided include the use of amylin or an amylin agonist, including amylin analogs and amylin derivatives, for treating, reducing or preventing food cravings of a subject. In one embodiment, methods are provided for treating, reducing or preventing food cravings of a subject comprising administering to a subject an amylin or an amylin agonist in an amount effective to treat, reduce or prevent the subject's food cravings. In some embodiments, the subject craves sweets, chocolate, savory foods, salty foods, fatty foods, or any combination thereof. In some embodiments, the treating of food cravings of a subject includes a reduction in the frequency of cravings for particular foods, a reduction in the duration of cravings of particular foods, a reduction in the intensity of cravings for particular foods, a reduction in the difficulty in resisting cravings of particular foods, a reduction in the frequency of eating particular foods, or any combination thereof.

In one aspect, methods provided include the use of amylin or an amylin agonist, including amylin analogs and amylin derivatives, for reducing stress associated with decreased caloric intake in a subject. In one embodiment, methods are provided for reducing stress associated with decreased caloric intake of a subject comprising administering to the subject an amylin or an amylin agonist in an amount effective to reduce the subject's stress associated with decreased caloric intake. In one embodiment, the subject's stress associated with decreased caloric intake is manifest as depression.

In one aspect, methods provided include the use of amylin or an amylin agonist, including amylin analogs and amylin derivatives, for reducing stress caused by taking drugs that cause weight loss in a subject. In one embodiment, methods are provided for reducing stress caused by taking drugs that cause weight loss in a subject comprising administering to the subject an amylin or an amylin agonist in an amount effective to reduce the subject's stress caused by taking drugs that cause weight loss. In one embodiment, the subject's stress caused by taking drugs that cause weight loss is caused by drugs that target the brain such as sibutramine and rimonabant.

In one aspect, methods provided include the use of amylin or an amylin agonist, including amylin analogs and amylin derivatives, in methods of modulating the metabolic rate of a subject. In one embodiment, methods are provided for increasing the metabolic rate of a subject comprising administering to a subject an amylin or an amylin agonist in an amount effective to increase the subject's metabolic rate. In another embodiment, methods are provided for preserving the metabolic rate of a subject comprising administering to a subject an amylin or an amylin agonist in an amount effective to preserve the subject's metabolic rate. In another embodiment, methods are provided for reducing a decrease in the metabolic rate of a subject comprising administering to a subject an amylin or an amylin agonist in an amount effective to reduce a decrease the subject's metabolic rate. In some embodiments, such a decrease in the metabolic rate of a subject may be due to a reduced calorie diet, a restricted diet or weight loss.

In another embodiment, methods are provided for reducing at least one metabolic plateau in a subject comprising administering to a subject an amylin or an amylin agonist in an amount effective to reduce at least one metabolic plateau in the subject. In some embodiments, the reduction in a metabolic plateau is a reduction in the duration of the metabolic plateau, a reduction in the frequency of the metabolic plateau, a delay in the onset of a metabolic plateau, or any combination thereof.

In some embodiments in which the metabolic rate of a subject is modulated or a metabolic plateau is reduced in a subject, the metabolic rate in the subject is increased by at least about 5% compared to an otherwise identical subject over the same period of time under substantially similar or identical conditions and not administered amylin or amylin agonist.

In some embodiments in which the metabolic rate of a subject is modulated or a metabolic plateau is reduced in a subject, the subject is on a reduced calorie diet, is on a restricted diet, has lost weight, is losing weight, is initiating a reduced calorie diet or is initiating a restricted diet. In some embodiments in which the metabolic rate of a subject is modulated or a metabolic plateau is reduced in a subject, the subject's lean mass is not decreased or lean mass is increased with administration of the amylin or amylin agonist. In some embodiments, the subject is at risk of developing a reduced metabolic rate. In some embodiments in which the subject is initiating a reduce calorie diet or a restricted diet, administration of the amylin or amylin agonist is begun at the time of initiating or before the reduced calorie diet or restricted diet. In some embodiments in which the metabolic rate of a subject increased, the subject has been diagnosed with a psychiatric disorder such as borderline personality disorder or depression.

In another general aspect, methods provided include the use of amylin or an amylin agonist, including amylin analogs and amylin derivatives, for altering the fat composition or distribution in the subject. In one embodiment, methods are provided for decreasing fat mass in a subject by increasing their metabolic rate comprising administering to a subject an amylin or an amylin agonist in an amount effective to increase the subject's metabolic rate. In some embodiments in which the fat mass of a subject is decreased by an increase in metabolic rate, the subject's lean mass is not decreased, is maintained, or is increased with administration of the amylin or amylin agonist. In some embodiments in which the fat mass of a subject is decreased by an increase in metabolic rate, the fat mass is reduced as a percentage of total body mass, for example, by at least 1% of total body mass. In some embodiments in which the fat mass of a subject is decreased by an increase in metabolic rate, the subject is on a reduced calorie diet or a restricted diet.

In one embodiment, methods are provided for altering fat distribution in a subject comprising administering to a subject an amylin or an amylin agonist in an amount effective to alter the subject's fat distribution. In one embodiment, methods are provided for producing a more favorable fat distribution in a subject comprising administering to a subject an amylin or an amylin agonist in an amount effective to produce a more favorable fat distribution in the subject. In one embodiment, methods are provided for preventing or decreasing ectopic fat deposition in a subject comprising administering to a subject an amylin or an amylin agonist in an amount effective to prevent or decrease ectopic fat deposition in the subject. In another embodiment, methods are provided for reducing the amount of visceral fat in a subject comprising administering to a subject an amylin or an amylin agonist in an amount effective to reduce the amount of visceral fat in the subject.

In some embodiments in which fat distribution of a subject is altered, the method reduces the risk of the development of a metabolic disorder selected from the group consisting of polycystic ovary syndrome, metabolic syndrome, and cardiovascular disease. In some embodiments in which fat distribution of a subject is altered, the method results in a higher ratio of subcutaneous fat to visceral fat, compared to the subject at the time of amylin or amylin agonist administration. In some embodiments in which fat distribution of a subject is altered, the method results in a higher ratio of subcutaneous fat to ectopic fat. In some embodiments in which fat distribution of a subject is altered, the method results in a decrease of ectopic fat or a decrease in visceral fat or a combination thereof. In some embodiments in which fat distribution of a subject is altered, the method further results in an increase in lean body mass, for example, as the result of an increase in muscle cell mass. In some embodiments in which fat distribution of a subject is altered, visceral fat or ectopic fat or both is metabolized at a rate greater than that for subcutaneous fat.

In another aspect, methods provided include the use of amylin or an amylin agonist, including amylin analogs and amylin derivatives, for reducing weight in a morbidly obese subject. In one embodiment, methods are provided for reducing weight in a morbidly obese subject comprising reducing said subject's weight below morbidly obese and administering to the subject an amylin or an amylin agonist in an amount effective to further reduce the subject's weight. In one embodiment, the methods provided comprises initially reducing the subject's BMI to a level below 40 before administration of the amylin or amylin agonist. In some embodiments in which the weight of a morbidly obese subject is reduced, the morbidly obese subject has a body mass index of 40 or greater. In one embodiment, methods are provided for reducing weight in a subject with a BMI under 40 comprising administering to the subject an amylin or an amylin agonist in an amount effective to reduce the subject's weight.

In some embodiments in which the weight of a morbidly obese subject is reduced prior to administration of the amylin or amylin agonist, the subject's weight is reduced by reducing caloric intake, increasing physical activity, drug therapy, bariatric surgery, or any combination thereof. In one embodiment, the bariatric surgery is gastric bypass surgery. In some embodiments, the method further comprises administration of an effective amount of at least a second obesity-reducing agent, for example, sibutramine, orlistat, leptin, or rimonabant. In some embodiments, the amylin or amylin agonist is co-administered with the at least second obesity-reducing agent, either simultaneously or sequentially.

In another aspect, methods provided include administration to a subject an amylin or an amylin agonist, including amylin analogs and amylin derivatives, in a bolus dose one or more times a day for reducing weight in the subject. In some embodiments, the amylin or amylin agonist is co-administered with the at least one other drug known to cause weight loss, either simultaneously or sequentially. In some embodiments, the at least one other drug known to cause weight loss is administered is administered as a bolus dose or as a continuous dose.

In another aspect, methods provided include administration to a subject an amylin or an amylin agonist, including amylin analogs and amylin derivatives, in a continuous dose for reducing weight in the subject. In some embodiments, the amylin or amylin agonist is co-administered with the at least one other drug known to cause weight loss, either simultaneously or sequentially. In some embodiments, the at least one other drug known to cause weight loss is administered as a bolus dose or as a continuous dose.

In another aspect, methods provided include the use of an amylin or an amylin agonist, including amylin analogs and amylin derivatives, for treating bone loss in a subject who has had bariatric surgery. In one embodiment, methods are provided for reducing bone loss in a subject who has had bariatric surgery comprising administering to the subject an amylin or an amylin agonist in an amount effective to reduce bone loss in the subject. In some embodiments in which bone loss is treated with the amylin or the amylin agonist, the method further comprises administration of at least one other drug known to be effective for treating bone loss, for example, risedronate, alendronate, raloxifene, calcitonin, or teriparitide.

In another aspect, methods provided include the use of an amylin or an amylin agonist, including amylin analogs and amylin derivatives, for increasing thermogenesis in a subject. In one embodiment, methods are provided for increasing thermogenesis in a subject comprising administering to the subject an amylin or an amylin agonist in an amount effective to increase thermogenesis in the subject.

In another aspect, methods provided include the use of an amylin or an amylin agonist, including amylin analogs and amylin derivatives, for increasing oxidative metabolism in a subject. In one embodiment, methods are provided for increasing oxidative metabolism in a subject comprising administering to the subject an amylin or an amylin agonist in an amount effective to increase oxidative metabolism in the subject.

The present invention is also concerned with the control, treatment, and prevention of obesity, eating disorders, and related conditions, disorders and diseases, and the use of the amylin or amylin agonists and compositions of the present invention for manufacture of a medicament useful for treating these conditions.

BRIEF DESCRIPTION OF THE DRAWINGS

FIG. 1A depicts the average sucrose to chow ratio as a percentage of baseline, FIG. 1B depicts total chow consumption, FIG. 1C depicts average total kcals consumed, and FIG. 1D depicts average sucrose in kcals consumed.

FIGS. 10A and 10 B are graphs depicting effects on body weight of administration of vehicle or amylin for days 1-14 and only vehicle for days 15-28. FIG. 10A is a graph depicting an effect on body fat and FIG. 10B is a graph depicting an effect on body protein.

FIG. 16A is a graph depicting an effect on body fat and FIG. 16B is a graph depicting an effect on body protein.

FIG. 18A depicts the effect of administration of a CB-1 antagonist (1 mg/kg/day) and amylin (100 µg/kg/day), either alone or in combination, and FIG. 18B depicts the effect of administration of a CB-1 antagonist (3 mg/kg/day) and amylin (100 µg/kg/day), either alone or in combination.

DETAILED DESCRIPTION

Figure 1A:
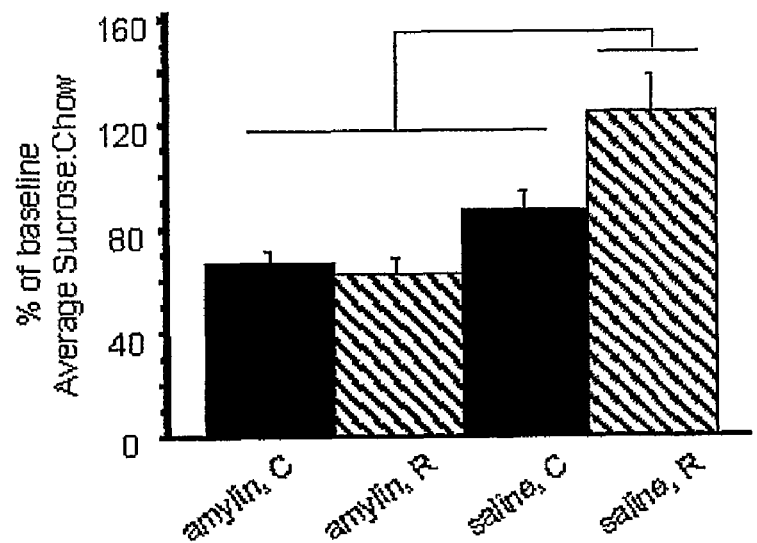
FIGS. 1A-1D are graphs depicting effects of amylin on feeding preferences under stressed and non-stressed conditions. In these graphs, R indicates animals subjected to restraint stress and C indicates control animals not subjected to restraint stress.

We have discovered a variety of methods and compositions useful in the control, treatment and prevention of obesity, eating disorders, and related conditions and disorders. In a one aspect, methods are provided for the reducing weight in a subject desirous of or in need thereof and the treatment or prevention conditions associated with weight loss, such as alteration of metabolic rates and thermogenesis. In another aspect, methods are provided for reducing weight in a morbidly obese subject, comprising administering an effective amount of amylin or amylin agonist. Also provided are methods for reducing bone loss associated with bariatric surgery. In another aspect, methods are provided for controlling, preventing or treating conditions or disorders associated with eating, such as binge eating, food cravings, and food-related stress disorders.

This disclosure also relates to the surprising discovery that amylin and amylin agonists are capable of modifying food preferences in subjects, both under stressed and non-stressed conditions. Accordingly, in another aspect, methods are provided for modifying food preferences. The modifications in food preferences include a change in the preferences for certain food types, a change in the amount of intake of certain foods types, a change in frequency of cravings, duration of cravings, intensity of cravings, difficulty in resisting cravings, and any combination thereof. In some embodiments, the food preferences include preferences for sweet foods, chocolaty foods, savory foods, and any combination thereof.

The methods described herein use the administration of amylin or amylin agonists for the control, prevention or treatment of such conditions and disorders.

While "obesity" is generally defined as a body mass index over 30, for purposes of this disclosure, any subject, including those with a body mass index of less than 30, who needs or wishes to reduce body weight or prevent body weight gain is included in the scope of "obese." Thus, subjects with a BMI of less than 30 and 25 and above (considered overweight) or below 25 are also included in the subjects of the invention. Morbid obesity refers to a BMI of 40 or greater. In one embodiment, a "subject in need thereof" is obese. Subjects who are insulin resistant, glucose intolerant, or have any form of diabetes mellitus (e.g., type 1, 2 or gestational diabetes) can benefit from this method. In another embodiment, the subject may be suffering from or be susceptible to a condition associated with eating such as binge eating or food cravings.

A "subject" may include any mammal, including humans. A "subject" may also include pets (e.g., dogs, cats, horses), as well as other animals (e.g., cows, sheep, pigs, goats). Subjects who may benefit from the methods disclosed herein may be overweight or obese; however, they may also be lean. Subjects who may benefit from the methods disclosed herein may be desirous of losing weigh or may have an eating disorder, such as binge eating, or an eating condition, such as food cravings. Subjects who may benefit from the methods disclosed herein may be desirous of modifying food preferences. They may have a metabolic disorder or condition in addition to these conditions. Exemplary metabolic disorders include diabetes, metabolic syndrome, insulin-resistance, and dyslipidemia. Subjects can be of any age. Accordingly, these disorders can be found in young adults and adults (defined herein as those aged 65 or under) as well as infants, children, adolescents, and the elderly (defined herein as over the age of 65). In fact, certain segments of the population may be particularly prone to having a particular condition, such as eating disorders in adolescents and young adults.

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to loose weight. For example, a person with a high metabolic rate may be able to expend more energy (the body burns more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, dual-energy x-ray absorptiometry (DEXA) scans, MRIs and CT scans. In one embodiment, fat mass and lean mass is measured using underwater weighing.

By "fat distribution" is meant the location of fat deposits in the body. Such locations of fat deposition include subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

As used herein, and as well-understood in the art, "treatment" is an approach for obtaining beneficial or desired results, including clinical results. "Treating" or "palliating" a disease, disorder, or condition means that the extent, undesirable clinical manifestations of a condition, or both, of a disorder or a disease state are lessened and/or time course of the progression is slowed or lengthened, as compared to not treating the disorder. For purposes of the methods disclosed herein, beneficial or desired clinical results include, but are not limited to, alleviation or amelioration of one or more symptoms, diminishment of extent of disorder, stabilized (i.e., not worsening) state of disorder, delay or slowing of disorder progression, amelioration or palliation of the disorder, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the singular form "a", "an", and "the" includes plural references unless otherwise indicated or clear from context. For example, as will be apparent from context, "an" amylin agonist can include one or more amylin agonists.

In one aspect, methods provided herein are used to increase the metabolic rate in a subject, decrease a reduction in the metabolic rate in a subject, or preserve the metabolic rate in a subject. In one embodiment, the metabolic rate may involve the preferential use of the body's fat as an energy source over lean body tissue. In one aspect, lean body mass is not decreased following administration of the amylin or amylin agonist. In another aspect, a reduction in the lean body mass is lessened or prevented following administration of the amylin or amylin agonist. In still another aspect, lean body mass is increased following administration of the amylin or amylin agonist. Such preference for fat as the energy source may be determined by comparing the amount of fatty tissue to lean body tissue, ascertained by measuring total body weight and fat content at the beginning and end of the treatment period. An increase in metabolic rate is a higher level of the use of calories or another energy source by a subject over a period of time compared with the level of use of calories or other energy source by the subject over another period of time under substantially similar or identical conditions without administration of an amylin or amylin agonist. In some embodiments, the metabolic rate of the subject is increased even though the caloric intake of the subject is decreased compared to that in the absence amylin or amylin agonist administration. The caloric intake may be decreased, for example, due to a reduced calorie diet, a restricted diet, or increased satiety or reduction in hunger compared to that in the absence amylin or amylin agonist administration. In one embodiment, the metabolic rate is increased at least about 5% in a subject, in other embodiments, the metabolic rate is increased at least about 10%, 15%, 20% 25%, 30%, or 35% in a subject compared with the level of use of calories or other energy source by the subject over another period of time under substantially similar or identical conditions without administration of an amylin or amylin agonist. The increase in metabolic rate is measured using a respiratory calorimeter. An effective amount of amylin or amylin agonist as used in this embodiment is an amount effective to increase the metabolic rate in a subject.

In another embodiment, a method is provided to reduce a decrease in metabolic rate in a subject. Such a decrease in metabolic rate can be the result of any condition or nutritional or physical regimen which leads to a reduction in metabolic rate, for example due to a reduced calorie diet, a restricted diet, or weight loss. A restricted diet includes allowances or prohibitions, or both on the types of food or the amounts of food or both permitted in a diet, not necessarily based on calories. For example, as an individual diets, the body compensates with a reduced metabolic rate based on the lower caloric intake. In essence, the body down-regulates the requirement for food, thereby subsisting on less food. As dieting continues, the threshold for caloric intake is reduced. When dieting has ended, the individual typically gains weight while eating a normal diet because of the lowered caloric intake threshold and lower-basal metabolic rate (NIH Technology Assessment Conference Panel (1992) *Ann. Intern. Med.* 116:942-949; Wadden (1993) *Ann. Intern. Med.* 119: 688-693). In one aspect, a method is provided to reduce the loss of metabolic rate in a subject, where the loss of metabolic rate is the result of a reduced calorie diet or weight loss. By using such a method, the subject's reduction in metabolic rate is decreased by at least about 10%, 15%, 20% 25%, 30%, 35%, 40%, 50%, 60%, 70%, 80%, 90%, or 95% in a subject. For such methods, it may be desirable to administer the amylin or amylin agonist at the time the condition or nutritional or physical regimen is initiated which leads to a loss or reduction in metabolic rate. However, it is also contemplated that amylin or amylin agonist administration is commenced before the condition or nutritional or physical regimen is initiated. In one instance, metabolic rate is measured using a respiratory calorimeter. An effective amount of amylin or amylin agonist as used in this embodiment is an amount effective to decrease the reduction of the metabolic rate in a subject.

In another aspect, methods for reducing metabolic plateaus are provided, where a method comprises administering an effective amount of an amylin or an amylin agonist to a subject. In a one embodiment, the subject is losing weight, or has lost weight, for example, due to a reduced calorie diet, increased exercise or a combination thereof. By "metabolic plateau" is meant time intervals of steady metabolic rate while the body adjusts to changes in caloric or energy input. Changes in caloric input or expenditure can be the result of, for example, reduced calorie diets or increased physical activity. Such plateaus can be observed, for example, during a weight loss regimen when weight loss slows or stops. In one embodiment, a method of the present invention reduces the duration of a metabolic plateau in a subject compared with the duration of metabolic plateaus in an otherwise identical subject over the same period of time under substantially similar or identical conditions without administration of the amylin or amylin agonist. In another embodiment, a method provided reduces the frequency of metabolic plateaus compared with the frequency of metabolic plateaus in an otherwise identical subject over the same period of time under substantially similar or identical conditions without administration of the amylin or amylin agonist. In still another embodiment, a method provided delays the onset of a metabolic plateau compared with the onset of a metabolic plateau in an otherwise identical subject over the same period of time under substantially similar or identical conditions without administration of the amylin or amylin agonist. In one embodiment, metabolic plateaus are identified by charting periods of reduced or no weight loss. In one embodiment, at least one metabolic plateau is reduced. In other embodiments, at least two, three, four, five, six, seven, eight, nine, or ten metabolic plateaus are reduced. In another aspect, metabolic plateaus are delayed one day as compared to a subject not administered amylin or amylin agonist under identical or similar conditions. In other aspects, metabolic plateaus are delayed 2 days, 3 days, 4 days, 5 days, 6 days, 1 week, 10 days, 2 weeks or 3 weeks in a subject.

In yet another embodiment, a method is provided to preserve the metabolic rate in a subject. In one embodiment, the subject may be at risk of losing metabolic rate, for example, due to the initiation of a reduced calorie diet, restricted diet, or anticipated weight loss. A preservation of metabolic rate is a maintenance of the level of the use of calories or another energy source by a subject over a period of time compared with the level of use of calories or other energy source by an otherwise identical subject over the same period of time under substantially similar or identical conditions without administration of the amylin or amylin agonist. In one aspect, the metabolic rate is maintained within 15% of the subject's metabolic rate prior to the initiation of the event that results in the decrease in metabolic rate. In other aspects, the metabolic rate is maintained within 10%, within 7%, within 5%, within 3% or less of the subject's metabolic rate. In one aspect, the amylin or amylin agonist is administered at the initiation of a reduced calorie diet, restricted diet, or exercise regimen.

Metabolic rates can be assessed using any method available for determining such rates, for example by using a respiratory calorimeter. Such methods and devices for assaying metabolic rates are known in the art and are described, for example, in U.S. Pat. Nos. 4,572,208, 4,856,531, 6,468,222, 6,616,615, 6,013,009, and 6,475,158. Alternatively, the metabolic rate of an animal can be assessed by measuring the amount of lean tissue versus fatty tissue catabolized by the animal following the diet period. Thus, total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In another aspect, methods for reducing fat mass by increasing the metabolic rate in a subject are provided, where the methods comprise administering an amylin or amylin agonist in an amount effective to reduce fat mass by increasing the subject's metabolic rate. Fat mass can be expressed as a percentage of the total body mass. In some aspects, the fat mass is reduced by at least 1%, at least 5%, at least 10%, at least 15%, at least 20%, or at least 25% over the course of treatment. In one aspect, the subject's lean mass is not decreased over the course of the treatment.

In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150 200, 250, 300, 400, 500, 600, 700, 800, 900, 1000 fewer calories per day.

In one embodiment, a method for altering the fat distribution in a subject is provided where the method comprises administering an amylin or amylin agonist to the subject in an amount effective to alter fat distribution in the subject. In one aspect, the alteration results from an increased metabolism of visceral fat or ectopic fat, or both in the subject. In some embodiments, the method involves the metabolism of visceral fat or ectopic fat or both at a rate of at least about 5%, 10%, 15%, 20%, 25%, 30%, 40%, or 50%, greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass.

In another embodiment, methods for reducing the amount of subcutaneous fat in a subject are provided, wherein the method comprises administering, to a subject in need thereof, an amylin or amylin agonist in an amount effective to reduce the amount of subcutaneous fat in the subject. In one embodiment, the amount of subcutaneous fat is reduced in a subject by at least about 5%. In other embodiments, the amount of subcutaneous fat is reduced by at least about 10%, 15%, 20%, 25%, 30% 40%, or 50% compared to the subject prior to administration of the amylin or amylin agonist.

The methods described herein can be used to reduce the amount of visceral fat in a subject. In one instance, the visceral fat is reduced in a subject by at least about 5%. In other instances, the visceral fat is reduced in a subject by at least about 10%, 15%, 20%, 25%, 30% 40%, or 50% compared to the subject prior to administration of the amylin or amylin agonist. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In one embodiment, a method for preventing the accumulation of ectopic fat or reducing the amount of ectopic fat in a subject is provided, wherein the method comprises administering, to a subject in need thereof, an amylin or amylin agonist in an amount effective to prevent accumulation of ectopic fat or to reduce the amount of ectopic fat in the subject. In one instance, the amount of ectopic fat is reduced in a subject by at least about 5% compared to the subject prior to administration of the amylin or amylin agonist. In other instances, the amount of ectopic fat is reduced by at least about 10%, 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods are provided for producing a more favorable fat distribution in a subject, where the method comprises administering to a subject an amylin or amylin agonist in an amount effective to produce a favorable fat distribution. In one embodiment, administration of an amylin or an amylin agonist reduces the amount of visceral fat or ectopic fat, or both, in a subject. In one embodiment, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combination thereof. In one embodiment, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

In still another aspect, methods provided include the use of a therapeutically effective amount of amylin or amylin agonists in combination with glucocortico steroids. Glucocortico steroids have the adverse effect of increasing fat mass and decreasing lean mass. Accordingly, it is contemplated that amylin or amylin agonist can be used in conjunction with glucocortico steroids under conditions where glucocortico steroid use is beneficial.

In another embodiment, methods for altering anthropometric parameters, e.g., waist circumference, hip circumference, waist-to-hip ratio) are provided. Waist circumference is a measure of abdominal obesity. In one embodiment, methods for reducing waist circumference of a subject are provided, wherein the method comprises administering, to a subject in need thereof, an amylin or amylin agonist in an amount effective to reduce the waist circumference of the subject. In one embodiment, the waist circumference of the subject is reduced by at least about 1%. In other embodiments, the waist circumference of the subject is reduced by at least about 2%, 3%, 4%, 5%, 6%, 7%, 8%. 9% or 10% compared to the subject prior to administration of the amylin or amylin agonist. In one embodiment, the waist circumference of the subject is reduced by at least about 1 cm. In other embodiments, the waist circumference of the subject is reduced by at least about 2 cm, 3 cm, 4 cm, 5 cm, or 6 cm compared to the subject prior to administration of the amylin or amylin agonist.

In another embodiment, methods for reducing hip circumference of a subject are provided, wherein the method comprises administering, to a subject in need thereof, an amylin or amylin agonist in an amount effective to reduce the hip circumference of the subject. In one embodiment, the hip circumference of the subject is reduced by at least about 1%. In other embodiments, the waist circumference of the subject is reduced by at least about 2%, 3%, 4%, 5%, or 6% compared to the subject prior to administration of the amylin or amylin agonist. In one embodiment, the waist circumference of the subject is reduced by at least about 1 cm. In other embodiments, the waist circumference of the subject is reduced by at least about 2 cm, 3 cm, 4 cm, 5 cm, or 6 cm compared to the subject prior to administration of the amylin or amylin agonist.

Also provided are methods to reduce weight in a morbidly obese subject by first reducing the subject's weight to a level below that of being morbidly obese, then administering an effective amount of amylin or amylin agonist to further reduce the subject's weight. Methods for reducing a subject's weight to being below that of morbid obesity include reducing caloric intake, increasing physical activity, drug therapy, bariatric surgery, such as gastric bypass surgery, or any combinations of the preceding methods. In one aspect, administering the amylin or amylin agonist further reduces the weight of the subject. In another embodiment, methods are provided for reducing the body mass index (BMI) in a subject having a BMI of 40 or less by administering an amylin or amylin agonist in an amount effective to further reduce the subject's weight.

In another aspect, methods for reducing the risk of developing metabolic disorders are provided, where the method comprises administering to the subject an amylin or amylin agonist in an amount effective to reduce the weight of a subject.

In another aspect, methods for controlling or modifying eating behaviors are provided, wherein the methods comprise administering, to a subject in need thereof, an amylin or amylin agonist in an amount effect to control or modify an eating behavior by the subject. In one embodiment, methods for controlling binge eating are provided, where the methods comprise administering, to a subject in need thereof, an amylin or amylin agonist in an amount effect to control or curb binge eating by the subject. In one embodiment, the amylin or amylin agonist is administered at times of the day when the subject is most likely to binge eat. In one aspect, binge eating is characterized by 1) eating, in a discrete period of time (e.g., within any 2-hour period), an amount of food that is definitely larger than most people would eat during a similar period of time and under similar circumstances and 2) a sense of lack of control over eating during the episode (e.g., a feeling that one cannot stop eating or control what or how much one is eating). In one embodiment, amylin agonists for use in controlling binge eating include agonists that have a longer half-life in vivo than amylin.

In one embodiment, methods for reducing binge eating are provided, where the methods comprise administering, to a subject in need thereof, an amylin or amylin agonist in an amount effect to reduce binge eating by the subject. The reduction of binge eating includes a reduction in the frequency of binge eating episodes, the duration of binge eating episodes, the total amount consumed during a binge eating episode, difficulty in resisting the onset of a binge eating episode, and any combination thereof, as compared to as compared to such frequency, duration, amount and resistance in the absence of administration of an amylin or amylin agonist. As such, by way of example, in one embodiment, a method may comprise a reduction in the frequency of binge eating episodes. In another embodiment, a method may comprise a reduction in the duration of binge eating episodes. In yet another embodiment, a method may comprise a reduction in the total amount consumed during a binge-eating episode. In yet another embodiment, a method may comprise a reduction in difficulty resisting the onset of a binge-eating episode.

In some embodiments, the binge eating is specifically binge eating of sweet foods, chocolaty foods, savory foods, high fat foods, or any combination thereof, under stressed or non-stressed conditions. In one embodiment, the binge eating is specifically binge eating of savory foods, including high fat foods. In one embodiment, the binge eating is specifically binge eating of sweet foods, both under stressed and non-stressed conditions.

Binge eating can be determined or measured using a questionnaire and a Binge Eating Scale (BES). Binge eating severity can be divided into three categories (mild, moderate, and severe) based on the total BES score (calculated by summing the scores for each individual item). Accordingly, methods are provided for reducing the BES score of a subject comprising administering to a subject in need thereof an amylin or an amylin agonist in an amount effective to reduce the BES score of the subject. In some embodiments, administration of an amylin or an amylin agonist changes the BES category of the subject, for example, from severe to moderate, from severe to mild, or from moderate to mild.

Some of the signs of binge eating include eating large amounts of food when not physically hungry, rapid eating, hiding of food because the person feels embarrassed about how much he or she is eating, eating until uncomfortably full, or any combination thereof. Many binge eaters are emotional eaters, i.e. their binge eating is triggered by their emotional state (e.g., some binge eaters eat when they are sad, some eat when they are happy, and some eat when they are under stress). A large number of binge eaters suffer from anxiety disorders, such as obsessive-compulsive disorder; impulse control problems; or personality disorders, such as borderline personality disorder or depression. In one embodiment, the binge eating is in response to stressed conditions. Other binge eaters are substance abusers, such as drug abusers or alcohol abusers. Not everyone who has a binge eating disorder is overweight, such as those binge eaters diagnosed with bulimia.

Subjects who binge eat often do so at particular times of the day, and thus treatment should be adjusted according to when the subject is most likely to binge eat. For example, if the subject binge eats mostly after 7 p.m. at night, the subject should be administered the amylin or amylin agonist at or shortly before 7 p.m. In one embodiment, the subject is administered the amylin or amylin agonist at the time they are susceptible to binge eating. In other embodiments, the subject is administered the amylin or amylin agonist at least about 15 minutes, at least about 30 minutes, at least about 45 minutes, at least about 1 hour, at least about 1 hour and 30 minutes, or at least about 2 hours before they are susceptible to binge eating.

An effective amount of amylin or an amylin agonist in this embodiment is an amount effective to curb or control the subject's desire to binge eat. Therefore, the effective amount of amylin or an amylin agonist will change dependent upon the subject and the level of their desire to binge eat. Furthermore, if a subject's desire to binge eat is less at one point in the day than at another, the dosage can be adjusted accordingly to provide a lower dose at the times of the day the subject has a lower desire to binge eat, and to provide a higher dose at the times of the day the subject has a higher desire to binge eat. In one embodiment, the subject is administered a peak dosage of amylin or amylin agonist at the time they have a high desire to binge eat. In other embodiments, the subject is administered a peak dosage of amylin or amylin agonist at least about 15 minutes, at least about 30 minutes, at least about 45 minutes, at least about 1 hour, at least about 1 hour and 30 minutes, or at least about 2 hours before they have a high desire to binge eat. In some embodiments, amylin or amylin agonist dosages are 25 μg to 240 μg, or may be higher or lower.

In certain methods of controlling binge eating and other eating behaviors, the amylin or amylin agonist is the only anti-obesity or weight reducing agent administered to the subject during the course of treatment.

In other methods of controlling binge eating, the subject may further be administered at least one other drug which is known to suppress hunger or control appetite. Such drugs include, but are not limited to, rimonabant, sibutramine, orlistat, exendin or an analog thereof, PYY or an analog thereof, CB-1, leptin and phentermine.

In another embodiment, methods for modifying food preferences in a subject are provided, wherein methods comprise administering, to a subject in need thereof, an amylin or amylin agonist in an amount effective to modify food preferences in the subject. As described herein, the methods of the invention include modification of food preferences under stressed conditions, as well as modification of food preferences under non-stressed conditions. In one embodiment, the food preferences include preferences for sweet foods, chocolaty foods, savory foods, high fat foods, low fat foods and any combination thereof. As such, by way of example, in one embodiment, a method is provided for modifying preferences for sweet foods in a subject, said method comprising administering an effective amount of an amylin or amylin agonist to a subject desirous of modifying preference for sweet foods, wherein said amount is effective to modify the subject's preference for sweet foods. In another embodiment, a method is provided for modifying preferences for chocolaty foods. In another embodiment, a method is provided for modifying preferences for savory foods. In another embodiment, a method is provided for modifying preferences for high fat foods. In another embodiment, a method is provided for modifying preferences for high low foods.

The modifications in food preferences may include a decrease in a preference for such foods, a decrease in the amount of intake of such foods, an enhancement of a preference of one food type over another food type, changes in frequency of cravings for such foods, duration of cravings for such foods, intensity of cravings for such foods, difficulty in resisting cravings for such foods, frequency of eating in response to cravings for such foods, and any combination thereof, as compared to such frequency, duration, intensity, or resistance in the absence of administration of an amylin or amylin agonist.

In yet another embodiment, a method may comprise reducing a subject's preference for sweet foods. In yet another embodiment, a method may comprise reducing a subject's preference for chocolaty foods. In yet another embodiment, a method may comprise reducing a subject's preference for savory foods. In yet another embodiment, a method may comprise reducing a subject's preference for high fat foods. In yet another embodiment, a method may comprise increasing a subject's preference for low fat foods. In yet another embodiment, a method may comprise enhancing a subject's preference for savory foods over sweet foods. In yet another embodiment, a method may comprise enhancing a subject's preference for savory foods over chocolaty foods. In yet another embodiment, a method may comprise enhancing a subject's preference for low fat foods over high fat foods.

In another embodiment, methods of treating, reducing, or preventing food cravings in a subject are provided, the methods comprising administering to the subject an amylin or an amylin agonist in an amount effective to treat, reduce or prevent food cravings in the subject. By food cravings it is intended to mean a subject's desire for a particular type of food. The most common food cravings include cravings for sugary foods, such as chocolate, and cravings for savory foods, such as salty snacks and fatty snacks. Food cravings can be measured by using a questionnaire, whether known in the art or created by the person studying the food cravings. Such a questionnaire would preferably rank the level of food cravings on a numerical scale, with the subject marking 0 if they have no food cravings, and marking (if on a scale of 1-10) 10 if the subject has severe food cravings. The questionnaire would preferably also include questions as to what types of food the subject is craving.

In one embodiment, a method may comprise reducing a subject's frequency of cravings for sweet foods, chocolaty foods, savory foods, high fat foods, etc. In another embodiment, a method may comprise reducing a subject's duration of cravings for sweet foods, chocolaty foods, savory foods, high fat foods, etc. In yet another embodiment, a method may comprise reducing a subject's intensity of cravings for sweet foods, chocolaty foods, savory foods, high fat foods, etc. In yet another embodiment, a method may comprise reducing a subject's difficulty in resisting cravings for sweet foods, chocolaty foods, savory foods, high fat foods, etc. In yet another embodiment, a method may comprise reducing a subject's frequency of eating in response to cravings for sweet foods, chocolaty foods, savory foods, high fat foods, etc. In yet another embodiment, a method may comprise reducing a subject's intake of sweet foods. In yet another embodiment, a method may comprise reducing a subject's intake of chocolaty foods. In yet another embodiment, a method may comprise reducing a subject's intake of savory foods. In yet another embodiment, a method may comprise reducing a subject's intake of high fat foods.

An effective amount of amylin or an amylin agonist for methods of treating food cravings is an amount effective to reduce a subjects desire for a particular type of food. Thus, the effective amount is different depending upon the subject being treated and the intensity of their desire for a particular food. For example, a person who is suffering from stress may crave sugary foods more than a person who is not, and therefore may require a higher dose of the amylin or amylin agonist. In addition, a person suffering from polycystic ovary syndrome may crave foods high in carbohydrates, and therefore may require a higher dose of the amylin or amylin agonist.

In another embodiment, methods of reducing stress associated with decreased caloric intake in a subject are provided, the methods comprising administering to a subject in need thereof an amylin or an amylin agonist in an amount effective to reduce stress associated with reduced caloric intake. By stress associated with decreased caloric intake it is intended to mean feelings of depression or anxiety brought on by a decrease in calories being consumed by the subject. By reducing stress it is intended to mean improving the subject's state of depression (by improving their overall sense of well being and mood) or reducing the subject's feeling of anxiety. An effective amount of amylin or an amylin agonist for methods of reducing stress associated with decreased caloric intake is an amount effective to improve one's depression (or sense of well being or mood) or an amount effective to reduce one's feeling of anxiety. Thus, the effective amount is different depending on the subject being treated and the intensity of their depression or anxiety caused by their decreased caloric intake.

By reducing weight it is meant that the subject loses a portion of his/her total body weight over the course of treatment (whether the course of treatment be days, weeks, months or years). Alternatively, reducing weight can be defined as a decrease in proportion of fat mass to lean mass (in other words, the subject has lost fat mass, but maintained or gained lean mass, without necessarily a corresponding loss in total body weight). An effective amount of amylin or amylin agonist administered in this embodiment is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, or by at least about 20%. Alternatively, the subject's percentage of fat mass is reduced, over the course of treatment, by at least 1%, at least 5%, at least 10%, at least 15%, at least 20%, or at least 25%.

In certain embodiments, methods are provided for reducing weight in a subject comprising administering to the subject an effective amount of amylin or an amylin agonist in a bolus dose one or more times a day. A bolus dose is an intermittent dosage of medicine (as opposed to a continuous infusion). A subject can be administered one or more bolus doses per day. The bolus dose can be the same no matter when it is administered to the subject, or can be adjusted such that the subject is administered a larger bolus dose at certain times of the day as compared to others. Administration of an amylin or amylin agonist in certain formulations, e.g., sustained release formulations, a bolus dose can be administered less frequently, for example, once every three days, once per week, twice a month, once every month. Furthermore, the time between bolus doses is preferably long enough to allow the drug administered in the previous bolus dose to clear the subject's blood stream. In some embodiments, amylin agonists having a longer half-life than amylin are administered.

In other embodiments, methods are provided for reducing weight in a subject comprising administering to the subject an effective amount of amylin or an amylin agonist in continuous doses. By continuous dose it is intended to mean the continuous infusion of the drug by, for example, intravenous injection or a transdermal patch. Alternatively, a continuous dose can be administered orally in the form of a controlled release capsule or tablet which releases the drug into the subjects system over a period of time. When administered by a continuous dose, the drug is released over a period of about 1 hour, more preferably the drug is released over a period of about 2, 3, 4, 5, 6, 7, 8, 9, 10, 11, 12, 18, or 24 hours.

In some embodiments, methods for reducing weight are provided wherein the amylin or amylin agonist is not co-administered with one other drug known to cause weight loss. In other embodiments, methods for reducing weight are provided wherein at least one other drug which is known to cause weight loss is co-administered to the subject with the amylin or amylin agonist. Such an other drug can have this weight loss effect by any of a number of means, including, but not limited to, suppressing hunger, controlling appetite, increasing metabolism, etc. In one embodiment, the at least one other drug known to cause weight loss is co-administered with the amylin or amylin agonist. By "co-administered" is meant that the amylin or amylin agonist is administered as a single administration with a second obesity-reducing compound, simultaneously as separate doses, or as sequentially administered. Sequential administration refers to administering the amylin or amylin agonist either before or after the second drug known to cause weight loss. In one aspect, the amylin or amylin agonist is administered about 30 minutes before or after the at least one other drug known to cause weight loss, more preferably about 1, 2, 3, 4, 5, 6, 7, 8, 9, 10, 11, or 12 hours before or after the at least one other drug known to cause weight loss. The at least one other drug known to cause weight loss can be administered as a bolus dose or as a continuous dose.

Amylin and amylin agonists reduce or protect against stress and its effects, and have anxiolytic, antidepressant, and antipsychotic effects, as described in commonly owned U.S. Pat. Application Nos. 60/667,335, and 60/760,583 and in PCT application PCT/US06/12601, filed 31 Mar. 2006, each of which are incorporated herein by reference.

In another embodiment, methods of reducing stress associated with taking drugs that cause weight loss are provided, the methods comprising administering to a subject in need thereof an amylin or an amylin agonist in an amount effective to reduce stress associated with taking drugs that cause weight loss. By stress associated with taking drugs that cause weight loss it is intended to mean feelings of depression or anxiety brought on by a decrease in calories being consumed by the subject. By reducing stress it is intended to mean improving ones state of depression (by improving their overall sense of well being and mood) or reducing ones feeling of anxiety.

Drugs on the market or under clinical investigation that control appetite by targeting the brain, such as rimonabant and sibutramine, can cause the subject taking them to have feelings of depression or anxiety. Rimonabant targets the endocannabinoid receptors in the brain, as well as receptors in adipose tissue, which are known to play a role in food cravings. Sibutramine is thought to work by increasing the activity of norepinephrine and serotonin in the brain. Amylin and amylin agonists improve the subject's feelings of depression or anxiety caused by the use of such drugs by improving the subject's depressive state and/or reducing the subject's anxiety level.

An effective amount of amylin or an amylin agonist for methods of reducing stress caused by taking drugs that cause weight loss is an amount effective to improve ones depression (or sense of well being or mood) or an amount effective to reduce ones feeling of anxiety. Thus, the effective amount is different depending on the subject being treated and the intensity of their depression or anxiety caused by their use of drugs that cause weight loss.

In another aspect, methods of reducing bone loss in a subject who has had bariatric surgery are provided, the methods comprising administering to a subject in need thereof an amylin or an amylin agonist in an amount effective to reduce bone loss in the subject. By bone loss it is intended to mean a reduction in bone density as compared to the subject's bone density pre-surgery. By reducing bone loss it is intended to mean preventing any bone loss or reducing the amount of bone loss as compared to a similar subject who had bariatric surgery but was not treated by the methods of the present invention. Bone loss may be measured by any know methods, including by using DEXA bone densitometry to measure bone density. Bariatric surgery includes, but is not limited to, The Sapala-Wood Micropouch roux-en-Y gastric bypass surgery, adjustable gastric banding, vertical banded gastroplasty, roux-en-Y gastric bypass, biliopancreatic diversion and duodenal switch.

An effective amount of amylin or an amylin agonist for methods of reducing bone loss in a subject who has had bariatric surgery is an amount effective to prevent or slow down bone resorption. In addition to amylin or an amylin agonist, the subject may be administered additional drugs known in the art to prevent or slow down bone loss. Such drugs include, but are not limited to, risedronate, alendronate, raloxifene, calcitonin, and teriparitide.

In another embodiment, methods of increasing thermogenesis in a subject are provided, the methods comprising administering to a subject in need thereof an amylin or an amylin agonist in an amount effective to increase thermogenesis in the subject. Thermogenesis is the process of liberating calories as heat by increasing the body's metabolic rate. Thermogenesis is activated by a few mechanisms, including supplements, nutrition, exercise, and exposure to cold.

In another embodiment, methods of increasing oxidative metabolism in a subject are provided, the methods comprising administering to a subject in need thereof an amylin or an amylin agonist in an amount effective to increase oxidative metabolism in the subject. Oxidative metabolism is the process by which oxygen is used to make energy from carbohydrates (sugars).

In another aspect, methods of inducing a feeling of fullness are provided, where the methods comprises administering, to a subject in need or desirous thereof, an amylin or an amylin agonist in an amount effective to induce a feeling of fullness or satiety in the subject. In one embodiment, methods are provided for inducing a feeling of fullness in a subject comprising administering, to a subject in need or desirous thereof, an amylin or an amylin agonist in an amount effective to induce a feeling of fullness or satiety in the subject after the subject has eaten less food than induced a feeling of fullness or satiety in the absence of the administration. In some embodiments, administration of an amylin or amylin agonist induces a feeling of fullness or satiety after the subject has eaten at least about 5% less food, at least about 10% less food, at least about 15% less food, at least about 20% less food, or at least about 25% less food.

In yet another aspect, a method of controlling hunger in a subject is provided, wherein the method comprises administering to a subject an amylin or an amylin agonist in an amount effective to control hunger in the subject.

In yet a further aspect, a method of prolonging a feeling of satiation in a subject is provided, wherein the method comprises administering to a subject an amylin or an amylin agonist in an amount effective to prolong a feeling of satiation in the subject.

In yet another aspect, a method of reducing, ameliorating, or preventing a subject's preoccupation with food is provided, wherein the method comprises administering to a subject an amylin or an amylin agonist in an amount effective to reduce, ameliorate, or prevent a preoccupation with food in the subject.

In a further aspect, a method of reducing caloric intake in a subject is provided, wherein the method comprises administering to a subject an amylin or an amylin agonist in an amount effective as a replacement for a meal or snack for the subject. In yet a further aspect, a method of reducing caloric intake by reducing the size of a meal is provided, wherein the method comprises administering an amylin or an amylin agonist to said subject in an amount effective to reduce the size of a meal ingested by the subject.

In another aspect, a method of controlling food intake is provided, wherein the method comprises administering to a subject an amylin or an amylin agonist in an amount effective to cause the subject to control or curb food intake. In yet another aspect, a method for ensuring or assisting in compliance with a reduced calorie or restrictive diet is provided, wherein the method comprises administering an effective amount of amylin or an amylin agonist to said subject. In another embodiment, a method of controlling caloric intake in a subject is provided, wherein the method comprises administering to the subject an effective amount of amylin or an amylin agonist at particular times of the day when the subject is more likely to overeat or to eat sweet or savory foods.

In a further aspect, a method of adjusting a subject's set point so that the body's propensity for homeostasis is adjusted to a healthier set point is provided, wherein the method comprises administering an effective amount of amylin or an amylin agonist to said subject. In another embodiment, a method of maintaining weight loss or maintaining the weight lost is provided, wherein the method comprises administering to a subject an amylin or an amylin agonist in an amount effective to maintain weight loss in the subject or the weight lost by the subject. In one embodiment, the weight loss is maintained by re-setting the subject's set point.

In another embodiment, methods of ameliorating, moderating, or preventing an adverse side effect of an obesity-reducing agent in a subject are provided, the methods comprising administering to the subject an amylin or an amylin agonist in an amount effective to ameliorate, moderate, or prevent an adverse side effect of an obesity-reducing agent taken by the subject. In another embodiment, methods of ameliorating, moderating, or preventing an adverse psychological side effect of an obesity-reducing agent in a subject are provided, the methods comprising administering to the subject an amylin or an amylin agonist in an amount effective to ameliorate, moderate, or prevent an adverse psychological side effect of an obesity-reducing agent.

In another embodiment, methods of ameliorating, moderating, or preventing an adverse gastrointestinal side effect of an obesity-reducing agent in a subject are provided, the methods comprising administering to the subject an amylin or an amylin agonist in an amount effective to ameliorate, moderate, or prevent an adverse gastrointestinal side effect of an obesity-reducing agent taken by the subject. In such an embodiment, amylin or an amylin agonist has a gastroprotective effect.

Furthermore, in any of the aspects of the invention described herein where the amylin or amylin agonist is co-administered with at least one other obesity reducing (or anti-obesity) or weight reducing drug, the use of amylin or an amylin agonist in combination with the at least one other obesity reducing (or anti-obesity) or weight reducing drug results in a synergistic effect.

In embodiments described herein where the amylin or amylin agonist is co-administered with at least one other obesity reducing (or anti-obesity) or weight reducing drug, the use of amylin or an amylin agonist in combination with the at least one other obesity reducing (or anti-obesity) or weight reducing drug results in a lower dosage requirement for at least one of the compounds, with the same effect.

In another aspect, it is also possible to combine an amylin or amylin agonist useful in the methods described herein, with one or more other active ingredients useful in the control, prevention, or treatment of obesity or eating disorders or conditions. For example, in one embodiment, methods are provided for reducing the BMI of a subject having a BMI of 40 or less by administering an amylin or an amylin agonist in combination with at least a second obesity-reducing agent in amounts effective to reduce the BMI of the subject. Such second obesity-reducing compounds include sibutramine, orlistat, leptin and rimonabant. For example, amylin or amylin agonist may be combined with one or more other compounds, in a unitary dosage form, or in separate dosage forms intended for simultaneous or sequential administration to a subject in need. In one embodiment, the amylin or amylin agonist is co-administered with the second obesity-reducing compound, e.g., as a single administration with a second obesity reducing compound, simultaneously as separate doses, or as sequentially administered where the administration of the compounds may be separated in time by seconds, minutes, or hours. Sequential administration may also include administration of a first course of an obesity reducing, e.g., an amylin or an amylin agonist, followed by at least one course of another obesity reducing agent. The treatment courses may or may not overlap.

When administered sequentially, the combination may be administered in two or more administrations. In an alternative embodiment, it is possible to administer one or more amylin or amylin agonist and one or more additional active ingredients by different routes. The skilled artisan will also recognize that a variety of active ingredients may be administered in combination with amylin or amylin agonist that may act to augment or synergistically enhance the control prevention, amelioration, attenuation, or treatment of obesity or eating disorders or conditions.

According to the methods provided herein, when co-administered with at least one other obesity reducing (or anti-obesity) or weight reducing drug, an amylin or amylin agonist may be: (1) co-formulated and administered or delivered simultaneously in a combined formulation; (2) delivered by alternation or in parallel as separate formulations; or (3) by any other combination therapy regimen known in the art. When delivered in alternation therapy, the methods provided may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments, compounds provided herein may be used with other commercially available diet aids or other anti-obesity agents, such as, by way of example, PYY and PYY agonists, GLP-1 and GLP-1 agonists, a DPPIV inhibitor, CCK and CCK agonists, exendin and exendin agonists, GIP and GIP agonists, and leptin and leptin agonists. Additional anti-obesity agents for use in the methods provided that are in current development are also of interest in the methods of the present invention. Other anti-obesity agents include phentermine, fenfluramine, sibutramine, rimonabant, and orlistat.

As such, in one aspect, the amylin or amylin agonists may be used as part of a combination therapy for the control, prevention or treatment of obesity or eating disorders or conditions. Preferred compounds used as part of a combination therapy to treat obesity or reduce weight include, but are not limited to, central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), some dopamine antagonists, and cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, α-melanocyte-stimulating hormone analogues, melanocoritin-4 receptor agonists, and agents that affect insulin metabolism/activity, which include protein-tyrosine phosphatase-1B inhibitors, peroxisome proliferator activated receptor-γ receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, liraglutide, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/ indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion.

Other preferred compounds include ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-113715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1/D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; β-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPY5RA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; H3 histamine antagonists; PPARpan agonists; EP-01492; hormone-sensitive lipase inhibitors; fatty acid-binding protein 4 inhibitors; thiolactone derivatives; protein tyrosine phosphatase 1B inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; neuropeptide Y antagonist; angiogenesis inhibitors; G protein-coupled receptor agonists; nicotinic therapeutics (ChemGenex); anti-obesity agents (Abbott); neuropeptide Y modulators; melanin concentrating hormone; GW-594884A; MC-4R agonist; histamine H3 antagonists; orphan GPCR modulators; MITO-3108; NLC-002; HE-2300; IGF/IBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; neuropeptide Y1 antagonist; beta-3 adrenoceptor agonists; ob gene products (Eli Lilly & Co.); SWR-0342-SA; beta-3 adrenoceptor agonist; SWR-0335; SP-18904; oral insulin mimetics; beta 3 adrenoceptor agonists; NPY-1 antagonists; β-3 agonists; obesity therapeutics (7TM Pharma); 11beta-hydroxysteroid dehydrogenase (HSD)1 inhibitors; QRX-431; E-6776; RI-450; melanocortin-4 antagonists; melanocortin 4 receotr agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; NPY-1 antagonists; A-71378; ®-didesmethylsibutramine; amide derivatives; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BIBP-3226; HP-228; talibegron; FR-165914; AZM-008; AZM-016; AZM-120; AZM-090; vomeropherin; BMS-187257; D-3800; AZM-131; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; AZM-134; AZM-127; AZM-083; AZM-132; AZM-115; exopipam; SSR-125180; obesity therapeutics (Melacure Therapeutics AB); BRL-35135; SR-146131; P-57; AZM-140; CGP-71583A; RF-1051; BMS-196085; manifaxine; beta-3 agonists; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; metformin; AOD-9604; ATL-062; BVT-933; GT389-255; SLV319; HE-2500; PEG-axokine; L-796568; and ABT-239.

In some embodiments, compounds for use in combination with an amylin or amylin agonist include rimonabant, sibutramine, orlistat, PYY or an analog thereof, CB-1 antagonist, leptin, phentermine, and exendin analogs. Exemplary dosing ranges include phentermine resin (30 mg in the morning), fenfluramine hydrochloride (20 mg three times a day), and a combination of phentermine resin (15 mg in the morning) and fenfluramine hydrochloride (30 mg before the evening meal), and sibutramine (10-20 mg). Weintraub et al. (1984) Arch. Intern. Med. 144:1143-1148.

In other embodiments, the methods provided comprise administration of an amylin or an amylin agonist in combination with at least one other anti-obesity agent with the proviso that the at least one other anti-obesity agent is not an NPY1 receptor antagonist, an NPY5 receptor antagonist, an NPY2 receptor agonist, an NPY4 receptor agonist, a leptin, a leptin derivative, a leptin agonist, a CNTF, a CNTF agonist/ modulator, a CNTF derivative, a MCH1R antagonist, a MCH2R antagonist, a melanocortin 4 agonist, a MC4 receptor agonist, a cannabinoid receptor (CB-1) antagonist/inverse agonist, a ghrelin antagonist, a 5HT2c agonist, a serotonin reuptake inhibitor, a serotonin transport inhibitor, an exendin, an exendin derivative, an exendin agonist, a GLP-1, a GLP-1 analog, a GLP-1 agonist, a DPP-IV inhibitor, an opioid antagonist, an orexin antagonist, a metabotropic glutamate subtype 5 receptor antagonist, a histamine 3 antagonist/inverse agonist, or topiramate. In certain embodiments, the methods provided comprise administration of an amylin or an amylin agonist in combination with at least one other anti-obesity agent with the proviso that the at least one other anti-obesity agent is not phentermine, rimonabant, or sibutramine.

Amylin and amylin agonists may also be administered with compounds useful for treating metabolic syndrome, such as glucose-dependent insulinotropic polypeptide (GIP) analogs. In other embodiments, compounds provided herein may be used with other analgesics, immune suppressors, or other anti-inflammatory agents.

Compounds useful in the context of the methods disclosed herein include amylin and amylin agonists. Generally, amylin and amylin agonists include amylin family peptide hormones such as amylin, adrenomedullin ("ADM"), calcitonin ("CT"), calcitonin gene related peptide ("CGRP"), intermedin (also known as "AFP-6") and related peptides. Native amylin family peptide hormones are known in art, as are agonist peptide analogs and derivatives. Certain native peptides, agonist peptide analogs and derivatives are described herein, however it should be recognized that any known amylin family peptides having the properties described herein may be used in conjunction with the method disclosed herein.

As will be recognized by those skilled in the art, amylin family peptide hormones are generally C-terminally amidated when expressed physiologically, but need not be for the purposes of the methods and compositions provided herein. In other words, the C-terminus of these peptide may have a free —OH or —NH$_2$ group. As described herein, these peptides may also have other post-translational modifications.

By "amylin" is meant the human peptide hormone referred to as amylin and secreted from the beta cells of the pancreas, and species variations thereof, examples of which are described in U.S. Pat. No. 5,234,906, the contents of which are hereby incorporated by reference. More particularly, amylin is a 37-amino acid polypeptide hormone normally co-secreted with insulin by pancreatic beta cells in response to nutrient intake (see, e.g., Koda et al. (1992) *Lancet* 339: 1179-1180). In this sense, "amylin," "wild-type amylin," and "native amylin," i.e., unmodified amylin, are used interchangeably. Amylin is also sometimes referred to as "IAPP."

By "agonist" is meant a compound which elicits a biological activity of amylin, for example, having a potency better than amylin, or within five orders of magnitude (plus or minus) of potency compared to amylin, for example 4, 3, 2, or 1 order of magnitude, when evaluated by art-known measures such as, for example, receptor binding/competition studies as described herein. For example, amylin agonists may have 3, 5, 10, 50, 100, 500, 1000 times or more activity than native amylin. Alternatively, agonists, for example, may have anywhere from 2, 5, 10, 15, or 20 times less activity than native amylin.

In one embodiment, the term agonist refers to a compound which elicits a biological effect similar to that of native amylin, for example a compound (1) having activity in modifying food preferences as described herein similar to a native human reference peptide, and/or (2) having activity in altering metabolic rates as described herein similar to a native human reference peptide. In one embodiment, the term agonist refers to a compound which elicits a biological effect similar to that of native amylin, for example a compound having activity in controlling, preventing or treating obesity or an eating disorder or condition as described herein similar to a native human reference peptide. In one embodiment, the term agonist refers to a compound which elicits a biological effect similar to that of native amylin, for example a compound (I) having activity in a food intake, gastric emptying, pancreatic secretion, or weight loss assay (PCT Application No. PCT/US2005/004631, filed on Feb. 11, 2005, and incorporated by reference) similar to the native human reference peptide, and/or (2) which binds specifically in a reference receptor assay or in a competitive binding assay with amylin. In one embodiment, the agonists will bind in such assays with an affinity of better than 1 µM, and, in another embodiment, with an affinity of better than 1-5 nM. Such agonists may comprise a polypeptide comprising an active fragment of amylin or a small chemical molecule. In some embodiments, an agonist is a peptide, not a small chemical molecule. It is, however, contemplated that in certain embodiments, salmon calcitonin, calcitonin, CGRP, ADM, AFP-6, and/or their respective analogs may be excluded from the scope of amylin agonist with proviso language. In certain embodiments, an amylin agonist is not a small chemical molecule and small chemical molecules may be excluded from the scope of amylin agonist with proviso language.

By "analog" is meant a peptide whose sequence is derived from that of amylin including insertions, substitutions, extensions, and/or deletions, having at least some amino acid identity to amylin or region of an amylin peptide. Analogs may have at least 50 or 55% amino acid sequence identity with a native amylin, or at least 70%, 80%, 90%, or 95% amino acid sequence identity with a native amylin. In one embodiment, such analogs may comprise conservative or non-conservative amino acid substitutions (including non-natural amino acids and L and D forms). Analogs include compounds having agonist and compounds having antagonist activity. Amylin agonist analogs are analogs as herein described and function as an amylin agonist. Analogs, as herein defined, also include derivatives.

A "derivative" is defined as a molecule having the amino acid sequence of a native amylin or analog, but additionally having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

In general, with respect to an amino acid sequence, the term "modification" includes substitutions, insertions, elongations, deletions, and derivatizations alone or in combination. In some embodiments, the peptides may include one or more modifications of a "non-essential" amino acid residue. In this context, a "non-essential" amino acid residue is a residue that can be altered, e.g., deleted or substituted, in the novel amino acid sequence without abolishing or substantially reducing the activity (e.g., the agonist activity) of the peptide (e.g., the analog peptide). In some embodiments, the peptides may include one or more modifications of an "essential" amino acid residue. In this context, an "essential" amino acid residue is a residue that when altered, e.g., deleted or substituted, in the novel amino acid sequence the activity of the reference peptide is substantially reduced or abolished. In such embodiments where an essential amino acid residue is altered, the modified peptide may possess an activity of amylin of use in the methods provided. The substitutions, insertions and deletions may be at the N-terminal or C-terminal end, or may be at internal portions of the component peptide hormone. By way of example, the peptide may include 1, 2, 3, 4, 5, 6, 7, 8, 9, 10, or more substitutions, both in a consecutive manner or spaced throughout the peptide molecule. Alone or in combination with the substitutions, the peptide may include 1, 2, 3, 4, 5, 6, 7, 8, 9, 10, or more insertions, again either in consecutive manner or spaced throughout the peptide molecule. The peptide, alone or in combination with the substitutions and/or insertions, may also include 1, 2, 3, 4, 5, 6, 7, 8, 9, 10, or more deletions, again either in consecutive manner or spaced throughout the peptide molecule. The peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or normatural (unnatural). Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

By "amino acid" or "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, pyroglutamate, and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al. (1998) *J. Med. Chem.* 41:2481-2491.

It should be noted that alternatives are written throughout in Markush groups, for example, each amino acid position that contains more than one possible amino acid. It is specifically contemplated that each member of the Markush group should be considered separately, thereby comprising another embodiment, and the Markush group is not to be read as a single unit.

"Sequence identity", as is well understood in the art, is a relationship between two or more polypeptide sequences or two or more polynucleotide sequences, as determined by comparing the sequences. In the art, "identity" can also mean the degree of sequence relatedness between polypeptide or polynucleotide sequences, as determined by the match between strings of such sequences. Identity can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); Sequence Analysis in *Molecular Biology*, von Heinje, G., Academic Press (1987); Sequence *Analysis Primer*, Gribskov, M. and Devereux, J., eds., Stockton Press, New York (1991); and Carillo, H., and Lipman, D., *SIAM J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux et al. (1984) *Nucleic Acids Research* 12:387; suite of five BLAST programs, three designed for nucleotide sequences queries (BLASTN, BLASTX, and TBLASTX) and two designed for protein sequence queries (BLASTP and TBLASTN) (Coulson (1994) *Trends in Biotechnology* 12:76-80; Birren et al. (1997) *Genome Analysis* 1:543-559). The BLAST X program is publicly available from NCBI and other sources (*BLAST Manual*, Altschul, S., et al., NCBI NLM NIH, Bethesda, Md. 20894; Altschul et al. (1990) *J. Mol. Biol.* 215:403-410). The well known Smith Waterman algorithm can also be used to determine identity.

Parameters for polypeptide sequence comparison typically include the following: Algorithm: Needleman and Wunsch (1970) *J. Mol. Biol.* 48:443-453; Comparison matrix: BLOSUM62 from Hentikoff and Hentikoff (1992) *Proc. Natl. Acad. Sci. USA* 89:10915-10919; Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons. In one embodiment the BLASTP program of NCBI is used with the default parameters of no compositional adjustment, expect value of 10, word size of 3, BLOSUM62 matrix, gap extension cost of 11, end gap extension cost of 1, dropoff (X) for blast extension (in bits) 7, X dropoff value for gapped alignment (in bits) 15, and final X dropoff value for gapped alignment (in bits) 25.

Parameters for nucleic acid molecule sequence comparison include the following: Algorithm: Needleman and Wunsch (1970) *J. Mol. Bio.* 48:443-453; Comparison matrix: matches—+10; mismatches=0; Gap Penalty: 50; Gap Length Penalty: 3. As used herein, "% identity" is determined using the above parameters as the default parameters for nucleic acid molecule sequence comparisons and the "gap" program from GCG, version 10.2.

Throughout this disclosure, the amino acid sequences may be referred to as amino acids at position a to position b adjacent to a reference peptide. For example, 1-7 hAmylin refers to the amino acid sequence from position 1 to position 7, inclusive, of human amylin (SEQ ID NO:1), the reference peptide in this example. Modification to the reference peptide may be shown as the position of modification adjacent to the modification. For example, (2Asp 7Lys) 1-7 hAmylin represents the amino acid sequence at positions 1 to 7 of human amylin with a modification of the Cys to Asp at position 2 and a modification of the Cys to Lys at position 7. For another example, $^{18}$Arg$^{25,28}$Pro-h-amylin represents the amino acid sequence of human amylin with a modification of the His to Arg at position 18, a modification of the Ala to Pro at position 25, and a modification of the Ser to Pro at position 28.

Human amylin (hAmylin or h-amylin) has the following amino acid sequence: Lys-Cys-Asn-Thr-Ala-Thr-Cys-Ala-Thr-Gln Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). Rat amylin (rAmylin) has the following sequence: KCNTATCATQRLANFLVRSSNNLG-PVLPPTNVGSNTY (SEQ ID NO:2). The use of amylins from any species is contemplated.

Amylin agonists contemplated in the use in the methods disclosed herein include those described in U.S. Pat. Nos. 5,686,411, 6,114,304, and 6,410,511, and PCT Application Publication No. WO 93/10146, the contents of which are herein incorporated by reference in their entirety. Such compounds include those having formula I:

(SEQ ID NO: 3)
$^1$A$_1$-X-Asn-Thr-$^5$Ala-Thr-Y-Ala-Thr-$^{10}$Gln-Arg-Leu-B$_1$-

Asn-$^{15}$Phe-Leu-C$_1$-D$_1$-E$_1$-$^{20}$F$_1$-G$_1$-Asn-H$_1$-Gly-$^{25}$I$_1$-J$_1$-

Leu-K$_1$-L$_1$-$^{30}$Thr-M$_1$-Val-Gly-Ser-$^{35}$Asn-Thr-Tyr wherein A$_1$ is Lys, Ala, Ser or hydrogen;
B$_1$ is Ala, Ser or Thr;
C$_1$ is Val, Leu or Ile;
D$_1$ is His or Arg;
E$_1$ is Ser or Thr;
F$_1$ is Ser, Thr, Gln or Asn;
G$_1$ is Asn, Gln or His;
H$_1$ is Phe, Leu or Tyr;
I$_1$ is Ala or Pro;
J$_1$ is Ile, Val, Ala or Leu;
K$_1$ is Ser, Pro, Leu, Ile or Thr;
L$_1$ is Ser, Pro or Thr;
M$_1$ is Asn, Asp, or Gln;
X and Y are independently selected amino acid residues having side chains which are chemically bonded to each other to form an intramolecular linkage.

The C-terminal portion can be amino, alkylamino, dialkylamino, cycloalkylamino, arylamino, aralkylamino, alkyloxy, aryloxy, aralkyloxy or carboxyl. Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Exemplary alkyl chains include lower alkyl groups having from about 1 to about 6 carbon atoms.

An additional aspect, compositions and methods of use provided herein are directed to agonist analogues of SEQ ID NO:3 which are not bridged, and wherein X and Y are independently selected from Ala, Ser, Cys, Val, Leu and Ile or alkyl, aryl, or aralkyl esters and ethers of Ser or Cys.

Exemplary compounds include, but are not limited to des-$^1$Lys-h-amylin (SEQ ID NO:4), 28Pro-h-amylin (SEQ ID NO:5), $^{25,28,29}$Pro-h-amylin (SEQ ID NO:6), $^{18}$Arg$^{25,28}$Pro-h-amylin (SEQ ID NO:7), and des-$^1$Lys Arg$^{25,28}$Pro-h-amylin (SEQ ID NO:8), which all show amylin activity in vivo in treated test animals, (e.g., provoking marked hyperlactemia followed by hyperglycemia). In addition to having activities characteristic of amylin, certain of the compounds provided herein have also been found to possess more desirable solubility and stability characteristics when compared to human amylin. Examples of these compounds include $^{25}$Pro$^{26}$Val$^{28,29}$Pro-h-amylin (SEQ ID NO:9), $^{25,28,29}$Pro-h-amylin, and $^{18}$Arg$^{25,28}$Pro-h-amylin.

Other compounds include $^{18}$Arg$^{25,28,29}$Pro-h-amylin (SEQ ID NO:10), des-$^1$Lys$^{18}$Arg$^{25,28,29}$Pro-h-amylin (SEQ ID NO:11), des-$^1$Lys$^{25,28,29}$Pro-h-amylin (SEQ ID NO:12), $^{25}$Pro$^{26}$Val$^{28,29}$Pro-h-amylin (SEQ ID NO:13), $^{23}$Leu$^{25}$Pro$^{26}$Val$^{28,29}$Pro-h-amylin (SEQ ID NO:14), $^{23}$Leu$^{25}$Pro$^{26}$Val$^{28}$Pro-h-amylin (SEQ ID NO:15), des-$^1$Lys$^{23}$Leu$^{21}$Pro$^{26}$Val$^{28}$Pro-h-amylin (SEQ ID NO:16), $^{18}$Arg$^{23}$Leu$^{25}$Pro$^{26}$Val$^{28}$Pro-h-amylin (SEQ ID NO:17), $^{18}$Arg$^{23}$Leu$^{25,28,29}$Pro-h-amylin (SEQ ID NO:18), $^{18}$Arg$^{23}$Leu$^{25,28}$Pro-h-amylin (SEQ ID NO:19), $^{17}$Ile$^{23}$Leu$^{25,28,29}$Pro-h-amylin (SEQ ID NO:20), $^{17}$Ile$^{25,28,29}$Pro-h-amylin (SEQ ID NO:21), des-$^1$Lys$^{17}$Ile$^{25,28,29}$Pro-h-amylin (SEQ ID NO:22), $^{17}$Ile$^{18}$Arg$^{23}$Leu-h-amylin (SEQ ID NO:23), $^{17}$Ile$^{18}$Arg$^{23}$Leu$^{26}$Val$^{29}$Pro-h-amylin (SEQ ID NO:24), $^{17}$Ile$^{18}$Arg$^{23}$Leu$^{25}$Pro$^{26}$Val$^{28,29}$Pro-h-amylin (SEQ ID NO:25), $^{13}$Thr$^{21}$His$^{23}$Leu$^{26}$Ala$^{28}$Leu$^{29}$Pro$^{31}$Asp-h-amylin (SEQ ID NO:26), $^{13}$Thr$^{21}$His$^{23}$Leu$^{26}$Ala$^{29}$Pro$^{31}$Asp-h-amylin (SEQ ID NO:27), des-$^1$Lys$^{13}$Thr$^{21}$His$^{23}$Leu$^{26}$Ala$^{29}$Pro$^{31}$Asp-h-amylin (SEQ ID NO:28), $^{13}$Thr Arg$^{21}$His$^{23}$Leu$^{26}$Ala$^{29}$Pro$^{31}$Asp-h-amylin (SEQ ID NO:29), $^{13}$Thr$^{18}$Arg$^{21}$His$^{23}$Leu$^{28,29}$Pro$^{31}$Asp-h-amylin (SEQ ID NO:30), and $^{13}$Thr$^{18}$Arg$^{21}$His$^{23}$Leu$^{25}$Pro$^{26}$Ala$^{28,29}$Pro$^{31}$Asp-h-amylin (SEQ ID NO:31).

Amylin agonists contemplated in the use in the methods disclosed herein include intermedin or AFP-6 peptides. By "intermedin" or "AFP-6" is meant the human peptide hormone and species variants thereof, in any physiological form. Native AFP-6 peptides are known in the art, as are functional AFP-6 peptide analogs, derivatives, and hybrids. Any AFP-6 peptide, analog, or derivative known in the art that exhibits biological activity known in the art may be used in conjunction with the compositions and methods disclosed herein. In one embodiment, the AFP-6 peptides, analogs, and derivatives have at least one hormonal activity of native AFP-6. In certain embodiments, the AFP-6 peptides, analogs, derivatives, and hybrids are agonists of a receptor which native AFP-6 is capable of specifically binding.

Amylin agonists contemplated in the use in the methods disclosed herein include AFP-6 analogs as described in U.S. Provisional Application No. 60/617,468 and PCT Application No. PCT/US05/036456, which are herein incorporated by reference in their entirety. A mature AFP-6 peptide, also known as intermedin, has the following amino acid sequence

TQAQLLRVGCVLGTCQVQNLSHRLWQLMGPAGRQDSAPVDPSSPHSY. (SEQ ID NO: 32)

The AFP-6 or AFP-6 analogs may or may not be amidated at the C-terminal end. Such AFP-6 analogs include those having formula II: $X_1$-$X_2$-$X_3$-$X_4$-$X_5$-$X_6$-$X_7$-$X_8$-QVQNLSHRL-WQL-$X_{21}$-$X_{22}$-$X_{23}$-$X_{24}$-$X_{25}$-$X_{26}$-$X_{27}$-$X_{28}$-SAPV-$X_{33}$-PSSPHSY (SEQ ID NO:33) wherein $X_1$ is absent, TQAQLLRVG (SEQ ID NO:34), any of one or more consecutive amino acids of SEQ ID NO: 34, N-aryl, or N-acyl with a substituent selected from a C1-C18 alkyl, a substituted alkyl or a heteroaryl moiety;

$X_2$ is M, S, C, substituted L, K, D, or E, where the side chain can be linked via an amide bond, or any amino acid that can form a bond with $X_8$, for example a disulfide or an amide bond;

$X_3$ is V, D, L, G, N, A, or S;
$X_4$ is V, D, L, G, N, A, S or T;
$X_5$ is V, D, L, G, N, A, or S;
$X_6$ is V, D, L, G, N, A, S, or absent;
$X_7$ is T, S, Hse (homoSER), Ahb ((S)-2-Amino-3-hydroxy-3-methylbutanoic acid) or (Ahp) (2R,3R)-2-Amino-3-hydroxy-4-methylpentanoic acid;
$X_8$ is M, S, C, substituted L, K, D, or E, or any amino acid that can form a bond with $X_2$, for example a disulfide or an amide bond;
$X_{21}$ is M, G, P, A, or absent;
$X_{22}$ is M, G, P, A, or absent;
$X_{23}$ is M, G, P, A, or absent;
$X_{24}$ is M, G, P, A, or absent;
$X_{25}$ is M, G, P, A, or absent;
$X_{26}$ is R or absent, wherein when $X_{26}$ is absent, $X_{27}$ is absent;
$X_{27}$ is Q or absent, wherein when $X_{27}$ is absent, $X_{26}$ is absent;
$X_{28}$ is D or E;
$X_{33}$ is D or E; and
biologically active fragments thereof.

In other embodiments, AFP-6 analogs comprise, or the active region consists of, compounds having an amino acid sequence of formula (III): $X_1$-$X_2$-QNLSHRLWQL-$X_{13}$-$X_{14}$-$X_{15}$-$X_{16}$-$X_{17}$-$X_{18}$-$X_{19}$-$X_{20}$-SAMV-$X_{25}$-PSSPHSY (SEQ ID NO:35) wherein $X_1$ is Q or absent;
$X_2$ is V or absent;
$X_{13}$ is M, G, P, A, or absent;
$X_{14}$ is M, G, P, A, or absent
$X_{15}$ is M, G, P, A, or absent;
$X_{16}$ is M, G, P, A, or absent;
$X_{17}$ is M, G, P, A, or absent,
$X_{18}$ is $R^1$ or absent, wherein when $X_{18}$ is absent, $X_{19}$ is absent;
$X_{19}$ is Q or absent, wherein when $X_{19}$ is absent, $X_{18}$ is absent
$X_{20}$ is D or E;
$X_{25}$ is D or E; and
biologically active fragments thereof.

Amino acid sequences of exemplary AFP-6 analogs for use in the disclosed methods include:

RVGCVLGTCQVQNLSHRLWQLMGPAGRQDSAPVDPSSPHSY (SEQ ID NO: 36)

GCVLGTCQVQNLSHRLWQLMGPAGRQDSAPVDPSSPHSY (SEQ ID NO: 37)

CVLGTCQVQNLSHRLWQLMGPAGRQDSAPVDPSSPHSY (SEQ ID NO: 38)

QVQNLSHRLWQLMGPAGRQDSAPVDPSSPHSY (SEQ ID NO: 39)

VQNLSHRLWQLMGPAGRQDSAPVDPSSPHSY (SEQ ID NO: 40)

VQNLSHLRLQLMGPAGRQDSAPVDPSSPHSY (SEQ ID NO: 41)

TQAQLLRVGCVLGTCQVQNLSHRLWQLRQDSAPVDPSSPHSY (SEQ ID NO: 42)

TQAQLLRVGCVLGTCQVQNLSHRLWQLDSAPVDPSSPHSY (SEQ ID NO: 43)

VGCVLGTCQVQNLSHRLWQLRQDSAPVDPSSPHSY (SEQ ID NO: 44)

CVLGTCQVQNLSHRLWQLRQESAPVEPSSPHSY (SEQ ID NO: 45)

TQAQLLRVGCSNLSTCQVQNLSHRLWQLMGPAGRQDSAPVDPSSPHSY (SEQ ID NO: 46)

TQAQLLRVGCNTATCQVQNLSHRLWQLMGPAGRQDSAPVDPSSPHSY (SEQ ID NO: 47)

RVGCGNLSTCQVQNLSHRLWQLMGPAGRQDSAPVDPSSPHSY (SEQ ID NO: 48)

TQAQLLRVGCDTATCQVQNLSHRLWQLMGPAGRQDSAPVDPSSPHSY (SEQ ID NO: 49)

TQAQLLRVGCGNLSTCQVQNLSHRLWQLMGPAGRQDSAPVDPSSPHSY (SEQ ID NO: 50)

TQAQLLRVGMVLGTMQVQNLSHRLWQLMGPAGRQDSAPVDPSSPHSY (SEQ ID NO: 51)

GMVLGTMQVQNLSHRLWQLMGPAGRQDSAPVDPSSPHSY (SEQ ID NO: 52)

VGMVLGTMQVQNLSHRLWQLRQDSAPVDPSSPHSY (SEQ ID NO: 53)

RVGCGNLSTCQVQNLSHRLWQLMGPAGRQDSAPVDPSSPHSY (SEQ ID NO: 54)

VGCGNLSTCQVQNLSHRLWQLRQDSAPVDPSSPHSY (SEQ ID NO: 55)

VCNTATCQVQNLSHRLWQLRQDSAPVDPSSPHSY (SEQ ID NO: 56)

GCNTATCQVQNLSHRLWQLRQDSAPVDPSSPHSY (SEQ ID NO: 57)

TQAQLLRVGCVLGTCQVQNLSHRLWQLMGPAGRQESAPVEPSSPHSY (SEQ ID NO: 58)

TQAQLLRVGCVLGTCQVQNLSHRLWQLMGPAGRQDSAPVEPSSPHSY (SEQ ID NO: 59)

GTMQVQNLSHRLWQLRQDSAPVEPSSPHSY (SEQ ID NO: 60)

VGCVLGTCQVQNLSHRLWQLMGPAGRQDSAPVEPSSPHSY (SEQ ID NO: 61)

```
                                                    (SEQ ID NO: 62)
VGCVLGTCQVQNLSHRLWQLRQDSAPVEPSSPHSY (SEQ ID NO: 63)
GCNTATCQVQNLSHRLWQLRQDSAPVEPSSPHSY (SEQ ID NO: 64)
GCSNLSTCQVQNLSHRLWQLRQDSAPVEPSSPHSY (SEQ ID NO: 65)
GCGNLSTCQVQNLSHRLWQLRQDSAPVEPSSPHSY (SEQ ID NO: 66)
GCVLGTCQVQNLSHRLWQLRQESAPVEPSSPHSY.
```

Other exemplary AFP-6 analogs and derivatives are disclosed in U.S. Pat. No. 6,965,013 and PCT Publication No. WO 2004/048547, each of which is herein incorporated by reference.

Amylin agonists contemplated in the use in the methods disclosed herein include analogs identified in U.S. Pat. No. 6,087,334, the contents of which is hereby incorporated by reference. Such useful amylin agonists include analogs of formula IV: $X_1$-$Xaa_1$-$X_2$-$Xaa_2$-$X_3$-$Xaa_3$-$X_4$-$Xaa_4$-$X_5$-$Xaa_5$-$X_6$ (SEQ ID NO:67) wherein $X_1$ is Lys, Arg or absent;

$X_2$ is $Xaa_6Xaa_7Xaa_8Xaa_9$ (SEQ. ID. NO.68) or Z-$Xaa_{10}$SerThr, provided that if $X_2$ is Z-$Xaa_{10}$SerThr, then $X_1$ and $Xaa_1$ are both absent;

$X_3$ is AlaThr, AlaSer, SerMet, GluThr or ValThr;

$X_4$ is ArgLeuAla, HisLeuAla, ArgIleAla, LysIleAla, ArgMetAla, HisMetAla, LysMetAla or ArgLeuThr;

$X_5$ is PheLeu, PheIle, PheMet, TyrLeu, TyrIle, TyrMet, TrpIle or TrpMet;

$X_6$ is ArgSerSerGlyTyr (SEQ ID NO:69), LysSerSerGlyTyr (SEQ ID NO:70), His SerSerGlyTyr (SEQ ID NO:71), ProSerSerGlyTyr (SEQ ID NO:72), ArgSerArgGlyTyr (SEQ ID NO:73), ArgThrSerGlyTyr (SEQ ID NO:74), ArgAlaSerGlyTyr (SEQ ID NO:75), AlaSerSerGlyTyr (SEQ ID NO:76), ArgSerAlaGlyTyr (SEQ ID NO:77), His SerAlaGlyTyr (SEQ ID NO:78), ArgSerGlyTyr (SEQ ID NO:79), ArgSer, LysSer, His Ser, ArgThr, ProSer or Arg;

$Xaa_1$ is Cys or absent;
$Xaa_2$ is Cys or Ala;
$Xaa_3$ is Gln, Ala or Asn;
$Xaa_4$ is Asn, Ala or Gln;
$Xaa_5$ is Val, Ala, Ile, Met, Leu, PentylGly, or t-butylGly;
$Xaa_6$ is Asn, Gln or Asp;
$Xaa_7$ is Thr, Ser, Met, Val, Leu or Ile;
$Xaa_8$ is Ala or Val;
$Xaa_9$ is Thr or Ser;
$Xaa_{10}$ is Leu, Val, Met or Ile;

Z is an alkanoyl group of about 1 to about 8 carbon atoms or absent;

and pharmaceutically acceptable salts thereof.

Amylin agonists contemplated in the use in the methods disclosed herein include the amylin family peptides, analogs and derivatives (referred to herein as LHC (loop helix C-terminus) peptides) described in U.S. Pat. Application No. 60/543,275 and in PCT Application No. PCT/US2005/004631, each of which is herein incorporated by reference in its entirety.

The LHC peptides for use in the methods provided act as an agonist for at least one biological effect of calcitonin, amylin, CGRP, or any combination of the three herein disclosed or bind to at least one of the receptors of amylin, calcitonin, or CGRP. Receptor binding activity and biological activity of exemplary LHC peptides are described in U.S. Pat. Application No. 60/543,275 and in PCT application No. PCT/US2005/004631. In a general aspect, these polypeptide agonists have at least a loop region of amylin or calcitonin and analogs thereof, an α helix region of at least a portion of an α helix region of calcitonin or analogs thereof or an α helix region having a portion of an amylin α helix region and a calcitonin α helix region or their respective analogs, and a C-terminal tail of amylin or calcitonin or analogs thereof, with the proviso that the C-terminal tail of calcitonin or a calcitonin analog is not proline (Pro), hydroxyproline (Hyp), homoserine (Hse) or derivatives of Hse.

In certain embodiments, these LHC peptides have an amylin or amylin analog loop region, at least a portion of a calcitonin or calcitonin analog α helix region, and an amylin or amylin analog C-terminal tail. In other embodiments, these LHC peptides have a calcitonin or calcitonin analog loop region, at least a portion of a calcitonin or calcitonin analog α helix region, and an amylin or amylin analog C-terminal tail. In still other embodiments, these LHC peptides have an amylin or amylin analog loop region, at least a portion of an amylin or amylin analog α helix region and at least a portion of a calcitonin or calcitonin analog α helix region, and an amylin or amylin analog C-terminal tail. In yet other embodiments, these LHC peptides have a calcitonin or calcitonin analog loop region, at least a portion of an amylin or amylin analog α helix region and at least a portion of a calcitonin or calcitonin analog α helix region, and an amylin or amylin analog C-terminal tail. In still yet other embodiments, these LHC peptides have an amylin or amylin analog loop region, a portion or a calcitonin or calcitonin analog α helix region or at least a portion of an amylin or amylin analog α helix region and at least a portion of a calcitonin or calcitonin analog α helix region, and a calcitonin or calcitonin analog C-terminal tail.

In certain embodiments, the loop region of these LHC peptides may further comprise no more than one, two, three, or four modifications including substitutions, insertions, or deletions from the amylin or calcitonin loop, and analogs thereof. It is further contemplated that these LHC peptides may have additional modifications at the N-terminal portion of the loop comprising a N-cap region, that may have hydrophobic or hydrophilic characteristics such as acetyl, isocaproyl, 3,6-dioxyoctanoic acid, or 1-amino-4,7,10-trioxa-13-tridecanamine succinimic acid. Modifications may further include one, two, three or more additional amino acids. This is an area which allows for many modifications too numerous to mention, but would be understood by one of skill in the art based upon what is exemplified further in the present application.

Such useful amylin agonists may include LHC peptides comprising an amino acid sequence of formula V: $Xaa_1$ X $Xaa_3$ $Xaa_4$ $Xaa_5$ $Xaa_6$ Y $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$ $Xaa_{29}$ $Xaa_{30}$ $Xaa_{31}$ $Xaa_{32}$ (SEQ ID NO:80) wherein $Xaa_1$ is A, C, hC (homoCys), D, E, F, I, L, K, hK (homoLys), R, hR (homoArg), S, Hse(homoSer), T, G, Q, N, M, Y, W, P, Hyp (hydroxyPro), H, V or absent;

$Xaa_3$ is A, D, E, N, Q, G, V, R, K, hK, hR, H, I, L, M, or absent;

$Xaa_4$ is A, I, L, S, Hse, T, V, M, or absent;
$Xaa_5$ is A, S, T, Hse, Y, V, I, L, or M;
$Xaa_6$ is T, A, S, Hse, Y, V, I, L, or M;
$Xaa_8$ is A, V, I, L, F, or M;
$Xaa_9$ is L, T, S, Hse, V, I, or M;
$Xaa_{10}$ is G, H, Q, K, R, N, hK, or hR;

$Xaa_{11}$ is K, R, Q, N, hK, hR, or H;
$Xaa_{12}$ is L, I, V, F, M, W, or Y;
$Xaa_{13}$ is A, F, Y, N, Q, S, Hse, or T;
$Xaa_{14}$ is A, D, E, G, N, K, Q, R, H, hR, or hK;
$Xaa_{15}$ is A, D, E, F, L, S, Y, I, V, or M;
$Xaa_{16}$ is L, F, M, V, Y, or I;
$Xaa_{17}$ is H, Q, N, S, Hse, T, or V;
$Xaa_{18}$ is K, hK, R, hR, H, u (Cit), or n (Orn);
$Xaa_{19}$ is F, L, S, Hse, V, I, T, or absent;
$Xaa_{20}$ is H, R, K, hR, hK, N, Q, or absent;
$Xaa_{21}$ is T, S, Hse, V, I, L, Q, N, or absent;
$Xaa_{22}$ is F, L, M, V, Y, or I;
$Xaa_{23}$ is P or Hyp;
$Xaa_{24}$ is P, Hyp, R, K, hR, hK, or H;
$Xaa_{25}$ is T, S, Hse, V, I, L, F, or Y;
$Xaa_{26}$ is N, Q, D, or E;
$Xaa_{27}$ is T, V, S, F, I, or L;
$Xaa_{28}$ is G or A;
$Xaa_{29}$ is S, Hse, T, V, I, L, or Y;
$Xaa_{30}$ is E, G, K, N, D, R, hR, hK, H, or Q;
$Xaa_{31}$ is A, T, S, Hse, V, I, L, F, or Y; and
$Xaa_{32}$ is F, P, Y, Hse, S, T, or Hyp;

wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond.

Alkyl chains may include lower alkyl groups having from about 1 to about 6 carbon atoms. In certain embodiments, the intramolecular linkage may be a disulfide, amide, imine, amine, alkyl or alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

Useful amylin agonists may also include LHC peptides comprising the amino acid sequence of formula VI: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ P $Xaa_{24}$ T N $Xaa_{27}$ G S $Xaa_{30}$ $Xaa_{31}$ $Xaa_{32}$ (SEQ ID NO:81) wherein $Xaa_1$ is A, C, D, F, I, K, S, T, or absent;
$Xaa_2$ is C, D, S, or absent;
$Xaa_3$ is A, D, N, or absent;
$Xaa_4$ is A, L, T, or absent;
$Xaa_5$ is A or S;
$Xaa_6$ is T, A, S, or V;
$Xaa_7$ is C, K, or A;
$Xaa_8$ is A, V, L, or M;
$Xaa_9$ is L or T;
$Xaa_{10}$ is G, H, or Q;
$Xaa_{11}$ is K, R, Q, or hArg;
$Xaa_{12}$ is L, W, or Y;
$Xaa_{13}$ is A, F, N, Q, S, or T;
$Xaa_{14}$ is A, D, E, G, N, K, Q, or R;
$Xaa_{15}$ is A, D, E, F, L, S, or Y;
$Xaa_{16}$ is L, or F;
$Xaa_{17}$ is H, Q, S, or V;
$Xaa_{18}$ is K, R, hArg, u (Cit), or n (Orn);
$Xaa_{19}$ is F, L, S, or absent;
$Xaa_{20}$ is H, Q, or absent;
$Xaa_{21}$ is T, N, or absent;
$Xaa_{22}$ is F, L, M, V, or Y;
$Xaa_{24}$ is P or R;
$Xaa_{27}$ is T or V;
$Xaa_{30}$ is E, G, K, or N;
$Xaa_{31}$ is A or T; and
$Xaa_{32}$ is F, P, or Y.

Useful amylin agonists may also include LHC peptides comprising the amino acid sequence of formula VII: $Xaa_1$ $Xaa_2$ $Xaa_3$ $Xaa_4$ $Xaa_5$ T $Xaa_7$ $Xaa_8$ $Xaa_9$ $Xaa_{10}$ $Xaa_{11}$ L $Xaa_{13}$ $Xaa_{14}$ $Xaa_{15}$ L $Xaa_{17}$ $Xaa_{18}$ $Xaa_{19}$ $Xaa_{20}$ $Xaa_{21}$ $Xaa_{22}$ P $Xaa_{24}$ T N $Xaa_{27}$ G S $Xaa_{30}$ $Xaa_{31}$ $Xaa_{32}$, (SEQ ID NO:82) wherein $Xaa_1$ is A, C, F, I, K, S, or absent;
$Xaa_2$ is C, D, or S;
$Xaa_3$ is A, D or N;
$Xaa_4$ is A, L or T;
$Xaa_5$ is A or S;
$Xaa_7$ is C or K;
$Xaa_8$ is A or V;
$Xaa_9$ is L or T;
$Xaa_{10}$ is G, H, or Q;
$Xaa_{11}$ is K, R, or hArg;
$Xaa_{13}$ is A, F, N, S, or T;
$Xaa_{14}$ is A, D, E, G, N, Q, or R;
$Xaa_{15}$ is A, E, F, L, S, or Y;
$Xaa_{17}$ is H, S, or V;
$Xaa_{18}$ is K, R, hArg, u (Cit), or n (Orn);
$Xaa_{19}$ is F, L, or S;
$Xaa_{20}$ is H or Q;
$Xaa_{21}$ is T or N;
$Xaa_{22}$ is F, L, M, V, or Y;
$Xaa_{24}$ is P or R;
$Xaa_{27}$ is T, or V;
$Xaa_{30}$ is E, G, K, or N;
$Xaa_{31}$ is A, or T; and
$Xaa_{32}$ is F, P, or Y.

Useful amylin agonists may also include LHC peptides comprising the amino acid sequence of formula VIII: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ P $Xaa_{24}$ T N $Xaa_{27}$ G S $Xaa_{30}$ $Xaa_{31}$ $Xaa_{32}$ (SEQ ID NO:83) wherein $Xaa_1$ is A, C, D, F, K, T, or absent;
$Xaa_2$ is A, C, D, S, or absent;
$Xaa_3$ is A, D, N, or absent;
$Xaa_4$ is A, L, T, or absent;
$Xaa_5$ is A or S;
$Xaa_6$ is A, S, T, or V;
$Xaa_7$ is A, C, or K;
$Xaa_8$ is A, L, M, or V;
$Xaa_9$ is L or T;
$Xaa_{10}$ is G, H, or Q;
$Xaa_{11}$ is K, Q, or R;
$Xaa_{12}$ is L, W, or Y;
$Xaa_{13}$ is A, N, Q, S, or T;
$Xaa_{14}$ is A, D, E, G, K, N, Q, or R;
$Xaa_{15}$ is A, D, E, F, L, S, or Y;
$Xaa_{16}$ is F or L;
$Xaa_{17}$ is H, Q, S or V;
$Xaa_{18}$ is K, or R;
$Xaa_{19}$ is F, L, S, or absent;
$Xaa_{20}$ is H, K, Q, or absent;
$Xaa_{21}$ is Q, T, or absent;
$Xaa_{22}$ is F, L, or Y;
$Xaa_{24}$ is P or R;
$Xaa_{27}$ is T or V;
$Xaa_{30}$ is E, K or N;
$Xaa_{31}$ is A or T; and
$Xaa_{32}$ is F, Y, or absent.

In a general aspect, the sequence of formula V, VI, VII, or VIII further comprises 1, 2, 3, 4, 5, 6, 7, 8, 9, 10, 11, 12, or more modifications of substitutions, insertions, deletions, elongations and/or derivatizations. In certain embodiments, the sequence of formula V, VI, VII, or VIII comprises a deletion at position 24. In certain embodiments, the sequence of formula V, VI, or VII comprises a Val inserted between amino acids at positions 22 and 23. In other embodiments, the sequence of formula V, VI, or VII comprises a Gln inserted between positions 22 and 23. In still other embodiments, the sequence of formula V, VI, or VII comprises a sequence of Gln-Thr-Tyr between positions 22 and 23. In yet other embodiments, the sequence of formula V, VI, or VII comprises a sequence of Leu-Gln-Thr-Tyr (SEQ ID NO: 84) between positions 22 and 23. In another general aspect, the modifications of formula V, VI, or VII may be at the N-terminal end. In certain embodiments, the N-terminal portion of formula V, VI, or VII has an added octylglycine. In other embodiments, the N-terminal portion of formula V, VI, or VII has an added isocap. Other embodiments are described in PCT Application No. PCT/US2005/004631 and incorporated by reference.

Exemplary compounds described with reference to human amylin (SEQ ID NO:1; hAmylin), rat amylin (SEQ ID NO:2; rAmylin), and salmon calcitonin (sCT) CSNLSTCV-LGKLSQELHKLQTYPRTNTGSGTP (SEQ ID NO:85) with modifications at the position(s) indicated include, (1-7 hAmylin)($^{18}$Arg 8-27 sCT)(33-37 hAmylin) (SEQ ID NO:86);

(1-7 hAmylin)($^{11,18}$Arg$^{22}$Leu 8-27sCT)(33-37 hAmylin) (SEQ ID NO:87);

(1-7 hAmylin)($^{11,18}$Arg$^{24}$Pro 8-27 sCT)(33-37 hAmylin) (SEQ ID NO:88);

(1-7 hAmylin)($^{11,18}$Arg 8-24 sCT)(30-37 hAmylin) (SEQ ID NO:89);

(1-7 hAmylin)($^{11,18}$Arg 8-21 sCT)(27-37 rAmylin) (SEQ ID NO:90);

($^{8}$Val$^{9}$Leu$^{10}$Gly 1-15 hAmylin)($^{18}$Arg 16-27 sCT)(31-37 hAmylin) (SEQ ID NO:91);

($^{1}$Ala 1-7 hAmylin)($^{11,18}$Arg 8-27 sCT)(33-37 hAmylin) (SEQ ID NO:92);

($^{3}$Ala 1-7 hAmylin)($^{11,18}$Arg 8-27 sCT)(33-37 hAmylin) (SEQ ID NO:93);

($^{4}$Ala 1-7 hAmylin)($^{11,18}$Arg 8-27 sCT)(33-37 hAmylin) (SEQ ID NO:94);

($^{6}$Ala 1-7 hAmylin)($^{11,18}$Arg 8-27 sCT)(33-37 hAmylin) (SEQ ID NO:95);

($^{2}$Ala$^{11,18}$Arg 1-27 sCT)(33-37 hAmylin) (SEQ ID NO:96);

(Isocap-$^{7}$Ala$^{11,18}$Arg 5-27 sCT)(33-37 hAmylin) (SEQ ID NO:97);

($^{4}$Ala$^{11,18}$Arg 1-27 sCT)(33-37 hAmylin) (SEQ ID NO:98);

($^{5}$Ala$^{11,18}$Arg 1-27 sCT)(33-37 hAmylin) (SEQ ID NO:99);

($^{6}$Ala$^{11,18}$Arg 1-27 sCT)(33-37 hAmylin) (SEQ ID NO:100);

(1-7 hAmylin)($^{11}$Arg 8-27 sCT)(33-37 hAmylin) (SEQ ID NO:101);

($^{13}$Ser$^{14}$Gln$^{15}$Glu 1-16 hAmylin)($^{17}$Arg$^{30}$Asn$^{32}$Tyr 17-32 sCT) (SEQ ID NO:102);

($^{3}$Ala$^{11,18}$Arg 1-27 sCT)(33-37 hAmylin) (SEQ ID NO:103);

(Acetyl-$^{2,7}$Agy$^{11,18}$Arg 1-27 sCT)(33-37 hAmylin) (SEQ ID NO:104);

(Acetyl-$^{2,7}$Agy 1-7 hAmylin)($^{11,18}$Arg 8-27 sCT)(33-37 hAmylin) (SEQ ID NO:105);

(Isocap-$^{7}$Ala$^{10}$Aib$^{11}$Lys(For)$^{17}$Aib$^{18}$Lys(For) 5-27 sCT)(33-37 hAmylin) (SEQ ID NO:106);

(Isocap-$^{7}$Ala$^{10}$Aib$^{11}$Lys(For)$^{17}$Aib$^{18}$Lys(For) 5-24sCT)(30-37 hAmylin) (SEQ ID NO:107);

(Isocap-$^{7}$Ala$^{10}$Aib$^{11}$Lys(For)$^{17}$Aib$^{18}$Lys(For) 5-22 sCT)($^{28,29}$Pro 28-37 hAmylin) (SEQ ID NO:108);

(Isocap-$^{7}$Ala$^{11}$Aib$^{11}$Lys(For)$^{17}$Aib$^{18}$Lys(For) 5-21 sCT)($^{28,29}$Pro 27-37 hAmylin) (SEQ ID NO:109);

(1-7 hAmylin)(LLQQWQKLLQKLKQ (SEQ ID NO:110))($^{28}$Pro$^{29}$Arg$^{32}$Thr 27-37 hAmylin) (SEQ ID NO:111);

(1-7 hAmylin)(LLQQLQKLLQKLKQY (SEQ ID NO:112))($^{28}$Pro$^{29}$Arg$^{32}$Thr 28-37 hAmylin) (SEQ ID NO:113);

($^{6}$Ser 1-7 hAmylin)($^{11,18}$Arg 8-27 sCT)(33-37 hAmylin) (SEQ ID NO:114);

($^{6}$Val 1-7 hAmylin)(11,18Arg 8-27 sCT)(33-37 hAmylin) (SEQ ID NO:115);

(1-7 hAmylin)($^{11,18}$Arg 8-18 SCT)($^{28}$Pro$^{29}$Arg$^{32}$Thr 27-37 hAmylin) (SEQ ID NO:116);

(1-7 hAmylin)($^{11}$Arg 8-17 sCT)($^{28}$Pro$^{21}$Arg$^{32}$Thr 27-37 hAmylin) (SEQ ID NO:117);

(1-7 hAmylin)($^{11}$Arg 8-16 sCT)($^{27}$Tyr$^{28}$Pro$^{29}$Arg$^{32}$Thr 27-37 hAmylin) (SEQ ID NO:118);

(1-7 hAmylin)($^{11}$Arg 8-15sCT)($^{27}$Tyr$^{28}$Pro$^{29}$Arg$^{32}$Thr 27-37 hAmylin) (SEQ ID NO:119);

(1-7 hAmylin)($^{11}$Arg 8-14 sCT)($^{27}$Tyr$^{28}$Pro$^{29}$Arg$^{32}$Thr 27-37 hAmylin) (SEQ ID NO:120);

(1-7 hAmylin)($^{11,18}$Lys(For) 8-27 sCT)(33-37 hAmylin) (SEQ ID NO:121);

($^{6}$D-Thr 1-7 hAmylin)($^{11,18}$Arg 8-27 sCT)(33-37 hAmylin) (SEQ ID NO:122);

(Acetyl-1-7 hAmylin)($^{11,18}$Lys(PEG5000) 8-27 sCT)(33-37 hAmylin) (SEQ ID NO:123);

(Acetyl-$^{1}$Ala 1-7 hAmylin)($^{11}$Lys(PEG5000)$^{18}$Arg 8-27 sCT)(33-37 hAmylin) (SEQ ID NO:124);

(Acetyl-$^{1}$Ala 1-7 hAmylin)($^{11}$Arg$^{18}$Lys(PEG5000) 8-27 sCT)(33-37 hAmylin) (SEQ ID NO:125);

(1-7 hAmylin)($^{11,18}$Arg 8-21 sCT)(19-27 sCT)(33-37 hAmylin) (SEQ ID NO:126);

(1-7 hAmylin)($^{11,18}$Arg 8-21 sCT)($^{18}$Leu 18-27 sCT)(33-37 hAmylin) (SEQ ID NO:127);

(1-7 hAmylin)(8-27 sCT)(33-37 hAmylin) (SEQ ID NO:128);

($^{5}$Ser 1-7 hAmylin)($^{11,18}$Arg 8-27 sCT)(33-37 hAmylin) (SEQ ID NO:129);

(1-12 hAmylin)($^{18}$Arg 13-27 sCT)(33-37 hAmylin) (SEQ ID NO:130);

(1-12 hAmylin)($^{18}$Arg 13-24 sCT)(30-37 hAmylin) (SEQ ID NO:131);

($^{5}$Ser$^{15}$Glu$^{18}$Arg 1-18hAmylin)(19-24 sCT)(30-37 hAmylin) (SEQ ID NO:132);

(⁶Hse 1-7 hAmylin)(¹¹,¹⁸Arg 8-27 sCT)(33-37 hAmylin) (SEQ ID NO:133);

(⁶Ahb 1-7 hAmylin)(¹¹,¹⁸Arg 8-27 sCT)(33-37 hAmylin) (SEQ ID NO:134);

(⁶Ahp 1-7hAmylin)(¹¹,¹⁸Arg 8-27 sCT)(33-37 hAmylin) (SEQ ID NO:135);

⁶Thr(OPO₃H₂) 1-7 hAmylin)(¹¹,¹⁸Arg 8-27 sCT)(33-37 hAmylin) (SEQ ID NO:136);

(7Ala¹¹,¹⁸Arg 5-27 sCT)(33-37 hAmylin) (SEQ ID NO:137);

(1-7 hAmylin)(¹¹,¹⁸Orn 8-27 sCT)(33-37 hAmylin) (SEQ ID NO:138);

(1-7 hAmylin)(¹¹,¹⁸Cit 8-27 sCT)(33-37 hAmylin) (SEQ ID NO:139);

(1-7 hAmylin)(¹¹,¹⁸homoLys 8-27 sCT)(33-37 hAmylin) (SEQ ID NO:140);

(L-Octylglycine-1-7-hAmylin)(¹¹,¹⁸Arg 8-27 sCT)(33-37 hAmylin) (SEQ ID NO:141);

(N-3,6-dioxaoctanoyl-1-7-hAmylin)(¹¹,¹⁸Arg 8-27 sCT)(33-37 hAmylin) (SEQ ID NO:142);

(cyclo(1-7)-¹Asp⁷Lys¹¹,¹⁸Arg 1-27 sCT)(33-37 hAmylin) (SEQ ID NO:143);

(cyclo(2-7)-²Asp⁷Lys 1-7 hAmylin)(¹¹,¹⁸Arg 8-27 sCT)(33-37 hAmylin) (SEQ ID NO:144);

(cyclo (2-7) hAmylin)(¹¹,¹⁸Arg 8-27 sCT)(33-37 hAmylin) (SEQ ID NO:145);

(1-7 hAmylin)(¹¹,¹⁸Arg 8-27 sCT)(33-37 hAmylin-9Anc) (SEQ ID NO:146);

(1-7 hAmylin)(¹¹,¹⁸Arg 8-27 sCT)(33-37 hAmylin-L-octylglycine) (SEQ ID NO:147);

(N-isocaproyl-1-7-hAmylin)(¹¹,¹⁸Arg 8-27sCT)(33-37 hAmylin) (SEQ ID NO:148);

(1-7 hAmylin)(¹¹,¹⁸homoArg 8-27 sCT)(33-37 hAmylin) (SEQ ID NO:149);

(¹Phe 1-7 hAmylin)(¹¹,¹⁸Arg 8-27 sCT)(33-37 hAmylin) (SEQ ID NO:150);

(1-7 hAmylin)(¹¹,¹⁸Arg 8-24 sCT)(³²Thr 30-37 hAmylin) (SEQ ID NO:151);

(1-7 hAmylin)(¹¹,¹⁸Arg 8-27 sCt)(33-37 hAmylinlin) (SEQ ID NO:152);

(¹⁵Glu¹⁸Arg 1-18 hAmylin)(19-24 sCT)(30-37 hAmylin) (SEQ ID NO:153);

(¹³Ala¹⁴Asp¹⁵Phe 1-18 hAmylin)(19-23 sCT)(30-37 hAmylin) (SEQ ID NO:154); and (2-18 hAmylin)(19-23 sCT)(30-36 hAmylin) (SEQ ID NO:155). Peptides useful in the compositions and methods provided herein, like those above, can be in the acid or amide form.

Exemplary peptides also for use in the compositions and methods provided herein include:

```
KCNTATCVLGKLSQELHRLQTYPRTNTGSNTY           (SEQ ID NO: 156)

KCNTATCVLGRLSQELHRLQTLPRTNTGSNTY           (SEQ ID NO: 157)

KCNTATCVLGRLSQELHRLQTYPPTNTGSNTY           (SEQ ID NO: 158)

KCNTATCVLGRLSQELHRLQTYPRTNVGSNTY           (SEQ ID NO: 159)

KCNTATCVLGRLSQELHRLQTLPPTNYGSNTY           (SEQ ID NO: 160)

KCNTATCVLGRLANFLHRLQTYPRTNTGSNTY           (SEQ ID NO: 161)

ACNTATCVLGRLSQELHRLQTYPRTNTGSNTY           (SEQ ID NO: 162)

KCNAATCVLGRLSQELHRLQTYPRTNTGSNTY           (SEQ ID NO: 163)

KCNTAACVLGRLSQELHRLQTYPRTNTGSNTY           (SEQ ID NO: 164)

CANLSTCVLGRLSQELHRLQTYPRTNTGSNTY           (SEQ ID NO: 165)

isocaproyl-STAVLGRLSQELHRLQTYPRTNTGSNTY    (SEQ ID NO: 166)

CSNASTCVLGRLSQELHRLQTYPRTNTGSNTY           (SEQ ID NO: 167)

CSNLATCVLGRLSQELHRLQTYPRTNTGSNTY           (SEQ ID NO: 168)

CSNLSACVLGRLSQELHRLQTYPRTNTGSNTY           (SEQ ID NO: 169)

KCNTATCVLGRLSQELHKLQTYPRTNTGSNTY           (SEQ ID NO: 170)

KCNTATCVLGRLSQELHRLQTYPRTNTGSGTP           (SEQ ID NO: 171)

CSALSTCVLGRLSQELHRLQTYPRTNTGSNTY           (SEQ ID NO: 172)

Ac-(Agy)SNLST(Agy)VLGRLSQELHRLQTYPRTNTGSNTY (SEQ ID NO: 173)

Ac-K(Agy)NTAT(Agy)VLGRLSQELHRLQTYPRTNTGSNTY (SEQ ID NO: 174)

Isocaproyl-STAVL(Aib)RLSQELRLQTYPRTNTGSGTP  (SEQ ID NO: 175)
```

-continued

| | |
|---|---|
| Isocaproyl-STAVLG[K(For)]LSQELH[K(For)]LQTYPRTNTGSGTP | (SEQ ID NO: 176) |
| Isocaproyl-STAVL(Aib)[K(For)]LSQEL(Aib)[K(For)]LQTYPRTNTGSNTY | (SEQ ID NO: 177) |
| Isocaproyl-STAVL(Aib)[K(For)]LSQEL(Aib)[K(For)]LQTYPRTNYGSNTY | (SEQ ID NO: 178) |
| KCNTATCLLQQLQKLLQKLKQYPRTNTGSNTY | (SEQ ID NO: 179) |
| KCNTASCVLGRLSQELHRLQTYPRTNTGSNTY | (SEQ ID NO: 180) |
| KCNTAVCVLGRLSQELHRLQTYPRTNTGSNTY | (SEQ ID NO: 181) |
| KCNTATCVLGRLSQELHRYPRTNTGSNTY | (SEQ ID NO: 182) |
| KCNTATCVLG[K(For)]LSQELH[K(For)L]QTYPRTNTGSNTY | (SEQ ID NO: 183) |
| KCNTA(d-Thr)CVLGRLSQELHRLQTYPRTNTGSNTY | (SEQ ID NO: 184) |
| KCNTA(dAh)CVLGRLSQELHRLQTYPRTNTGSNTY | (SEQ ID NO: 185) |
| Ac-ACNTATCVLGRLSQELHK(PEG5000)LQTYPRTNTGSNTY | (SEQ ID NO: 186) |
| KCNTATCVLGRLSQELHRLQTLQTYPRTNTGSNTY | (SEQ ID NO: 187) |
| KCNTATCVLGRLSQELHRLQTLLQTYPRTNTGSNTY | (SEQ ID NO: 188) |
| KCNTATCVLGKLSQELHKLQTYPRTNTGSNTY | (SEQ ID NO: 189) |
| KCNTSTCVLGRLSQELHRLQTYPRTNTGSNTY | (SEQ ID NO: 190) |
| KCNTATCATQRLSQELHRLQTYPRTNTGSNTY | (SEQ ID NO: 191) |
| KCNTATCATQRLSQELHRLQTYPRTNVGSNTY | (SEQ ID NO: 192) |
| KCNTSTCATQRLANELVRLQTYPRTNVGSNTY | (SEQ ID NO: 193) |
| KCNTA(Hse)CVLGRLSQELHRLQTYPRTNTGSNTY | (SEQ ID NO: 194) |
| KCNTA(Ahb)CVLGRLSQELHRLQTYPRTNTGSNTY | (SEQ ID NO: 195) |
| KCNTA(Ahp)CVLGRLSQELHRLQTYPRTNTGSNTY | (SEQ ID NO: 196) |
| KCNTAT(OPO$_3$H$_2$)CVLGRLSQELHRLQTYPRTNTGSNTY | (SEQ ID NO: 197) |
| KCNTATCVLG(Orn)LSQELH(Orn)LQTYPRTNTGSNTY | (SEQ ID NO: 198) |
| KCNTATCVLG(Cit)LSQELH(Cit)LQTYPRTNTGSNTY | (SEQ ID NO: 199) |
| KCNTATCVLG(hK)LSQELH(hK)LQTYPRTNTGSNTY | (SEQ ID NO: 200) |
| L-OctylglycineKCNTATCVLGRLSQELHRLQTYPRTNTGSNTY | (SEQ ID NO: 201) |
| N-3,6-dioxaoctanoyl-CNTATCVLGRLSQELHRLQTVPRTNTGSNTY | (SEQ ID NO: 202) |
| KCNTATCMLGRYTQDFHRLQTYPRTNTGSNTY | (SEQ ID NO: 203) |
| DSNLSTKVLGRLSQELHRLQTYPRTNTGSNTY | (SEQ ID NO: 204) |
| KDNTATKVLGRLSQELHRLQTYPRTNTGSNTY | (SEQ ID NO: 205) |
| CNTATCVLGRLSQELHRLQTYPRTNTGSNTY | (SEQ ID NO: 206) |
| KCNTATCVLGRLSQELHRLQTYPRTNTGSNTY(9Anc) | (SEQ ID NO: 207) |
| KCNTATCVLGRLSQELHRLQTYPRTNTGSNTY(L-octylglycine) | (SEQ ID NO: 208) |
| N-isocaproyl-KCNTATCVLGRLSQELHRLQTYPRTNTGSNTY | (SEQ ID NO: 209) |
| KCNTATCVLG(hR)LSQELH(hR)LQTYPRTNTGSNTY | (SEQ ID NO: 210) |
| FCNTATCVLGRLSQELHRLQTYPRTNTGSNTY | (SEQ ID NO: 211) |
| KCNTATCVLGRLSQELH(Cit)LQTYPRTNTGSNTY | (SEQ ID NO: 212) |
| KCNTATCVLGRLSQELH(Orn)LQTYPRTNTGSNTY | (SEQ ID NO: 213) |
| ICNTATCVLGRLSQELHRLQTYPRTNTGSNTY | (SEQ ID NO: 214) |
| 1-Octylglycine-CNTATCVLGRLSQELHRLQTYPRTNTGSNTY | (SEQ ID NO: 215) |

-continued

| | |
|---|---|
| Isocaproyl-CNTATCVLGRLSQELHRLQTYPRTNTGSNTY | (SEQ ID NO: 216) |
| KCNTATCVLG(Cit)LSQELHRLQTYPRTNTGSNTY | (SEQ ID NO: 217) |
| KCNTATCVLGRLSQELHRLQTYPRTNTGSNTY(4ABU) | (SEQ ID NO: 218) |
| Isocaproyl-KCNTATCVLGRLSQELHRLQTYPRTNTGSNTY(4ABU) | (SEQ ID NO: 219) |
| KCNTSTCATQRLANELVRLQTYPRTNVGSEAF | (SEQ ID NO: 220) |
| KCNTATCVLGRLSQELHRLQTYPTNVGSEAF | (SEQ ID NO: 221) |
| KCNTATCVLGRLSRSLHRLQTYPRTNTGSNTY | (SEQ ID NO: 222) |
| KCNTATCVTHRLSQELHRLQTYPRTNTGSNTY | (SEQ ID NO: 223) |
| KCNTATCVLGRLADFLHRLQTYPRTNTGSNTY | (SEQ ID NO: 224) |
| CNTATCVLGRLSQELHRLQTYPRTNTGSNT | (SEQ ID NO: 225) |
| KCNTATCVLGRLSQELHRLQNFVPRTNTGSNTY | (SEQ ID NO: 226) |
| KCNTATCVLGRLSQELHRLQTYPRTNTGSETF | (SEQ ID NO: 227) |
| ACDTATCVLGRLSQELHRLQTYPRTNTGSNTY | (SEQ ID NO: 228) |
| KCNTATCVLGRLSQELHRLQTYPRTNTGSKAF | (SEQ ID NO: 229) |
| KCDTATCVTHRLAGLLSRSQTYPRTNTGSNTY | (SEQ ID NO: 230) |
| KCNTATCVLGRLADALHRLQTYPRTNTGSNTY | (SEQ ID NO: 231) |
| KCNTATCVLGRLAAFLHRLQTYPRTNTGSNTY | (SEQ ID NO: 232) |
| SCNTATCVLGRLADFLHRLQTYPRTNTGSNTY | (SEQ ID NO: 233) |
| KCNTATCVLGRLSQELHRLQTMPRTNTGSNTY | (SEQ ID NO: 234) |
| KCNTATCVLGRLSQELHRLQTVPRTNTGSNTY | (SEQ ID NO: 235) |
| KCNTATCVLGRLNEYLHRLQTYPRTNTGSNTY | (SEQ ID NO: 236) |
| SCNTATCVLGRLSQELHRLQTYPRTNTGSNTY | (SEQ ID NO: 237) |
| KCNTATCVLGRLTEFLHRLQTYPRTNTGSNTY | (SEQ ID NO: 238) |
| KCNTATCVLGRLAEFLHRLQTYPRTNTGSNTY | (SEQ ID NO: 239) |
| KCNTATCVLGRLTDYLHRLQTYPRTNTGSNTY | (SEQ ID NO: 240) |
| KCNTATCVLGRLAQFLHRLQTYPRTNTGSNTY | (SEQ ID NO: 241) |
| KCNTATCVLGRLADFLHRFQTFPRTNTGSNTY | (SEQ ID NO: 242) |
| KCNTATCVLGRLADFLHRFHTFPRTNTGSNTY | (SEQ ID NO: 243) |
| KCNTATCVLGRLADFLHRFQTFPRTNTGSGTP | (SEQ ID NO: 244) |
| CNTATCVLGRLADFLHRLQTYPRTNTGSNTY | (SEQ ID NO: 245) |
| KCDTATCVLGRLSQELHRLQTYPRTNTGSNTY | (SEQ ID NO: 246) |
| KCNTATCVLGRLFDFLHRLQTYPRTNTGSNTY | (SEQ ID NO: 247) |
| KCNTATCVLGRLAAALHRLQTYPRTNTGSNTY | (SEQ ID NO: 248) |
| TCDTATCVLGRLSQELHRLQTYPRTNTGSNTY | (SEQ ID NO: 249) |
| CSNLSTCATQRLANELVRLQTYPRTNVGSNTY | (SEQ ID NO: 250) |
| KCNTATCATQRLANELVRLQTYPRTNYGSNTY | (SEQ ID NO: 251) |
| CSNLSTCVLGRLSQELHRLQTYPRTNTGSNTY | (SEQ ID NO: 252) |
| KCNTATCVLGRLSQELHRLQTYPRTNTGSNTY. | (SEQ ID NO: 253) |

In some embodiments, compounds comprising the amino acid sequence KCNTATCVLGRLSQELHRLQTYPRT-NTGSNTY (SEQ ID NO:253) are of particular use in the disclosed methods.

As described herein, amylin family peptide hormones useful in the compositions and methods disclosed herein also include adrenomedullin (ADM) peptides. By "adrenomedullin" or "ADM" is meant the human peptide hormone and species variants thereof. ADM is generated from a 185 amino acid preprohormone through consecutive enzymatic cleavage and amidation. This process culminates in the liberation of a 52 amino acid bioactive peptide. Any known ADM peptide, analog, or derivative that exhibits biological activity known in the art may be used in the compositions and methods disclosed herein. In one embodiment, the ADM peptides, analogs, and derivatives have at least one hormonal activity of native ADM peptide. In certain embodiments, the ADM peptides, analogs, and derivatives are agonists of a receptor which native ADM is capable of specifically binding.

As described herein, amylin family peptide hormones useful in the compositions and methods disclosed herein also include calcitonin (CT) peptides. By "calcitonin" or "CT" is meant the human peptide hormone and species variants thereof, including salmon calcitonin (sCT). CT is a 32 amino acid peptide cleaved from a larger prohormone. It contains a single disulfide bond, which causes the amino terminus to assume the shape of a ring. Native CT peptides are known in the art, as are functional CT peptide analogs, derivatives, and hybrids. Any CT peptide, analog, or derivative known in the art that exhibits biological activity known in the art may be used in the compositions and methods disclosed herein. In one embodiment, the CT peptides, analogs, and derivatives have at least one hormonal activity of native CT peptide. In certain embodiments, the CT peptides, analogs, and derivatives are agonists of a receptor which native CT is capable of specifically binding. CT peptide analogs, derivatives, and hybrids may be amidated as known in the art or may be in the acid form. Exemplary CT analogs and derivatives include, but are not limited to, those disclosed in U.S. Pat. Nos. 4,652,627, 4,606,856, 4,604,238, 4,597,900, 4,537,716, 4,497,731, 4,495,097, 4,444,981, 4,414,149, 4,401,593, and 4,397,780, which are hereby incorporated by reference.

As described herein, amylin family peptide hormones useful in the compositions and methods disclosed herein also include calcitonin gene related peptide (CGRP). By "calcitonin gene related peptide" or "CGRP" is meant the human peptide hormone and species variants thereof, in any physiological form. CGRP is a 37 amino acid peptide and is encoded and expressed from alternative splicing of calcitonin pre-mRNA. Any CGRP, CGRP analog, or CGRP derivative known in the art that exhibits biological activity known in the art may be used in the compositions and methods disclosed herein. In one embodiment, the CGRP peptides, analogs, and derivatives have at least one hormonal activity of native CGRP. In certain embodiments, the CGRP peptides, analogs, and derivatives are agonists of a receptor which native CGRP is capable of specifically binding. CGRP peptides, analogs, and derivatives may be amidated as known in the art or may be in the acid form. Exemplary CGRP analogs and derivatives include, but are not limited to, those disclosed in U.S. Pat. Nos. 4,697,002; and 4,687,839, which are hereby incorporated by reference.

Derivatives of the agonists and analogs are also included within the methods provided in which the stereochemistry of individual amino acids may be inverted from (L)/S to (D)/R at one or more specific sites. Also included within the methods provided are the agonists and analogs modified by glycosylation of Asn, Ser and/or Thr residues. Compounds useful in the methods provided may also be biologically active fragments of the peptides (native, agonist, analog, and derivative) herein described.

Agonist and analogs of amylin that contain less peptide character are included within the methods provided. Such peptide mimetics may include, for example, one or more of the following substitutions for —CO—NH—amide bonds: depsipeptides (—CO—O—), iminomethylenes (—CH$_2$—NH—), trans-alkenes (—CH═CH—), beta-enaminonitriles (—C(═CH—CN)—NH—), thioamides (—CS—NH—), thiomethylenes (—S—CH$_2$— or —CH$_2$—S—), methylenes (—CH$_2$—C2-) and retro-amides (—NH—CO—).

Compounds for use in the methods provided form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). In certain embodiments, the compounds form acetate, hydrochloride, and trifluoroacetate salts.

Amylin agonists useful in the compositions and methods provided herein may also include fragments of amylin and its analogs as described above as well as those described in EP 289287, the contents of which are herein incorporated by reference. Amylin agonists analogs may also be compounds having at least 60, 65, 70, 75, 80, 85, 90, 95, or 99% amino acid sequence identity to SEQ ID NO:1, or any of the amylin analogs specifically described herein having amylin activity. Amylin agonists also include small chemical molecules and non-peptide molecules, for example those based on small molecule chemistry. In some embodiments, amylin agonists are not small chemical molecules.

Derivatives of the amylin family peptides or analogs are also known in the art. Such derivatives include amylin family peptide hormones and analogs thereof conjugated to one or more water soluble polymer molecules, such as polyethylene glycol (PEG) or fatty acid chains of various lengths (e.g., stearyl, palmitoyl, octanoyl, etc.), or by the addition of polyamino acids, such as poly-his, poly-arg, poly-lys, poly-ala, and combinations of polyamino acids, such as poly-his-ala, poly-arg-ala, and poly-lys-ala. Modifications to the peptides or analogs thereof can also include small molecule substituents, such as short alkyls and constrained alkyls (e.g., branched, cyclic, fused, adamantyl), and aromatic groups. As described herein, such polymer-conjugations and small molecule substituent modifications may occur singularly at the N- or C-terminus or at the side chains of amino acid residues within the peptide. Alternatively, there may be multiple sites of derivatization along the peptide. Substitution of one or more amino acids with lysine, aspartic acid, glutamic acid, or cysteine may provide additional sites for derivatization. See, e.g. U.S. Pat. Nos. 5,824,784 and 5,824,778. In some embodiments, the peptides may be conjugated to one, two, or three polymer molecules.

Exemplary water soluble polymer molecules will have a molecular weight ranging from about 500 to about 20,000 Daltons. In some instances, the water soluble polymer molecules are linked to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In some embodiments, the peptides are linked to one, two, or three PEG molecules through an epsilon amino group on a lysine amino acid.

Derivatives also include amylin family peptide hormones or analogs with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the peptide. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In one embodiment, cyclization can be through the formation of disulfide bridges. Alternatively, there may be multiple sites of chemical alteration along the peptide.

"Amylin activity" as used herein may include at least one of the activities known in the art as described below. Amylin activity may also include the ability of amylin to modify food preference, modify binge eating, modify food cravings, or any combination thereof. In general, amylin agonists or amylin agonist analogs are recognized as referring to compounds which, by directly or indirectly interacting or binding with one or more receptors, mimics an action of amylin. They may also be referred to as amylinomimetics.

Activity as amylin agonists and/or analogs can be confirmed and quantified by performing various screening assays, including the nucleus accumbens receptor binding assay, the soleus muscle assay, a gastric emptying assay, or by the ability to induce hypocalcemia or reduce postprandial hyperglycemia in mammals. Methods of testing compounds for amylin activity are known in the art. Exemplary screening methods and assays for testing amylin agonists are described in U.S. Pat. Nos. 5,264,372 and 5,686,411, which are incorporated herein by reference.

The receptor binding assay, a competition assay that measures the ability of compounds to bind specifically to membrane-bound amylin receptors. A source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand, are analyzed by computer using analyses by nonlinear regression to a 4-parameter logistic equation (INPLOT program, GraphPAD Software, San Diego, Calif.) or the ALLFIT program of DeLean et al. (ALLFIT, Version 2.7 (NIH, Bethesda, Md. 20892)). Munson et al. (1980) *Anal. Biochem.* 107:220-239.

Assays of biological activity of amylin agonists/analogs in the soleus muscle may be performed using previously described methods (Leighton et al. (1988) *Nature* 335:632-635; Cooper et al. (1988) *Proc. Natl. Acad. Sci. USA* 85:7763-7766), in which amylin agonist activity may be assessed by measuring the inhibition of insulin-stimulated glycogen synthesis. In brief, an exemplary method includes soleus muscle strips prepared from 12-h fasted male Wistar rats. The tendons of the muscles are ligated before attachment to stainless steel clips. Muscle strips are pre-incubated in Erlemneyer flasks containing 3.5 ml Krebs-Ringer bicarbonate buffer, 7 mM N-2-hydroxyethyl-peperazine-N'-2-ethane-sulphonic acid, pH 7.4, and 5.5 mM pyruvate. Flasks are sealed and gassed continuously with $O_2$ and $CO_2$ in the ratio 19:1 (v/v).

After pre-incubation of muscles in this medium for 30 min at 37° C. in an oscillating water bath, the muscles strips are transferred to similar vials containing identical medium (except pyruvate) with added [U-14C] glucose (0.5 µCi/ml) and insulin (100 µU/ml). The flasks are sealed and re-gassed for an initial 15 min in a 1-h incubation. At the end of the incubation period, muscles are blotted and rapidly frozen in liquid $N_2$. The concentration of lactate in the incubation medium can be determined spectrophotometrically and [U-14C] glucose incorporation in glycogen measured.

Methods of measuring the rate of gastric emptying are disclosed in, for example, Young et al. (1995) *Diabetologia* 38:642-648. In a phenol red method, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Amylin agonist compounds may exhibit activity in the receptor binding assay on the order of less than about 1 to 5 nM, in some embodiments less than about 1 nM and in some embodiments less than about 50 pM. In the soleus muscle assay, amylin agonist compounds may show $EC_{50}$ values on the order of less than about 1 to 10 micromolar. In the gastric emptying assays, amylin agonist compounds show $ED_{50}$ values on the order of less than 100 µg/rat.

The peptides described herein may be prepared using chemical peptide synthesis techniques known in the art, e.g., using an automated or semi-automated peptide synthesizer, standard recombinant techniques, or both. Likewise, the derivatives of the peptides may be produced using standard chemical, biochemical, or in vivo methodologies.

The peptides may be synthesized in solution or on a solid support in accordance with conventional techniques. Various automated synthesizers are commercially available and may be used in accordance with known protocols. See, e.g., Stewart et al. (1984) *Solid Phase Peptide Synthesis*, 2d. ed., Pierce Chemical Co.; Tam et al. (1983) *J. Am. Chem. Soc.* 105: 6442; Merrifield (1986) *Science* 232: 341-347; and Barany et al. (1979) *The Peptides*, Gross et al., eds., Academic Press, NY, 1-284. Solid phase peptide synthesis may be carried out using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) as examples. For example, solid phase peptide synthesis may be carried out with an automated peptide synthesizer (e.g. Model 430A, Applied Biosystems Inc., Foster City, Calif.) using the NMP/HOBt (Option 1) system and tBoc or Fmoc chemistry with capping (see, Applied Biosystems User's Manual for the ABI 430A Peptide Synthesizer, Version 1.3B Jul. 1, 1988, section 6:49-70). Peptides may also be assembled using an Advanced ChemTech Synthesizer (Model MPS 350, Louisville, Ky.). Peptides may be purified by RP-HPLC (preparative and analytical) using, e.g., a Waters(g) DELTA-PREP™ 3000 system (Waters Corp., Milford, Mass.) and a C4, C8, or C18 preparative column (10μ, 2.2×25 cm; Grace Vydac, Hesperia, Calif.). The peptide can be readily synthesized and then screened in assays designed to identify peptides with particular activities. Other methods of synthesizing and purifying peptides are known to the skilled artisan.

The peptides disclosed herein may alternatively be produced by recombinant techniques well known in the art. See, e.g., Sambrook et al. (1989) *Molecular Cloning: A Laboratory Manual*, 2d ed., Cold Spring Harbor, N.Y. The peptides produced by recombinant technologies may be expressed from a polynucleotide. One skilled in the art will appreciate that the polynucleotides, including DNA and RNA, that encode such the various fragments of the peptides may be obtained from the wild-type cDNA, taking into consideration the degeneracy of codon usage, or may be engineered as desired. These polynucleotide sequences may incorporate codons facilitating transcription and translation of mRNA in microbial hosts. Such manufacturing sequences may readily be constructed according to the methods well known in the art. The polynucleotides above may also optionally encode an N-terminal methionyl residue. The polynucleotides above may also optionally encode a C-terminal glycyl residue for proper amide formation. Non-peptide compounds useful in composition and methods provided herein may be prepared by art-known methods. For example, phosphate-containing amino acids and peptides containing such amino acids may be prepared using methods known in the art. See, e.g., Bartlett et al. (1986) *Bioorg. Chem.* 14: 356-377.

A variety of cell types may be used to contain and express a peptide coding sequence including, for example, bacteria, yeast, algae, insect cells, plant cells, and animal cells such as mammalian and avian cells. A variety of expression vector/host systems may be used, including, but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus (CaMV); tobacco mosaic virus (TMV) or transformed with bacterial expression vectors (e.g., Ti or pBR322 plasmid); or animal cell systems. Mammalian cells and cell lines that are useful in recombinant protein productions include, but are not limited to, VERO (African green monkey kidney) cells, HeLa cells, Chinese hamster ovary (CHO) cell lines, COS cells (such as COS-7), WI38 (human lung fibroblasts), baby hamster kidney (BHK) cells, HepG2, 3T3, RIN, Madin-Darby canine kidney epithelial (MDCK) cells, A549, PC12, K562 and 293 cells. Exemplary protocols for the recombinant expression of polypeptides are well known in the art.

Host cell strains may be chosen for a particular ability to process the expressed peptide or produce certain post-translation modifications that will be useful in providing peptide activity. Such modifications of the polypeptide include, but are not limited to, acetylation, carboxylation, glycosylation, phosphorylation, lipidation, acylation, and amidation, for example, carboxy-terminal amidation. Post-translational processing, which cleaves a "prepro" form of the polypeptide, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Peptides described herein may be produced using a combination of both automated peptide synthesis and recombinant techniques. For example, a peptide may contain a combination of modifications including deletion, substitution, and insertion by PEGylation. Such a peptide may be produced in stages. For example, in the first stage, an intermediate peptide containing the modifications of deletion, substitution, insertion, and any combination thereof, may be produced by recombinant techniques as described. Then, after an optional purification step, the intermediate peptide is PEGylated through chemical modification with an appropriate PEGylating reagent (e.g., from Nektar Therapeutics, San Carlos, Calif.) to yield the desired peptide. Amidation of a peptide may also be done in stages. One skilled in the art will appreciate that the above-described procedure may be generalized to apply to a peptide containing a combination of modifications selected from deletion, substitution, insertion, derivation, and other means of modification well known in the art and contemplated herein.

Peptides described herein may also be produced using chemical ligation schemes known in the art, including those described, for example, in U.S. Application Publication Nos. 2003-0191291, 2003-0208046, and 2004-0115774. Chemical ligation refers to a chemoselective reaction involving the covalent joining of two chemical moieties, each of which moieties bears a mutually reactive functional group that is uniquely capable of forming a non-reversible covalent bond with the other. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible unique, mutually reactive, C-terminal and N-terminal amino acid residues. Chemical ligation includes covalent ligation of (1) a first peptide or polypeptide bearing a uniquely reactive C-terminal group with (2) a second peptide or polypeptide bearing a uniquely reactive N-terminal group, where the C-terminal and N-terminal reactive groups form a non-reversible covalent bond therein between. It also includes N-terminal to N-terminal and C-terminal to C-terminal ligation. In particular, chemical ligation includes any chemoselective reaction chemistry that can be applied to ligation of unprotected peptide segments. Several different chemistries have been utilized for this purpose, examples of which include native chemical ligation, oxime forming chemical ligation, thioester forming ligation (Schnolzer et al. (1992) *Science* 256:221-225; Gieselman et al. (2001) *Org. Lett.* 3:1331-1334), thioether forming ligation (Englebretsen et al. (1995) *Tot. Leffs.* 36:8871-8874), hydrazone forming ligation (Gaertner, et al. (1994) *Bioconj. Chem.* 5:333-338), and thiazolidine forming ligation and oxazolidine forming ligation (Zhang et al. (1998) *Proc. Natl. Acad. Sci. USA* 95:9184-9189; PCT Publication No. WO 95/00846; U.S. Pat. No. 5,589,356); and Staudinger amide forming chemical ligation (Saxon et al. (2000) *Org. Leff.* 2:2141-2143).

Reaction conditions for a given ligation chemistry are generally selected to maintain the desired interaction of the peptide or polypeptide segments employed for ligation. For example, pH and temperature, water-solubility of the ligation components, ratio of the first segment to the second segment, water content and composition of the reaction mixture can be varied to optimize ligation. Addition or exclusion of reagents that solubilize the ligation segments to different extents may further be used to control the specificity and rate of the desired ligation reaction, i.e., control exposure and presentation of reactive groups by manipulating solubility of the peptide or polypeptide segments. Reaction conditions are readily determined by assaying for the desired chemoselective reaction product compared to one or more internal and/or external controls. These methodologies have proven a robust methodology for generating a native amide bond at the ligation site.

In conjunction with the design of the peptide, the peptides or polypeptide segments utilized for synthesizing the polypeptide backbone are constructed. Methods useful in the synthesis of peptides and polypeptides backbones are described in, for example, U.S. Application Publication Nos. 2004-0138412 (extended native chemical ligation), 2003-0208046 (pseudo-native chemical ligation), 2005-0261473 (carboxy protection strategies for acidic C-terminal amino acids in chemical ligation to eliminate formation of unwanted side products), 2005-0064538 and 2005-0113563 (native chemical ligation with improved efficiency of ligation and chemical ligation with three or more components); in PCT Application Publication Nos. WO2004/105685 (aqueous-compatible solid phase chemical ligation using a displaceable linker) and WO2004/060925 (multiplex polymer ligation with water-soluble polymeric protecting groups and their replacement with desired adducts); and in U.S. Pat. Nos. 6,307,018 and 6,184,344 (native chemical ligation), 6,326,468 (solid phase native chemical ligation), 6,217,873 (polyoxime compounds), 6,174,530 (homogenous polyoxime compositions), 6,001,364 (hetero-polyoxime compounds), and 6,451,543 (lipid-matrix assisted synthesis). In general, synthesis of a peptide or polypeptide backbone by chemical ligation involves selection of suitable ligation sites that are chosen based on the ligation chemistry selected for assembling the various polypeptide backbone segments, the reversible (or cleavable) polymer attachment chemistry chosen for a given target peptide, and the particular polymer attachment sites. When native chemical ligation is employed, cysteine ligation sites are determined by scanning the target polypeptide backbone amino acid sequence for suitable naturally occurring cysteine residue. When "extended native chemical ligation" is employed, ligation sites can be selected by scanning the target polypeptide backbone amino acid sequence for suitable naturally occurring ligation site junctions that permit robust ligations. Because extended native chemical ligation is not limited to ligation at cysteine residues, any number of residues may serve as the ligation site junction. In some instances, a combination of native and extended native chemical ligation may be part of the design.

In one embodiment, native chemical ligation is used to generate part or all of the full-length polypeptide chain. Cysteines present in the naturally occurring peptide backbone can be used as the chemical ligation sites. Alternatively, where a desired ligation junction is devoid of a suitable cysteine, the non-cysteine amino acid at that position can be replaced with a cysteine or a cysteine can be inserted so as to permit native chemical ligation at that site. If desired, the newly introduced cysteine can be converted to a pseudo amino acid residue corresponding to the original amino acid at that position. Formation of a pseudo amino acid by conversion of a cysteine at native chemical ligation sites is referred to "pseudo native chemical ligation." Alternatively, when the cysteine is introduced at a site for polymer protecting group modification, the side chain thiol can be exploited for the attachment of a thiol reactive water-soluble polymer construct, provided that all other cysteines in the target polypeptide that one does not wish to modify are protected. In another embodiment, extended native chemical ligation can be utilized to generate part or all of the full-length polypeptide. Peptides used for thioester-mediated ligation, such as for native chemical ligation, can be made following standard protocols as well, for example see U.S. Pat. Nos. 6,307,018 and 6,184,344.

As used herein, the term "purified peptide" is intended to refer to a composition, isolated from other components, wherein the peptide is purified to any degree relative to its naturally obtainable state. A purified peptide therefore also refers to a peptide, free from the environment in which it may naturally occur. Generally, "purified" will refer to a peptide composition that has been subjected to fractionation to remove various other components, and which composition substantially retains a biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

It may be desirable to purify the peptides generated by the methods described herein. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Purification techniques include, for example, precipitation with ammonium sulfate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of the peptide. In some embodiments, a combination of anion exchange and immunoaffinity chromatography may be used to produce purified peptide compositions described herein.

The amylin, amylin agonists, amylin analogs, and amylin derivatives (herein referred to in this section as the "amylin compounds") may be administered alone or in combination with pharmaceutically acceptable carriers or excipients, in either single or multiple doses. Accordingly, pharmaceutical compositions are provided comprising a therapeutically or prophylactically effective amount of at least one amylin compound or a pharmaceutically acceptable salt thereof, together with pharmaceutically acceptable diluents, preservatives, solubilizers, emulsifiers, adjuvants, and/or carriers useful in the delivery of the amylin compounds. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang et al. (1988) *Journal of Parenteral Science and Technology* Technical Report No. 10, Supp. 42:2 S. Exemplary formulations for an amylin or amylin agonist can be found in U.S. Pat. No. 6,410,511 and U.S. Pat. Application Publication No. 2003-0092606, which are incorporated herein by reference.

One exemplary use provided herein is to peripherally administer such amylin compounds for the treatment or prevention of binge eating. Another exemplary use provided herein is to peripherally administer such amylin compounds for modifying food preference or food cravings. Another exemplary use provided herein is to peripherally administer such amylin compounds for modifying metabolic rate of a subject.

In general, the compounds may be formulated into a stable, safe pharmaceutical composition for administration to a patient. Pharmaceutical formulations contemplated for use in the methods described herein may comprise approximately 0.01 to 6.0% (w/v), or 0.05 to 1.0%, of the compound; approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl-, ethyl-, propyl- and butyl-parabens and phenol. Such a preservative is generally included if the formulated peptide is to be included in a multiple use product.

In a particular embodiment, a pharmaceutical formulation may contain a range of concentrations of the compound, e.g., between about 0.01% to about 98% (w/v), or between about 1 to about 98% (w/v), or between 80% and 90% (w/v), or between about 0.01% to about 50% (w/v), or between about 10% to about 25% (w/v) in this embodiment. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the formulation. An excipient may be included in the presently described formulations at various concentrations. For example, an excipient may be included in the concentration range from about 0.02% to about 20% (w/w), about 0.02% and 0.5% (w/w), about 0.02% to about 10% (w/w), or about 1% to about 20% (w/w). In addition, similar to the present formulations themselves, an excipient may be included in solid (including powdered), liquid, semi-solid or gel form.

As described herein, a variety of liquid vehicles are suitable for use in the present peptide formulations, for example, water or an aqueous/organic solvent mixture or suspension. The pharmaceutical formulations may be composed in various forms, e.g., solid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it. In some embodiments, the amylin compound is suspended in an aqueous carrier, for example, an isotonic buffer solution at a pH of about 3.0 to about 8.0, at a pH of about 3.5 to about 7.4, at a pH of about 3.5 to about 6.0, or at a pH of about 3.5 to about 5.0. In certain embodiments, the pH of the formulation is maintained in the range of about 3.5 to about 5.0, or about 3.5 to about 6.5, or about 3.7 to about 4.3, or about 3.8 to about 4.2. A particular pH may be about 4.0. While not seeking to be bound by this theory, it is presently understood that, in some embodiments, where the pH of the pharmaceutical formulation exceeds 5.5, chemical degradation of the peptide may be accelerated such that the shelf life is less than about two years.

Useful buffers include sodium citrate/citric acid, and sodium phosphate/phosphoric acie, and sodium acetate/acetic acid buffers. In certain embodiments, the buffer with the amylin compound is an acetate buffer (for example, at a final formulation concentration of from about 1-5 mM, e.g., 1.5 mM, to about 60 mM), a phosphate buffer (for example, at a final formulation concentration of from about 1-5 mM, e.g., 1.5 mM, to about 30 mM) or a glutamate buffer (for example, at a final formulation concentration of from about 1-5 mM, e.g., 1.5 mM, to about 60 mM). In some embodiments, the buffer is acetate (for example, at a final formulation concentration of from about 5 mM to about 30 mM).

A stabilizer may be included in the present formulation but, and importantly, is not necessarily needed. If included, however, a stabilizer useful in the practice of the present formulation is a carbohydrate or a polyhydric alcohol. A suitable stabilizer useful in the practice of the present methods is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. In embodiments in which the subjects have diabetes, suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic subjects (e.g., treating obesity or binge eating).

In certain embodiments, if a stabilizer is included, the compound is stabilized with a polyhydric alcohol such as sorbitol, mannitol, inositol, glycerol, xylitol, and polypropylene/ethylene glycol copolymer, as well as various PEGs of molecular weight 200, 400, 1450, 3350, 4000, 6000, and 8000). Mannitol is an example of a particular polyhydric alcohol. Another useful feature of the lyophilized formulations described herein is the maintenance of the tonicity of the lyophilized formulations with the same formulation component that serves to maintain their stability. Mannitol is a particular polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Anti-microbial agents should be evaluated to ensure compatibility with all other components of the formula, and their activity should be evaluated in the total formula to ensure that a particular agent that is effective in one formulation is not ineffective in another. It is not uncommon to find that a particular anti-microbial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide. The prevention of the action of microorganisms can be brought about by various antibacterial and antifungal agents, for example, parabens, chlorobutanol, phenol, sorbic acid, thimerosal, and the like. While the preservative for use in the pharmaceutical compositions can range from 0.005 to 1.0% (w/v), the typical range for each preservative, alone or in combination with others, is: benzyl alcohol (0.1-1.0%), or m-cresol (0.1-0.6%), or phenol (0.1-0.8%) or combination of methyl (0.05-0.25%) and ethyl- or propyl- or butyl- (0.005%-0.03%) parabens. The parabens are lower alkyl esters of parahydroxybenzoic acid. A detailed description of each preservative is set forth in "Remington's Pharmaceutical Sciences" as well as Pharmaceutical Dosage Forms: Parenteral Medications, Vol. 1, 2nd ed., Avis et al. Ed., Mercel Dekker, New York, N.Y. (1992).

While not intending to be so limited, pramlintide, $^{25,25,29}$Pro-h-amylin, does not have a tendency to adsorb onto the glass in a glass container when in a liquid form, therefore, a surfactant is not required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio]1-propanesulfonate), BRIJ® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations typically may be isotonic or substantially isotonic.

A suitable vehicle for parenteral products is water. Water of suitable quality for parenteral administration can be prepared either by distillation or by reverse osmosis. Water for injection is the preferred aqueous vehicle for use in the pharmaceutical injectable formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation provided herein.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Form a Vitrum. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

In order to permit introduction of a needle from a hypodermic syringe into a multiple-dose vial and provide for resealing as soon as the needle is withdrawn, the open end of each vial is typically sealed with a rubber stopper closure held in place by an aluminum band. Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. These stoppers pass the stopper integrity test when tested using patient use patterns, e.g., the stopper can withstand at least about 100 injections. Alternatively, the peptide can be lyophilized in vials, syringes or cartridges for subsequent reconstitution. Liquid formulations provided herein can be filled into one or two chambered cartridges, or one or two chamber syringes.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (for example, preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation provided herein. Typical sterilization processes include filtration, steam (moist heat), dry heat, gases (e.g., ethylene oxide, formaldehyde, chlorine dioxide, propylene oxide, beta-propiolaectone, ozone, chloropicrin, peracetic acid methyl bromide and the like), exposure to a radiation source, and aseptic handling. Filtration is an exemplary method of sterilization for liquid formulations described herein. The sterile filtration involves filtration through 0.45 μm and 0.22 μm (1 or 2) which may be connected in series. After filtration, the solution is filled into appropriate vials or containers.

In one embodiment, the pharmaceutical formulations are intended for parenteral administration. Suitable routes of administration include intramuscular, intravenous, subcutaneous, intradermal, intraarticular, intrathecal, intramammary, retrobulbar, intrapulmonary (e.g., controlled release), transdermal, and the like. The subcutaneous route of administration is one particular route. Mucosal delivery is also particularly suitable. These mucosal routes include, but are not limited to, oral, nasal, sublingual, pulmonary, anal, vaginal, and buccal routes which may include administration of the peptide in liquid, semi-solid or solid form. Administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The amylin compounds may be provided in dosage unit form containing an amount of the compound that will be effective in one or multiple doses to treat or help in treating the subject in need thereof. Parenteral administration may be carried out with an initial bolus followed by continuous infusion to maintain therapeutic circulating levels of drug product. A form of repository or "depot" slow release preparation may be used so that therapeutically effective amounts of the preparation are delivered into the bloodstream over many hours or days following transdermal injection or delivery. Those of ordinary skill in the art will readily optimize effective dosages and administration regimens as determined by good medical practice and the clinical condition of the individual patient, taking into consideration, for example, the age and weight of the patient, the patient's physical condition, and the condition to be treated.

Typically, a dosage of between about 0.001 μg/kg body weight/day to about 1000 μg/kg body weight/day may be used, but more or less, as a skilled practitioner will recognize, may be used. Typical doses may contain from a lower limit of about 0.5 μg, 1 μg, 5 μg, 10 μg, 50 μg to 100 μg to an upper limit of about 100 μg, 500 μg, 1 mg, 5 mg, 10 mg, 50 mg or 100 mg of the pharmaceutical compound per day. Also contemplated are other dose ranges such as 0.1 μg to 1 mg of the compound per dose. Thus, exemplary doses may be 30, 60, 120, 240, or 360 μg of the compound per dose. The doses per day may be delivered in discrete unit doses or provided continuously in a 24 hour period, or any portion of that 24 hour period. The number of doses per day may be from 1 to about 4 doses per day, although it could be more. Dosing may be one or more times daily, or less frequently, such as one or more times weekly or one or more times monthly, and may be in conjunction with other compositions as described herein. It should be noted that the present methods and compositions are not limited to the dosages recited herein.

In some embodiments, an effective dose will typically be in the range of about 0.5 to 30 μg to about 5 mg/day, about 10 to 30 μg to about 2 mg/day, about 5 to 100 μg to about 1 mg/day, or about 5 μg to about 500 μg/day, for a 50 kg patient, administered in a single or divided doses. In some embodiments, dosages are between about 0.01 to about 100 μg/kg/dose. In other embodiments, the composition is formulation so as to deliver a dose of amylin compound ranging from 1 μg/kg to 100 mg/kg body weight/day or at doses ranging from 0.1 mg/kg to about 50 mg/kg body weight/day. Dosages for certain routes, for example oral administration, may be increased to account for decreased bioavailability, for example, by about 5-100 fold.

Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 μg to about 8 mg per day, whereas total dose/delivery of the pharmaceutical composition given s.c may be about 6 μg to about 16 or 24 mg per day.

The following Examples are provided to illustrate, but not limit, the invention.

EXAMPLES

Example 1

Synthesis of the Caloric Intake Lowering Polypeptides

The amylin and amylin peptide agonists can be synthesized using standard polypeptide synthesis methods. Such methods are described below and in U.S. Pat. Nos. 6,610,824 and 5,686,411, the entireties of which are incorporated herein by reference.

The polypeptides are assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles are used throughout the synthesis and Fast Moc (HBTU activation) chemistry is employed. However, at some positions coupling may be less efficient than expected and double couplings required. Deprotection (Fmoc group removal) of the growing peptide chain using piperidine likewise may not always be efficient and require double deprotection. Final deprotection of the completed peptide resin is achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.). The peptides are precipitated in ether/water (50 mL) and centrifuged. The precipitate is reconstituted in glacial acetic acid and lyophilized. The lyophilized peptides are dissolved in water and crude purity is then determined. Solvent A (0.1% TFA in water) and Solvent B (0.1% TFA in ACN) are used in purification and analysis steps. Solutions containing the various polypeptides are applied to a preparative C-18 column and purified (10% to 40% Solvent B in Solvent A over 40 minutes). Purity of fractions are determined isocratically using a C-18 analytical column. Pure fractions are pooled furnishing the above-identified peptide. Analytical RP-HPLC (gradient 30% to 60% Solvent B in Solvent A over 30 minutes) of the lyophilized peptide to determine retention time.

For example, amylin and amylin peptide agonists may be assembled on a Symphony peptide synthesizer (Protein Technologies, Inc.) using Rink amide resin (Novabiochem) with a loading of 0.43-0.49 mmol/g at 0.050-0.100 mmol. Fmoc amino acid (5.0 eq, 0.250-0.500 mmol) residues are dissolved at a concentration of 0.10 M in 1-methyl-2-pyrrolidinone. All other reagents (HBTU, 1-hydroxybenzotriazole hydrate and N,N-Diisopropylethylamine) are prepared as 0.55 M dimethylformamide solutions. The Fmoc protected amino acids are then coupled to the resin-bound amino acid using, HBTU (2.0 eq, 0.100-0.200 mmol), 1-hydroxybenzotriazole hydrate (1.8 eq, 0.090-0.18 mmol), N,N-diisopropylethylamine (2.4 eq, 0.120-0.240 mmol) for 2 hours. Following the last amino acid coupling, the peptide is deprotected using 20% (v/v) piperidine in dimethylformamide for 1 hour. Once peptide sequence is complete, the Symphony peptide synthesizer is programmed to cleave the resin. Trifluoroacetic acid (TFA) cleavage of the peptide from resin is carried out using 93% TFA, 3% phenol, 3% water and 1% triisopropylsilane for 1 hour. The cleaved peptide is precipitated using tert-butyl methyl ether, pelleted by centrifugation and lyophilized. The pellet is re-dissolved in water (10-15 mL), filtered and purified via reverse phase HPLC using a C18 column and an acetonitrile/water gradient containing 0.1% TFA. The resulting peptides are purified to homogeneity by reverse phase HPLC and the purity is confirmed by LCMS.

A general procedure for N-capping the peptides of the invention with fatty acids (e.g., octanoic and stearic acids) is as follows: Peptide on rink amide resin (0.1 mmol) is suspended in NMP (5 mL). In a separate vial, HBTU (0.3 mmol), HOBt (0.3 mmol) is dissolved in DMF (5 mL) followed by the addition of DIEA (0.6 mmol). This solution is added to the resin and this suspension is shaken for 2 hrs. The solvent is filtered and washed thoroughly with NMP (5 mL×4) and $CH_2Cl_2$ (20 mL), dried and is subjected to the TFA cleavage for 1 hr. The yield of the desired peptide is ca. 40 mg after cleavage and purification. PEG modification may be carried out in solution on a free epsilon-amino group of lysine or a terminal amino group of a purified peptide using commercially available activated PEG esters. The resulting PEGylated derivatives are purified to homogeneity by reverse phase HPLC and the purity is confirmed by LC/MS and MALDI-MS.

Example 2

Effect of Amylin on Sucrose Food Preference

The ability of amylin to modify food preference was examined in an animal model. Male, Sprague-Dawley® rats were submitted to a sugar withdrawal paradigm and observed for effects of stress on sugar intake. Briefly, rats were implanted with ALZET® osmotic pumps containing vehicle or rat amylin (300 µg/kg/d). All rats were provided with ad libitum access to standard chow, water, and a 30% sucrose drink. Subsequently, the sucrose drink was removed and half of the rats were subjected, daily, to 3 h of mild restraint stress for 3 successive days. After 3 days, sucrose was provided and its daily average consumption was measured over 4 days. Chow intake was also measured over the 3 days of withdrawal and stress and over the following 4 days when sucrose was re-introduced. No restraint was applied during the 4 days of sucrose re-introduction. Results of this assay are shown in FIG. 1(A-D) where * is P<0.05 by ANOVA and Fisher LSD post-hoc analyses.

In this model, chronic stress stimulates the proportion of total calories taken in as sugar (palatable feeding). As shown in FIG. 1A, stress induced by restraint significantly increased the average sucrose to chow consumption ratio (as % of baseline) (saline, R) over control consumption without stress inducement (saline, C). FIG. 1A also shows that amylin administration prevents the increase in the average sucrose to chow consumption ratio expected as a result of the stress induced by restraint. Compare the sucrose to chow ratio (expressed as a percentage of baseline) between amylin-administered stress-induced rats (amylin, R) and amylin-administered non-stressed control rats (amylin, C). Also compare the sucrose to chow ratio between amylin-administered stress-induced rats (amylin, R) and control vehicle (saline)-administered stress-induced rats (saline, R). As shown, amylin administration reduces this stress-induced palatable feeding response.

Figure 1B:
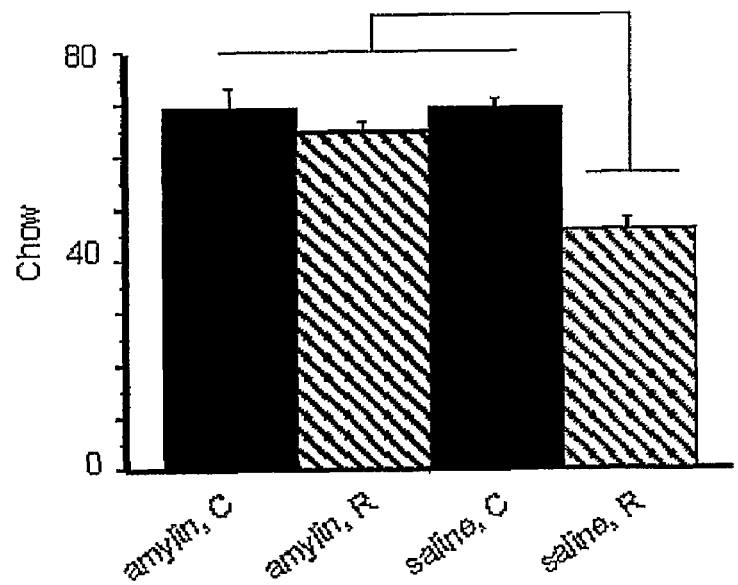
Figure 1C:
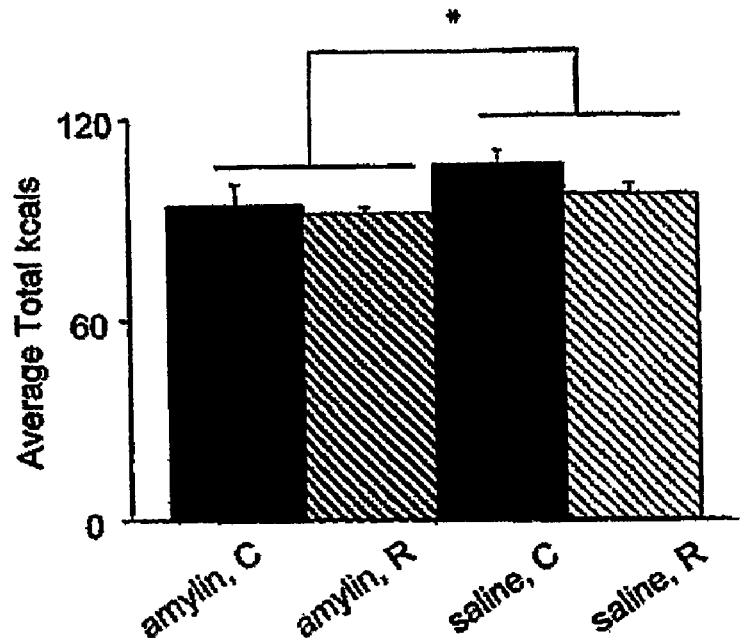
Figure 1D:
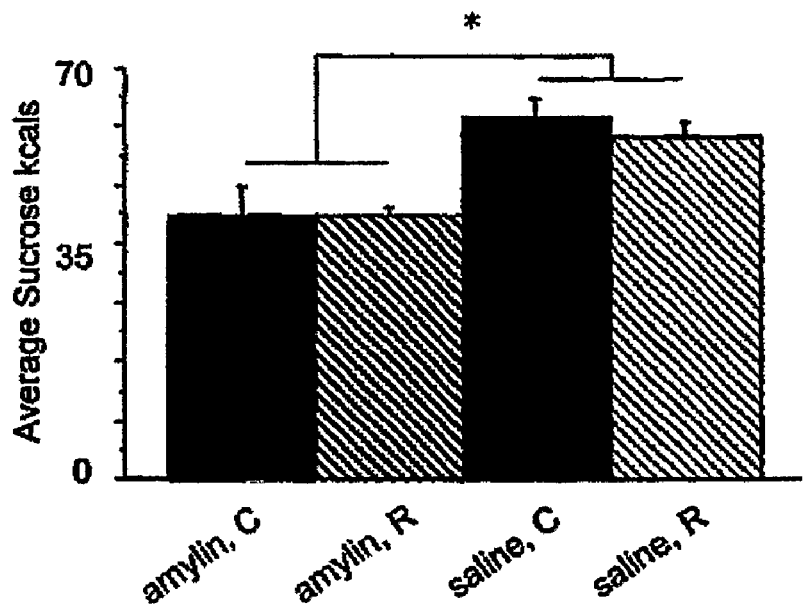

FIGS. 1B and 1C depicts the same results from the restraint stress assay from a different perspective, that of chow consumption and total kcals, respectively. FIGS. 1B and 1C show that the overall stress-induced decrease in chow intake and total kcals is less pronounced in the treatment group, as compared to the control group. FIG. 1D demonstrates that amylin decreases sucrose intake in both stressed and non-stressed conditions, as compared to the vehicle treated controls. In sum, it is believed that stress generally shifts the balance between diets rich in simple sugars or that are palatable and diets relatively low in simple sugars and fat (e.g., standard rat chow). Stress without amylin administration significantly decreased chow consumption in animals undergoing the stress of restraint (FIG. 1B), a typical response to stress. However, the treatment group with amylin administration appears to show a specific reduction in sucrose under both stressed and non-stressed conditions.

Example 3

Effect of Amylin on High Fat Food Preference

The ability of amylin to modify food preference was examined in an animal model. Adult male rats (490 g) were treated for 11 weeks with rat amylin (300 µg/kg/d) via osmotic pumps (#2ML4, Durect Corporation, Cupertino, Calif.) implanted subcutaneously, under anesthesia, in the interscapular region. Animals had access to both low fat chow (6% fat kcal, 54% cornstarch kcal; #7012, Harlan Teklad, Madison, Wis.) and high fat chow ("palatable chow") (58% fat kcal and 26% sucrose kcal; #D12311, Research Diets, New Brunswick, N.J.). Food intake and body weight were measured weekly. Just prior to treatment, and at the end of treatment, the amount of fat and lean tissue (expressed as g of tissue per 100 g of body weight) was measured via MRI (Echo MRI for rats, EchoMRI, Houston, Tex.).

Figure 2:
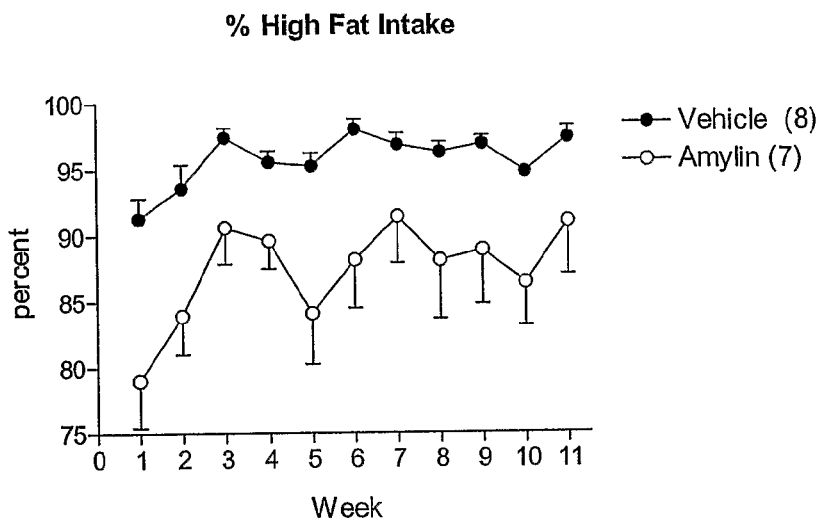
FIG. 2 is a graph depicting the effect of amylin on percentage of caloric intake from high fat chow.
Figure 3:
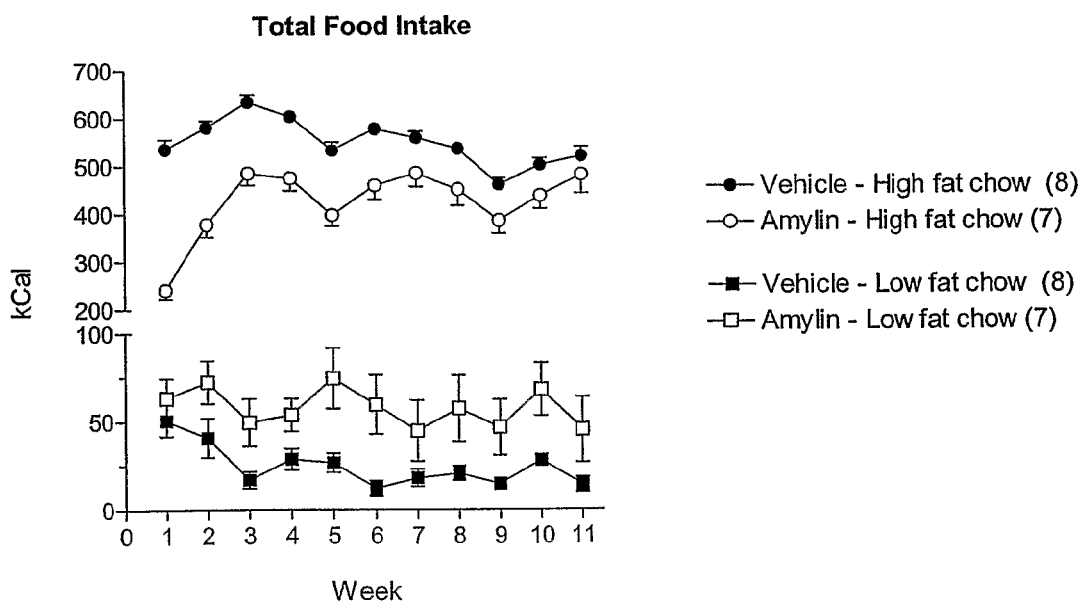
FIG. 3 is a graph depicting the effect of amylin on total caloric intake from high fat and low fat chow.

Results from these experiments are presented in FIGS. 2-5 in which the data are presented as means±SEM and the number of subjects in each group is shown in parentheses. As shown in FIG. 2, amylin-treated rats consumed a smaller percentage of total calories from the high fat chow than controls throughout the 11 weeks of treatment (vehicle=6315±111 kcal vs. amylin=5309±202 kcal (P's<0.05)). In terms of total food intake, amylin-treated rats obtained fewer calories from the high fat chow, and greater calories from the low fat chow, compared to vehicle-treated rats as shown in FIG. 3. The main effect for low fat chow was vehicle=271±42 kcal vs. amylin=633±145 kcal and the main effect for percent total calories was vehicle=4.3±0.6% vs. amylin=12.2±3.2% (P's<0.05).

Figure 4:
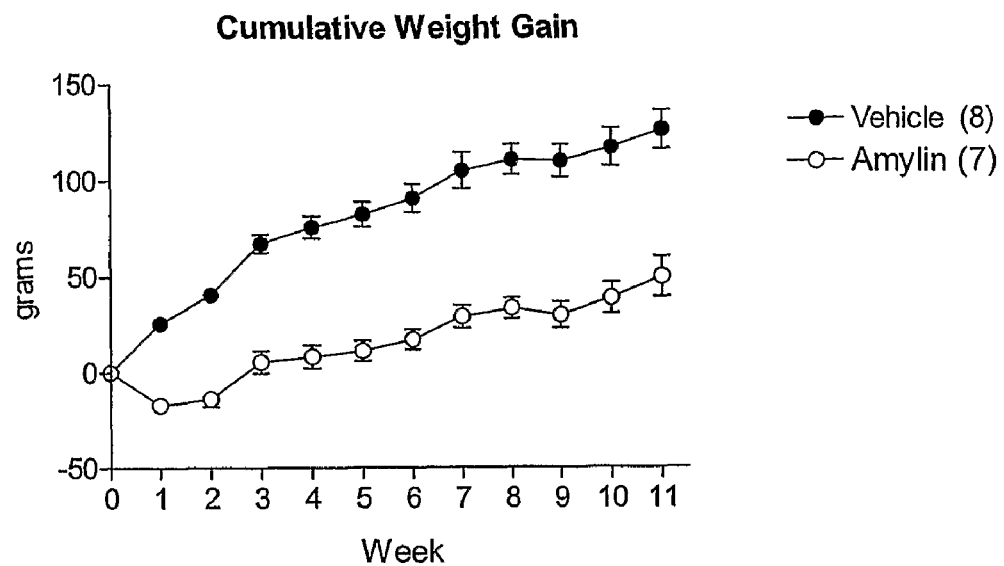
FIG. 4 is a graph depicting the effect of amylin on body weight gain in food preference study.
Figure 5:
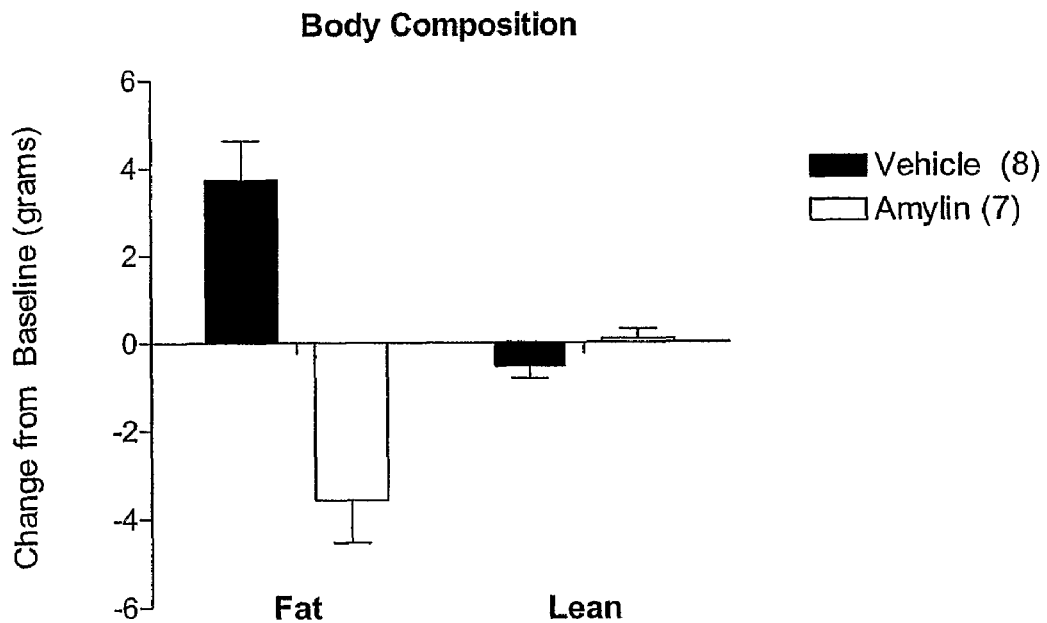
FIG. 5 is a graph depicting the effect of amylin on body composition in food preference study.

Throughout the treatment period, body weight gain was reduced with amylin treatment as shown in FIG. 4 (vehicle=126±10 g vs. amylin=50±11 g (P's<0.05)). Change in fat and lean tissue pre- and post-treatment was examined. As shown in FIG. 5, amylin administration decreased fat mass, but had no effect on lean tissue mass. For fat mass, the change in percent of total mass was 3.7±0.9% with vehicle and −3.6±1.0% with amylin (P<0.05). For lean tissue, the change in percent of total mass was −0.53±0.21% with vehicle and 0.08±0.23% with amylin (not significant).

Amylin administration also increased energy expenditure in the animals. Energy expenditure was assessed using an Oxymax animal monitoring system (Columbus Instruments, Columbus, Ohio) to measure oxygen consumption and carbon dioxide generation over time. From these measurements, heat (in kcal) was calculated and energy expenditure assessed. At 11 weeks, amylin increased 24 h energy expenditure (light phase increase=9.7%, dark phase increase=6.6%, P's<0.05) compared to controls.

The same study performed with an amylin agonist demonstrated that the amylin agonist was more effective than amylin in reduction of total caloric intake. Caloric intake from palatable food with the amylin agonist was roughly equivalent with amylin and caloric intake from low fat chow was less than that with amylin.

In terms of food preference, amylin-treated rats consumed a greater number of calories and a greater percentage of total calories from low fat chow compared to controls throughout the study. These results indicate that decreased caloric intake, with a relative preference for low fat chow vs. palatable chow, and increased energy expenditure contribute to the weight-lowering properties of amylin.

Example 4

Effect of Amylin Agonist on Satiation and on Binge Eating

The ability of the amylin agonist pramlintide to control or influence eating behavior was examined in human subjects. For the assessment, 24 hour-food intake (FI, ad-libitum meals), weight, feelings of hunger and fullness, and binge-eating (Binge Eating Scale, BES) were measured in a single-blind, placebo-controlled study. Obese subjects without eating disorders (50/50% female/male; BMI 35.61±3.98 kg/m$^2$, mean±SD) were randomized to six weeks of treatment with pramlintide or placebo. Pramlintide (180 μg) was administered subcutaneously three times per day (TID) prior to meals for 6 weeks and no lifestyle intervention was provided (TID evaluable N=59, placebo evaluable N=25). In another arm of the study, pramlintide was administered through continuous subcutaneous infusion (CSI) at 50 μg/h for 6 weeks and no lifestyle intervention was provided (CSI evaluable N=53, placebo evaluable N=22). A follow-up evaluation of the subjects was performed four weeks after cessation of the treatment. In addition to the measurement of food intake and weight, subjects were also assessed for the feelings of hunger and fullness over a 12-hour observation period on the day before treatment, the first day of treatment, and on Day 43. During the study, subjects were categorized by binge-eating severity as mild, moderate, or severe based on total BES scores.

After 6 weeks, subjects treated with pramlintide TID experienced significant placebo-corrected reductions from baseline in 24-hour food intake (−489±183 kcal; P<0.01) and weight (−2.2±0.5%; P<0.0001). In general, the mean hunger and fullness rating profiles were similar within each treatment group (pramlintide TID, pramlintide CSI, and pooled placebo) on the day before treatment, the first day of treatment, and on Day 43, and they were also similar across treatment groups. The hunger and fullness ratings were similar despite the fact that the mean total caloric intake was reduced by approximately 17% on the first day of treatment and 15% on Day 43 in pramlintide TID subjects and by approximately 22% on the first day of treatment and 7% on Day 43 in pramlintide CSI subjects compared with the pooled placebo group. Hence, less food intake was required in pramlintide-treated subjects to suppress hunger and to induce fullness levels similar to those in placebo-treated subjects. Accordingly, pramlintide enhances the satiating effect of meals.

Figure 6:
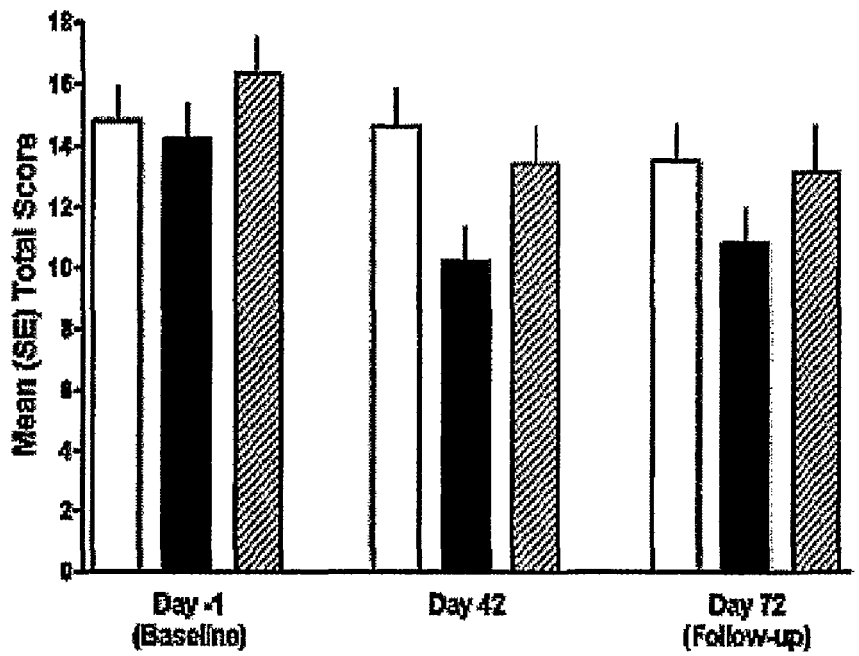
FIG. 6 is a graph depicting the effect of amylin on binge eating scale mean total score. The open bars represent all placebo recipients (n=53), the solid bars represent pramlintide TID recipients (n=59), and the hatched bars represent pramlintide CSI recipients (n=47).
Figure 7:
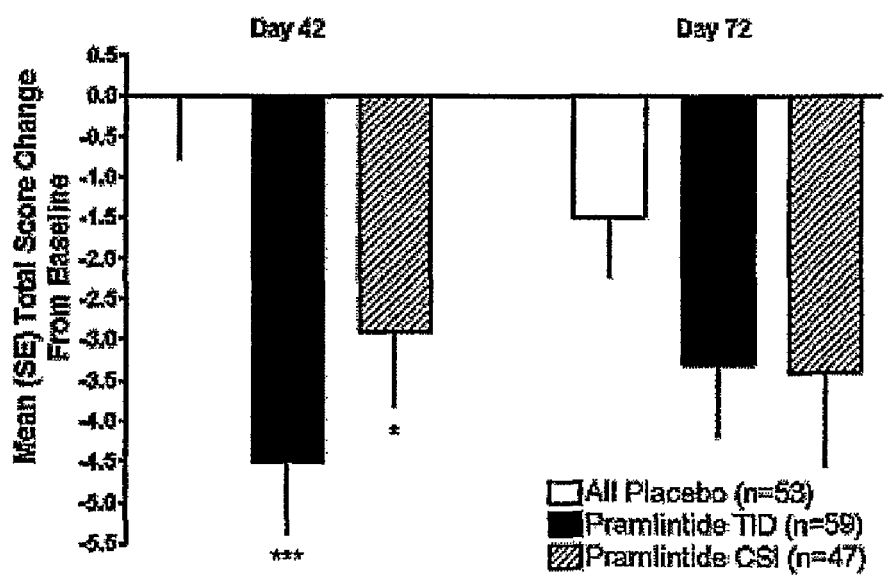
FIG. 7 is a graph depicting the binge eating scale mean total score change from baseline.

Pramlintide-treated subjects also experienced reductions in mean total BES score and a significant placebo-corrected reductions from baseline in mean BES score (−45±13%; P<0.01) as shown in FIGS. 6 and 7. There was a significant shift in binge-eating severity (P<0.05) with a greater proportion of pramlintide-treated subjects than placebo-treated subjects shifting to a lower binge-eating severity category (24.6% vs. 12.5%). After 6 weeks of TID treatment, 83.1% of pramlintide-treated subjects and 56.0% of placebo-treated subjects were categorized as mild (compared to 64.4% and 52.0%, respectively, at baseline). See Table 1 for binge eating scale severity categorization based on total score for both the TID and CSI arms of the study. Four weeks after cessation of the pramlintide treatment, the reductions from baseline in the total BES score were no longer statistically significant (FIG. 7). These results indicate that the amylin agonist provides improved control of eating behavior, in particular compulsatory aspects of eating behavior.

TABLE 1

Binge Eating Scale Severity Categorization.

| Visit<br>Total BES score | All Placebo<br>(N = 53)<br>n (%) | Pramlintide TID<br>(N = 59)<br>n (%) | Pramlintide CSI<br>(N = 47)<br>n (%) |
|---|---|---|---|
| Baseline (Day − 1) | | | |
| ≤17 (Mild) | 33 (62.3) | 38 (64.4) | 24 (51.1) |
| >17 to <27 (Moderate) | 16 (30.2) | 14 (23.7) | 16 (36.2) |
| ≥27 (Severe) | 3 (5.7) | 5 (8.5) | 6 (12.8) |
| n | 52 | 57 | 47 |
| Day 42 | | | |
| ≤17 (Mild) | 35 (66.0) | 49 (83.1) | 35 (74.5) |
| >17 to <27 (Moderate) | 13 (24.5) | 7 (11.9) | 8 (17.0) |
| ≥27 (Severe) | 4 (7.5) | 3 (5.1) | 4 (8.5) |
| n | 52 | 52 | 52 |
| Day 72 | | | |
| ≤17 (Mild) | 36 (67.9) | 45 (76.3) | 30 (63.8) |
| >17 to <27 (Moderate) | 11 (20.8) | 8 (13.6) | 7 (14.9) |
| ≥27 (Severe) | 4 (7.5) | 3 (5.1) | 4 (8.5) |
| n | 51 | 56 | 41 |

Percentages are based on the number of evaluable subjects in each treatment.

Example 5

Effect of Amylin Agonist on Anthropometric Parameters

The ability of the amylin agonist pramlintide to effect weight and anthropometric parameters, such as waist circumference and hip circumference, was examined in human subjects. In a randomized, double-blind, placebo-controlled study, changes in body weight and anthrpometric parameters, as well as indicators of glycemic control (e.g., HbAlc), serum lipids and glucose tolerance, were assessed in response to pramlintide administration to obese (BMI$\geq$30 kg/m$^2$ to $\leq$50 kg/m$^2$) non-diabetic individuals and obese individuals with non-insulin treated type 2 diabetes mellitus. The study consisted of 204 subjects, pramlintide doses of 120 μg, 180 μg, or 240 μg pramlintide TID, and study periods of a 1 week placebo lead-in period, 16 week medication period, and 8 week follow-up period with no medication.

In sum, after 16 weeks of treatment, a statistically significant, placebo-corrected mean weight loss of 3.52 kg (3.6%) of initial body weight (p<0.0001, evaluable population) was experienced, and 31% of subjects lost$\geq$5% of body weight compared with only 2% of those treated with placebo (p<0.0001, evaluable population). Weight loss was evident in both non-diabetic subjects and subjects with type 2 diabetes. Significant weight loss was achieved in subjects in all classes of obesity, with the most pronounced weight loss in subjects with class I obesity (BMI<35 kg/m$^2$). The placebo-corrected weight loss in subjects by obesity class was as follows: 4.24±0.91 kg (4.78±1.0%, p<0.0001) for those with a BMI<35 kg/m$^2$, 2.84±1.45 kg (2.63±1.39%, p<0.05) for those with a BMI$\geq$35 kg/m$^2$ to <40 kg/m$^2$, and 1.36±1.30 kg (1.29±1.09%, p<0.05) for those with a BMI$\geq$40 kg/m$^2$. The percentage of subjects achieving>5% reduction in baseline body weight by baseline BMI stratum (evaluable population N=145) is summarized in Table 2.

TABLE 2

| Baseline BMI class | Placebo (N = 48) | Pramlintide (N = 97) |
|---|---|---|
| Class I (BMI < 35 kg/m$^2$) | | |
| n | 18 | 43 |
| Percent | 0% | 39.5% |
| Class II | | |
| (BMI $\geq$ 35 kg/m$^2$ to <40 kg/m$^2$) | | |
| n | 10 | 25 |
| Percent | 0% | 28.0% |
| Class II (BMI $\geq$ 40 kg/m$^2$) | | |
| n | 20 | 29 |
| Percent | 5.0% | 20.7% |

The progressive weight loss observed in the pramlintide group was accompanied by a progressive reduction in waist circumference, a measure of abdominal obesity. Following 16 weeks of treatment, the pramlintide group had a placebo-corrected reduction in waist circumference of 2.69±1.08 cm (p<0.01), and a placebo-corrected reduction in hip circumference of 2.69±0.82 cm (p<0.01) (least squares mean±SE). Accordingly, treatment with pramlintide resulted in significant weight loss in obese individuals and significant decreases in waist and hip circumferences.

Example 6

Effect of Amylin on Body Composition

Diet-induced obesity (DIO) in the in the Sprague-Dawley rat is a valuable model for the study of obesity and regulation of energy homeostasis. In-bred DIO (Levin) Prone rats from Charles River Laboratories, Inc. (Wilmington, Mass.) (n=6/group) were used to study the effects of amylin administration. Rats were maintained ad-libitum on a moderately high fat diet (32% kcal from fat; Research Diets D1226B) for approximately 6 weeks prior to drug treatment. At the end of the fattening period they had a mean body weight of ~550 g. All rats were housed individually in shoebox cages at 22° C. in a 12/12-hour light dark cycle. Amylin was administered by subcutaneous osmotic mini-pump (Durect Corp, Calif.). Rat amylin (Peptisyntha, Torrance, Calif.) was dissolved in 50% DMSO in sterile water and infused at a rate of 100 μg/kg/d (~23 nmol/kg/d). On day 14, mini-pumps were removed and replaced with pumps containing vehicle. For body composition, rats were scanned in a specialized rodent NMR machine (Echo Medical Systems) prior to drug treatment, and at the conclusion of the experiment, which enabled the calculation of percent changes in fat and lean composition (e.g., % body fat after treatment–% body fat at baseline=change in % body fat).

Figure 8:
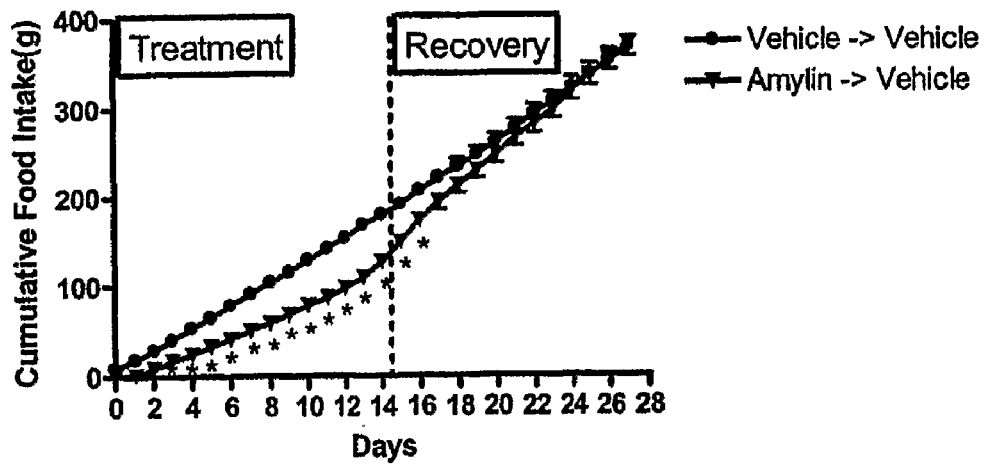
FIG. 8 is a graph depicting cumulative food intake over 28 days by DIO rats receiving either vehicle (circles) or amylin (triangles) for days 1-14 and receiving only vehicle thereafter.
Figure 9:
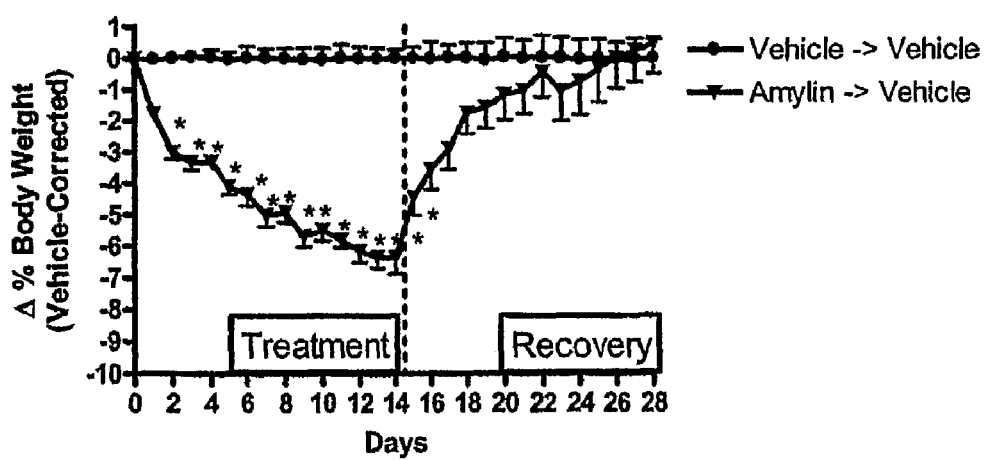
FIG. 9 is a graph depicting changes in percent body weight (vehicle-corrected) in DIO rats receiving either vehicle (circles) or amylin (triangles) for days 1-14 and receiving only vehicle thereafter.
Figure 10A:
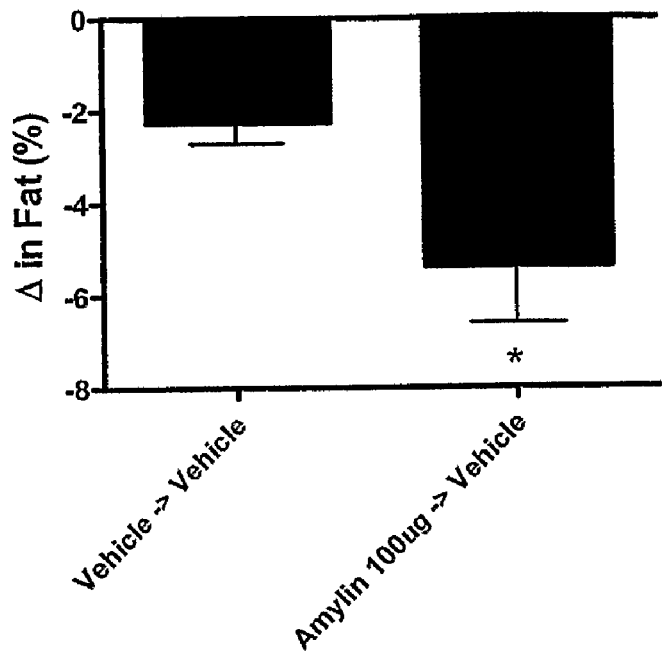
Figure 10B:
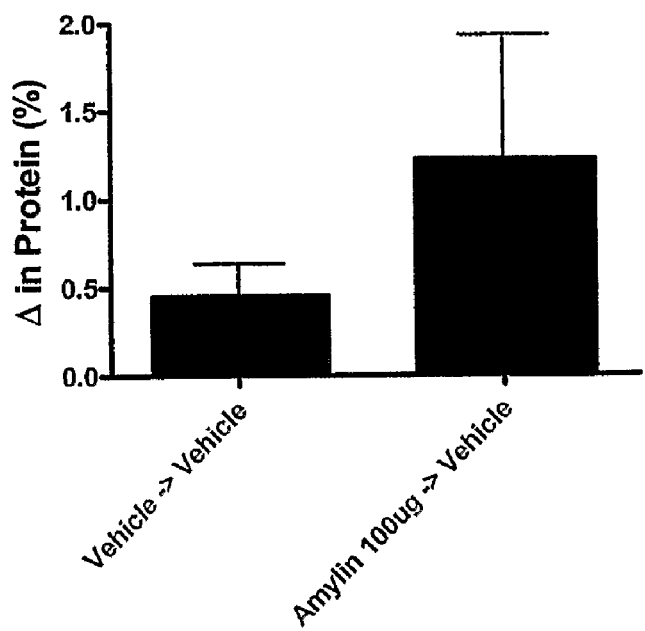

As shown in FIGS. 8 and 9, during drug treatment, amylin significantly decreased cumulative food intake and body weight (days 2-14; p<0.05 vs. vehicle controls). During washout period with the pumps containing only vehicle, food intake and body weight rapidly returned to vehicle controls levels. Analysis of body composition at the conclusion of the study revealed that despite similar body weights (on day 28), animals having been treated with amylin (days 1-14) still had a lower percent of body fat than those animals that had not received amylin (FIG. 10A). Also, animals that were treated with amylin also had a higher percent of lean body mass than those animals that had received only vehicle (FIG. 10B).

Example 7

Effect of Amylin on Food Cravings

The effect of amylin and amylin agonists on food cravings may be investigated as follows. A randomized, blinded, placebo-controlled, study design is used. Approximately 180 obese human subjects may be enrolled in the study, with one third randomized to placebo, and two thirds randomized to an amylin analog agonist, such as pramlintide. The study includes an initial one week in-patient phase to evaluate baseline food intake, meal patterns, satiety/hunger, food hedonics, food cravings, binge eating, body weight, body composition, etc. The study then transitions to a five week out-patient phase during which time body weight, body composition, and Control of Eating questionnaire may all be used to assess various parameters. The active treatment phase of the study is then concluded with a 2-3 day in-patient phase to evaluate follow-up food intake, meal patterns, satiety/hunger, food hedonics, food cravings, binge eating, body weight, body composition, etc. Generally, throughout the study, stress conditions are not induced, and lifestyle and/or diet changes or restraints are not implemented. Study endpoints to be monitored may include body weight, body composition (e.g., waist circumference, fat mass, fat-free mass), food intake, hunger/satiety, food cravings, satiating efficiency, binge eating, etc.

In such a study, it was surprisingly found that, study subjects experienced a decrease in frequency and intensity of food cravings throughout the course of administration, both via injection and infusion. It was also found that the subjects reported a reduction in the difficulty in resisting food cravings, as well as the frequency of eating in response to food cravings throughout the course of administration, both via injection and infusion. The study subjects also reported a marked reduction in cravings for sweet foods, and chocolate foods in particular throughout the course of administration, both via injection and infusion. Study subjects also reported a reduction in cravings for savory foods throughout the course of administration, both via injection and infusion, although to a lesser extent. These study results demonstrate the surprising discovery that amylin and amylin agonists modify food preferences, particularly food preferences for sweet, chocolaty, and savory foods.

Example 8

Receptor Binding Assays

Initially, polypeptides can be used in assays to determine binding ability to amylin, calcitonin and CGRP receptors. Binding assays for determining interactions with the amylin-receptor, the calcitonin-receptor, and the CGRP receptor are described for example in U.S. Pat. No. 5,264,372, the entirety of which is incorporated herein by reference.

In more detail, evaluation of the binding of compounds of the invention to amylin receptors can be carried out as follows. $^{125}$I-rat amylin (Bolton-Hunter labeled at the N-terminal lysine) is purchased from Amersham Corporation (Arlington Heights, Ill.). Unlabeled peptides are obtained from BACHEM Inc. (Torrance, Calif.) and Peninsula Laboratories (Belmont, Calif.).

Male Sprague-Dawley® rats (200-250) grams are sacrificed by decapitation. Brains are removed to cold phosphate-buffered saline (PBS). From the ventral surface, cuts are made rostral to the hypothalamus, bounded laterally by the olfactory tracts and extending at a 45 angle medially from these tracts. This basal forebrain tissue, containing the nucleus accumbens and surrounding regions, is weighed and homogenized in ice-cold 20 mM HEPES buffer (20 mM HEPES acid, pH adjusted to 7.4 with NaOH at 23° C.). Membranes are washed three times in fresh buffer by centrifugation for 15 minutes at 48,000×g. The final membrane pellet is resuspended in 20 mM HEPES buffer containing 0.2 mM phenylmethylsulfonyl fluoride (PMSF).

To measure $^{125}$I-amylin binding, membranes from 4 mg original wet weight of tissue are incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions are incubated for 60 minutes at 2C. Incubations are terminated by filtration through GF/B glass fiber filters (Whatman Inc., Clifton, N.J.) which has been pre-soaked for 4 hours in 0.3% poylethyleneimine in order to reduce nonspecific binding of radiolabeled peptides. Filters are washed immediately before filtration with 5 ml cold PBS, and immediately after filtration with 15 ml cold PBS. Filters are removed and radioactivity assessed in a gamma-counter at a counting efficiency of 77%. Competition curves are generated by measuring binding in the presence of 10-12 to $10^{-6}$ M unlabeled test compound and are analyzed by nonlinear regression using a 4-parameter logistic equation (Inplot program; GraphPAD Software, San Diego, Calif.).

In this assay, purified human amylin binds to its receptor at a measured $IC_{50}$ of about 50 pM. Results for test compounds of the invention are set forth in the Table 3 showing that each of the compounds has significant receptor binding activity.

Evaluation of the binding of compounds of the invention to CGRP receptors was essentially as described for amylin except using 125I hCGRP and membranes prepared from SK-N-MC cells, known to express CGRP receptors (Muff et. al., (1992) *Ann N Y Acad Sci.* 657:106-116). Binding assays were performed as described for amylin except using 13,500 cpm 125I-hCGRP/well or 21.7 pM/well (Amersham).

Binding to the calcitonin receptor may be investigated using CHO cells or T47D cells, which also express the calcitonin receptor (Muff et al., (1992) *Ann N Y Acad Sci.* 657: 106-116 and Kuestner et. al. (1994) *Mol. Pharmacol.* 46:246-255), as known in the art.

TABLE 3

| | $EC_{50}$ values (nM) for polypeptides | | |
|---|---|---|---|
| Compound | Amylin | Calcitonin | CGRP |
| 1 (3236) | 0.028 | 0.029 | 2.342 |
| 2 (3235) | 0.047 | 0.052 | 33.988 |
| 3 (3150) | 0.023 | 0.020 | 0.490 |
| 4 (164161) | 0.035 | 0.019 | 8.500 |
| 5 (164163) | 0.022 | 0.018 | 2.600 |
| 6 (1166) | 0.030 | nt | nt |
| 7 (2749) | 0.057 | nt | 7.540 |
| 8 (3318) | 8.070 | 0.478 | 175.665 |
| 9 (164370) | 0.043 | 0.014 | 1.600 | nt denotes not tested

Example 9

Activity of Polypeptides on Food Intake

Female NIH/Swiss mice (8-14 weeks old) were group housed with a 12:12 hour light:dark cycle. Water and a standard pelleted mouse chow diet are available ad libitum, except as noted. Animals are fasted starting at approximately 1500 hrs, 1 day prior to experiment.

At time=0 min, all animals are given an intraperitoneal injection of vehicle or polypeptide in a volume of 200 uL/mouse and immediately given a pre-weighed amount (10-15 g) of the standard chow. Food is removed and weighed at 30, 60, 120 and 180 minutes to determine the amount of food consumed. The effects of treatment on food intake are expressed as % change relative to control.

Figure 11:
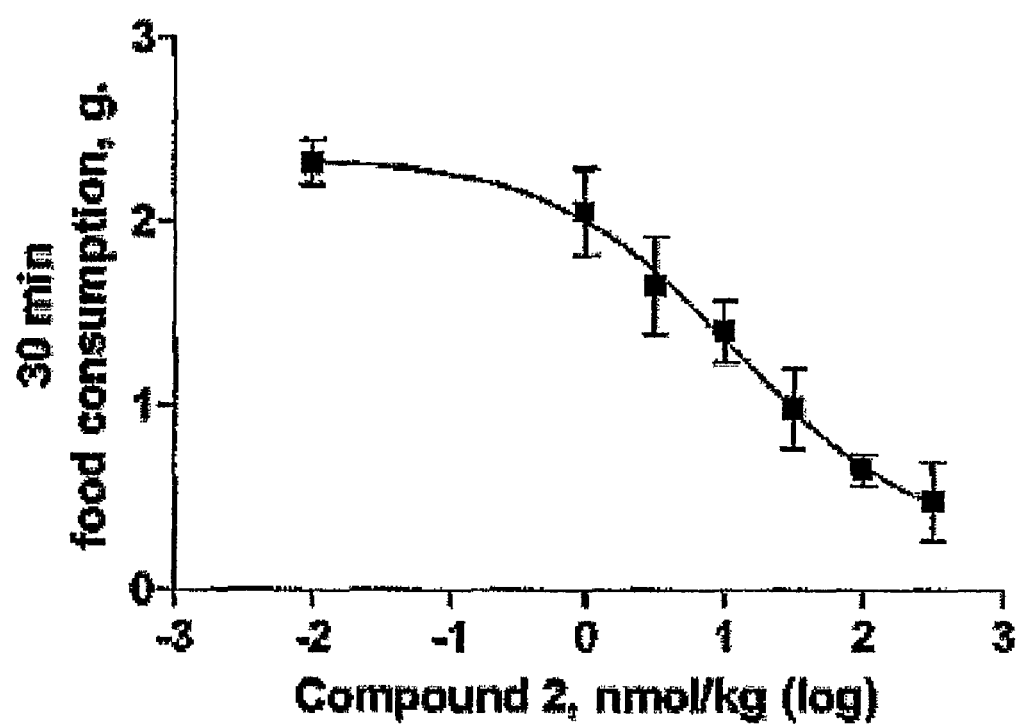
FIG. 11 is a graph depicting a dose-dependent reduction in food consumption in over night fasted mice to doses of an exemplary compound, compound 2.

As shown in FIG. 11, Compound 2, at doses from 25-300 nmol/kg, dose-dependently reduced food intake at 30 minutes post injection. Table 4 depicts reduced food intake with polypeptides administered peripherally (intraperitoneal injection) at doses 25 nmol/kg. The data at time points 30, 60, 120, and 180 minutes represents the percent decrease in cumulative food intake compared to the vehicle.

TABLE 4

| | Cumulative Food Intake | | | |
|---|---|---|---|---|
| Compound | 30 min | 60 min | 120 min | 180 min |
| 1 (3236) | −58 | −46 | −33 | −22 |
| 2 (3235) | −58 | −54 | −52 | nt |
| 3 (3150) | −58 | −52 | −37 | −33 |
| 4 (164161) | −42 | −31 | −35 | −30 |
| 5 (164163) | −66 | −53 | −29 | −27 |
| 6 (1166) | −48 | −45 | −23 | nt |
| 7 (2749) | −60 | −52 | −23 | nt |
| 8 (3318) | −6 | −15 | −25 | −28 |

TABLE 4-continued

Cumulative Food Intake

| Compound | 30 min | 60 min | 120 min | 180 min |
|---|---|---|---|---|
| 9 (164370) | −80 | −64 | −43 | nt |
| 10 (999) | −19 | −20 | −35 | nt |
| 11 (164161) | −52 | −47 | −38 | −35 |
| 12 (164162) | −43 | −39 | −37 | −32 |
| 13 (164164) | −40 | −33 | −25 | −24 |
| 14 (164166) | −52 | −36 | −28 | −33 |
| 15 (164174) | −67 | −59 | −37 | −30 |
| 16 (164175) | −26 | −29 | −30 | −27 |
| 17 (164176) | −42 | −30 | −30 | −25 |
| 18 (164177) | −2 | −7 | −16 | −21 |
| 19 (167178) | −25 | −25 | −35 | −31 |
| 20 (164179) | −9 | −21 | −30 | −31 |
| 21 (164188) | 9 | −5 | −18 | −18 |
| 22 (164189) | −11 | −20 | −31 | −30 |
| 23 (164190) | 8 | 0 | −19 | −12 |
| 24 (164191) | −40 | −34 | −35 | −35 |
| 25 (164205) | −29 | −34 | −45 | nt |
| 26 (164283) | −29 | −36 | −47 | nt |
| 27 (164284) | −12 | −11 | −32 | nt |
| 28 (164285) | −8 | −16 | −28 | nt |
| 29 (164286) | 4 | −1 | −25 | nt |
| 30 (164287) | −1 | −2 | −19 | nt |
| 31 (164289) | −11 | −18 | −23 | nt |
| 32 (164289) | −15 | −21 | −31 | nt |
| 33 (164290) | −7 | −10 | −15 | nt |
| 34 (164291) | −11 | −6 | −16 | nt |
| 35 (164307) | −20 | −16 | −18 | nt |
| 36 (164308) | −34 | −22 | −24 | −25 |
| 37 (164309) | −3 | −2 | −16 | nt |
| 38 (164331) | −24 | −13 | −8 | nt |
| 39 (164346) | 7 | −14 | −23 | nt |
| 40 (164352) | −11 | −5 | −2 | nt |
| 41 (164353) | −4 | −9 | −12 | nt |
| 42 (164354) | −11 | −18 | −32 | nt |
| 43 (164355) | −4 | −7 | −18 | nt |
| 44 (164356) | −6 | −13 | −25 | nt |
| 45 (164366) | −13 | −7 | −3 | nt |
| 46 (164368) | −6 | −11 | −16 | nt |
| 47 (164369) | −5 | −13 | −27 | nt |
| 48 (164371) | −54 | −51 | −36 | nt |
| 49 (164393) | −33 | −26 | −25 | nt |
| 50 (164394) | −70 | −62 | −48 | nt |
| 51 (164395) | −44 | −39 | −35 | nt |
| 52 (164396) | −29 | −24 | −23 | nt |
| 53 (164397) | −92 | −89 | −36 | nt |
| 54 (164410) | 1 | −4 | −10 | nt |
| 55 (164411) | 9 | −5 | −12 | nt |
| 56 (164412) | 4 | −13 | −16 | nt |
| 57 (164427) | −18 | −24 | −23 | nt |
| 58 (164428) | −62 | −51 | −29 | nt |
| 59 (164429) | −81 | −77 | −50 | nt |
| 60 (164430) | −43 | −40 | −26 | nt |
| 61 (164468) | −23 | −27 | −32 | nt |
| 62 (164469) | −14 | −22 | −38 | nt |
| 63 (164482) | −19 | −22 | −28 | nt |
| 64 (164486) | −65 | −58 | −44 | nt |
| 65 (164491) | −33 | −29 | −32 | nt |
| 66 (164493) | −13 | −15 | −28 | nt |
| 67 (164494) | −10 | −11 | −12 | nt |
| 68 (164496) | −10 | −13 | −21 | nt |
| 69 (164497) | −29 | −31 | −45 | nt |
| 70 (164523) | −76 | −64 | −47 | nt |
| 71 (164531) | −7 | −13 | −22 | −18 |
| 72 (164532) | 0 | −8 | −13 | −19 |
| 73 (164533) | −51 | −31 | −23 | −28 |
| 74 (164552) | −42 | −32 | −31 | nt |
| 75 (164563) | −60 | −52 | −38 | nt |
| 76 (164569) | −25 | −29 | −40 | nt |
| 77 (164570) | −46 | −43 | −44 | nt |
| 78 (164571) | −57 | −44 | −44 | nt |
| 79 (164586) | −49 | −40 | −33 | nt |
| 80 (164587) | −32 | −28 | −22 | nt |
| 81 (164590) | −28 | −24 | −33 | nt |
| 82 (164594) | −7 | −13 | −16 | −19 |
| 83 (164595) | −7 | −13 | −22 | −12 |
| 84 (164644) | −53 | −40 | −20 | nt |
| 85 (164645) | 3 | −16 | −16 | nt |
| 86 (164646) | −44 | −26 | −16 | nt |
| 87 (164647) | −43 | −32 | −21 | nt |
| 88 (164648) | −64 | −61 | −39 | −22 |
| 89 (164666) | −6 | −13 | −22 | −20 |
| 90 (164671) | −55 | −41 | −24 | −15 |
| 91 (164689) | −59 | −47 | −26 | −24 |
| 92 (164690) | −31 | −29 | −30 | −27 |
| 93 (164698) | −43 | −30 | −27 | −29 |
| 94 (164704) | −62 | −42 | −36 | −31 |
| 95 (164705) | −81 | −69 | −34 | −31 |
| 96 (164706) | −49 | −38 | −19 | −23 |
| 97 (164713) | −78 | −76 | −60 | −40 |
| 98 (164721) | −18 | −13 | −5 | −1 |
| 99 (164726) | −57 | −55 | −50 | nt |
| 100 (164727) | −60 | −52 | −41 | nt |
| 101 (164728) | −52 | −48 | −35 | nt |
| 102 (164731) | −58 | −53 | −45 | nt |
| 103 (164739) | −50 | −44 | −30 | nt |
| 104 (164772) | −69 | −67 | −54 | nt |
| 105 (164773) | −83 | −82 | −52 | nt |
| 106 (164774) | −58 | −54 | −39 | nt |
| 107 (164776) | −84 | −78 | −47 | nt |
| 108 (164777) | −70 | −66 | −38 | nt |
| 109 (164778) | −61 | −54 | −43 | nt |
| 110 (164779) | −80 | −72 | −59 | nt |
| 111 (164780) | −39 | −37 | −32 | nt |
| 112 (164781) | −62 | −65 | −50 | nt |
| 113 (164792) | −79 | −86 | −55 | nt |
| 114 (164793) | −17 | −20 | −25 | nt |
| 115 (2604) | 6 | −3 | −25 | −25 |
| 116 (2621) | 5 | 5 | 3 | nt |
| 117 (2725) | −13 | −11 | −3 | nt |
| 118 (2744) | −4 | 0 | 13 | nt |
| 119 (3234) | 6 | −8 | −11 | nt |
| 120 (3319) | −3 | 1 | −6 | −7 |
| 121 (3358) | 5 | 2 | −1 | 3 |
| 122 (3536) | −6 | −12 | −23 | −21 |
| 123 (3894) | 1 | −13 | −17 | −13 |
| 124 (3909) | 4 | −4 | −15 | −16 |
| 125 (3981) | 10 | −1 | −6 | nt |
| 126 (4000) | 5 | −10 | −20 | nt |
| 127 (4027) | −5 | −14 | −12 | −12 | nt = not done

Example 10

Activity of Compounds of the Invention on Weight Reduction and Caloric Intake

Figure 12A:
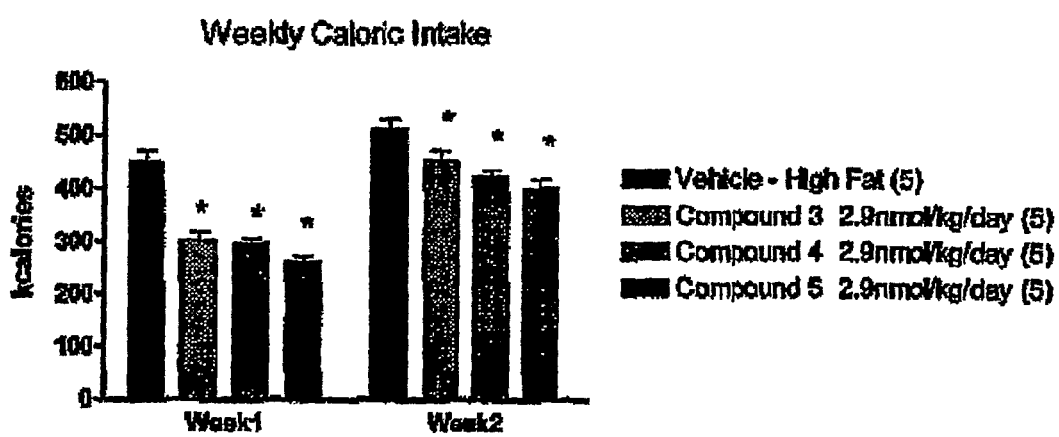
FIGS. 12A and 12 B are graphs depicting the effects of amylin agonists on caloric intake (FIG. 12A) and body weight (FIG. 12B) in diet-induced obese (DIO) rats.
Figure 12B:
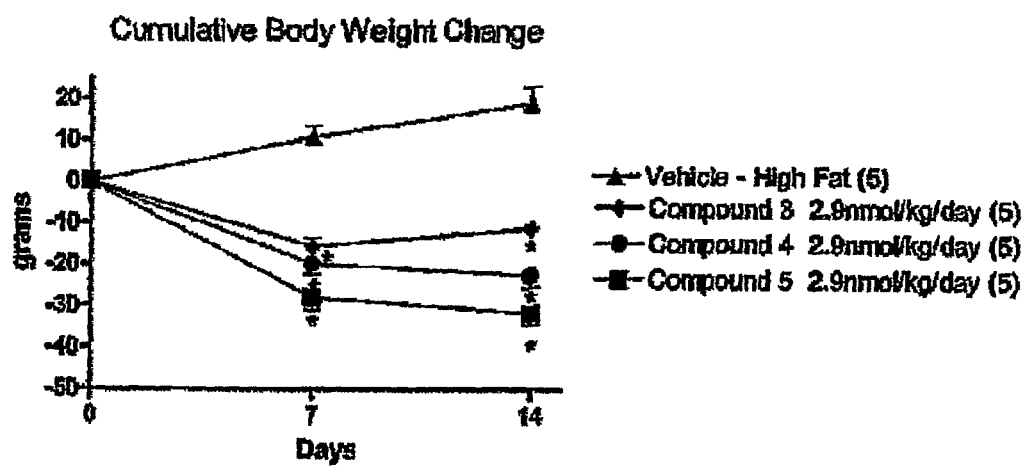

Individually housed male Sprague-Dawley® rats (350 g; 12-h light/dark cycle) were maintained on a high fat diet (58% kcal from fat) for 4 weeks. At the end of fattening period, 14-day osmotic pumps (Durect Corp.) were implanted interscapularly under anesthesia. Rats received pumps continuously delivering vehicle (50% DMSO) or polypeptide at a dose of 2.9 mmol/kg/day. Food intake and body weight measurements were obtained weekly. FIGS. 12A and 12B show that the polypeptides Compound 3, Compound 4, or Compound 5 produced a decrease in caloric intake and body weight gain, respectively, throughout the 14-day test period (*P<0.05 compared to respective vehicle-high fat group). Table 5 presents the percent body weight loss at week 1 and 2 for several compounds.

TABLE 5

Body weight loss after administration of exemplary compounds of the invention

| Compound | Week 1 | Week 2 |
| --- | --- | --- |
| 1 (3236) | 8.3* | 10.5* |
| 2 (3235) | 9.8* | 9.4* |
| 3 (3150) | 5.9* | 6.7* |
| 4 (164161) | 6.8* | 9.2* |
| 5 (164163) | 8.6* | 11.3* |
| 6 (1166) | 2.9* | 3.8* |
| 7 (2749) | 10.0* | 11.4* |
| 8 (3318) | 2.3 | 2.5 |
| 9 (164370) | 4.9* | 4.9* |

*P < 0.05 compared to controls

Example 11

Body Composition

Figure 13:
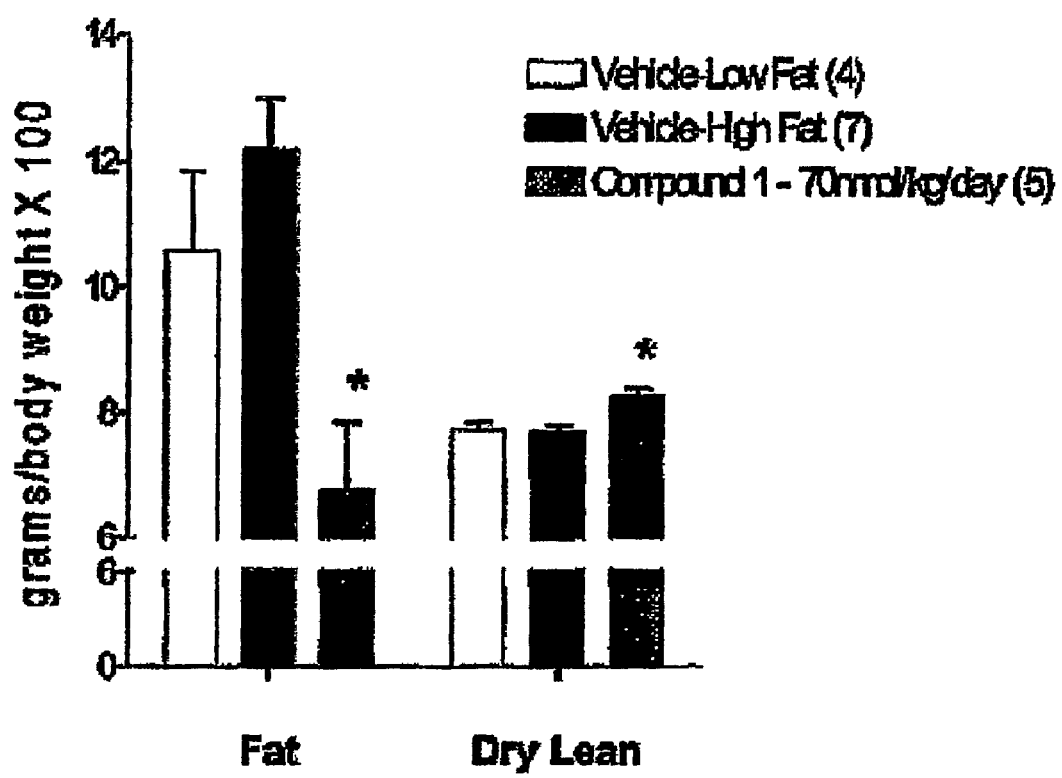
FIG. 13 is a graph depicting effects on body composition by an exemplary compound.

Individually housed male Sprague-Dawley® rats (420 g; 12-h light/dark cycle) were maintained on a high fat diet (58% kcal from fat) for 4 weeks. At the end of fattening period, 14-day osmotic pumps (Durect Corp.) were implanted interscapularly under anesthesia. Rats received pumps that continuously delivered vehicle (50% DMSO) or Compound 1 at a dose of 70 nmol/kg/day. Animals were sacrificed on Day 12. Carcasses were immediately frozen and body composition (fat and protein) measured by chemical analysis (Covance Laboratories, Madison, Wis.). FIG. 13 shows that, as a percent of total body mass, fat content was reduced in rats treated with Compound 1 compared to controls. In addition, Compound 1 increased the percent of lean mass content.

Example 12

Gastric Emptying and Ion Calcium

Gastric emptying was monitored by measuring the appearance in plasma of gavaged tritiated glucose. Subjects were conscious, male Sprague Dawley® rats (7-9 weeks of age, 12:12 h light:dark cycle) with ad libitum access to food and water until the start of the experiment. Prior to dosing, food and water were removed. At t=−5 min, peptide or vehicle (200 μl saline) was administered subcutaneously. At t=0 min, a solution of 1 ml sterile water containing 5 μCi D-[3-3H] glucose (Dupont, Wilmington, Del.) was given by oropharyngeal tube. At t=20 min, topical anesthetic (Hurricaine®, 20% benzocaine liquid) was applied to the tip of the tail. At t=40 min, the tip of the tail was ligated with a scalpel and ~250 μl blood was collected into heparinized tubes. Plasma was then immediately assayed for ionized calcium using a Ciba/Corning 634 Ca/pH analyzer (Ciba/Corning, Inc., Medfield, Mass.). A 10 μl plasma sample was pipetted into prepared scintillation vials (0.5 ml water+2 ml scintillation cocktail (Ecolite scintillation cocktail ICN, Costa Mesa, Calif.)), vortexed and counted in a β-counter (1209 Rack-beta; LKB-Wallac, Gaithersburg, Md.) for 1 minute/vial.

Figure 14A:
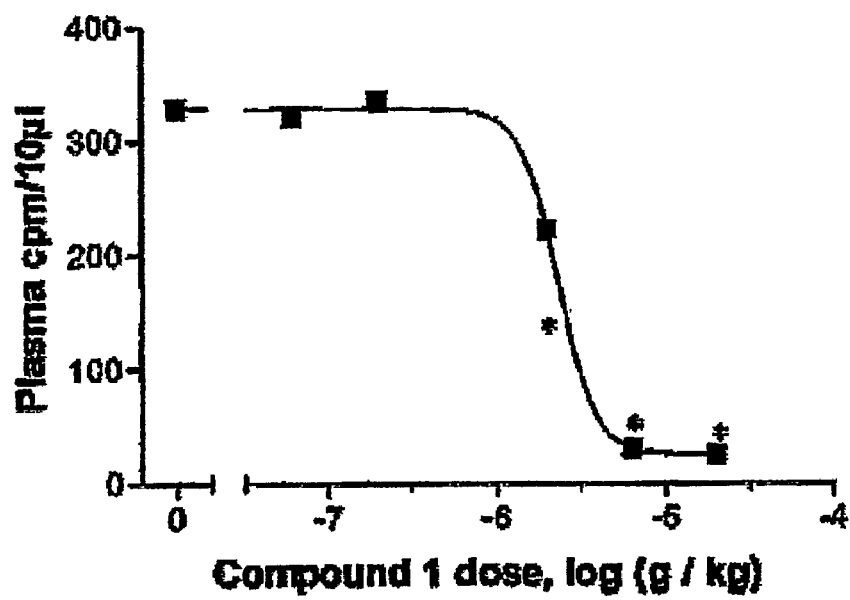
FIGS. 14 A and 14B are graphs depicting of an exemplary compound (compound 1) on gastric emptying (FIG. 14A) and on hypocalcemia (FIG. 14B).

In FIG. 14A, points represent mean±sd of 6 rats (fed, conscious). The indicated dose of peptide was injected subcutaneously at t=0. Blood was collected 35 minutes later for cpm analysis. *All points p<0.001 vs. saline control; ANOVA, Dunnett's test. From non-linear regression: $ED_{50}$=2.3 μg/kg. Bottom=25 cpm/10 μl; Top=328 cpm/10 μl. Maximum decrease in plasma cpm: −92%. Goodness of fit: $r^2$=0.9992.

Figure 14B:
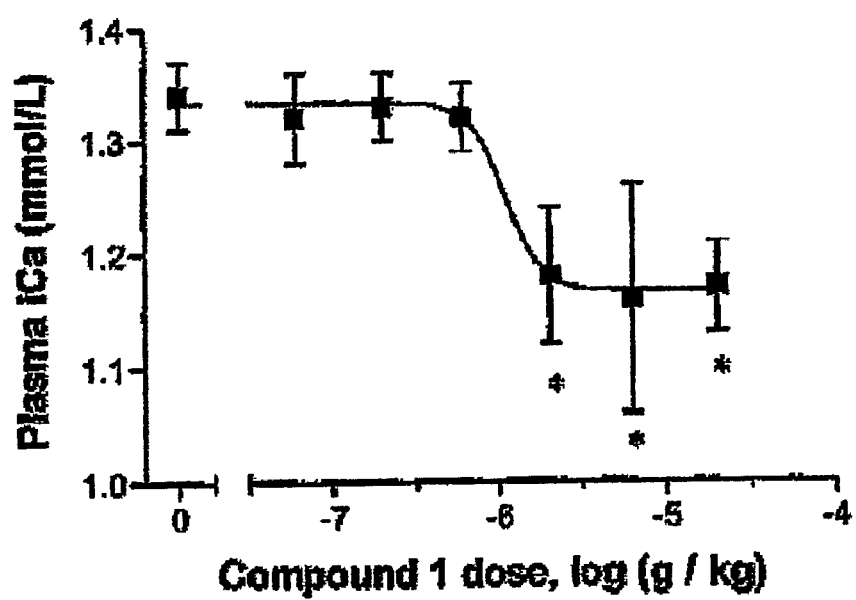

In FIG. 14B, points represent mean±sd of 6 rats (fed, conscious). The indicated dose of peptide was injected subcutaneously at t=0. Blood was collected 35 minutes later for cpm analysis. *P<0.001 vs. saline control; ANOVA, Dunnett's test. From non-linear regression: ED50=1.1 μg/kg. Bottom=1.2 mmol/L; Top=1.3 mmol/L. Maximum decrease in plasma iCa: −14% Goodness of fit: $r^2$=0.9936.

Example 13

Combination Therapy: Amylin+Sibutramine

In-bred DIO prone rats were obtained from Charles Rivers Labs. These rats were developed from a line of Crl:CD® (SD)BR rats that are prone to become obese on a diet relatively high in fat and energy (Levin, 1997). The rats were housed individually in shoebox cages at 22° C. in a 12/12-hour light dark cycle. Rats were maintained ad-libitum on a moderately high fat diet (32% kcal from fat; Research Diets D1226B) for 6 weeks prior to drug treatment. At the end of the fattening period they typically have a mean body weight of 500 g. Rats were then divided into treatment groups and implanted with two subcutaneous mini-pumps (Durect Corp). One pump contained either vehicle (50% DMSO in water) or amylin (100 μg/kg/day) while the other pump contained either sterile water or sibutramine (3 mg/kg/day).

Figure 15:
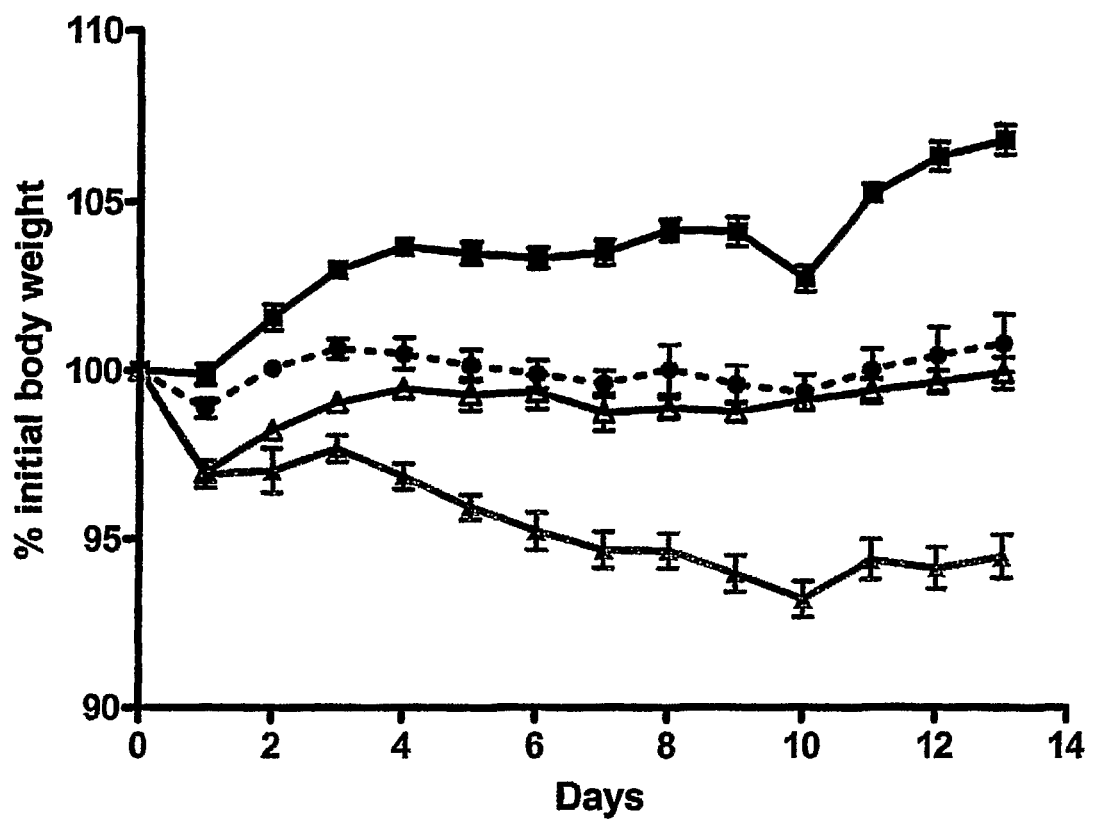
FIG. 15 is a graph depicting the effect of amylin, either alone or in combination with sibutramine, on body weight in DIO rats. Solid squares represent vehicle, solid circles represent sibutramine alone, open triangles represent amylin alone, and solid triangles represent the combination of amylin and sibutramine.
Figure 16A:
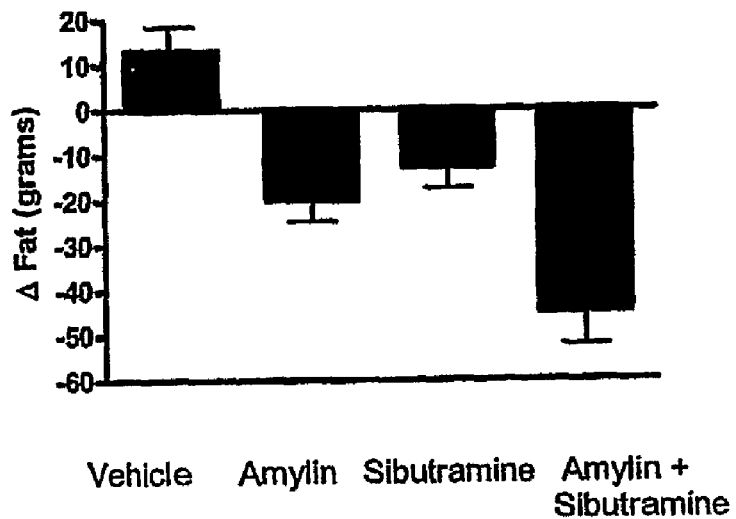
FIGS. 16A and 16B are graphs depicting effects on body weight of administration of sibutramine (3 mg/kg/day) and amylin (100 µg/kg/day), either alone or in combination over two weeks.
Figure 16B:
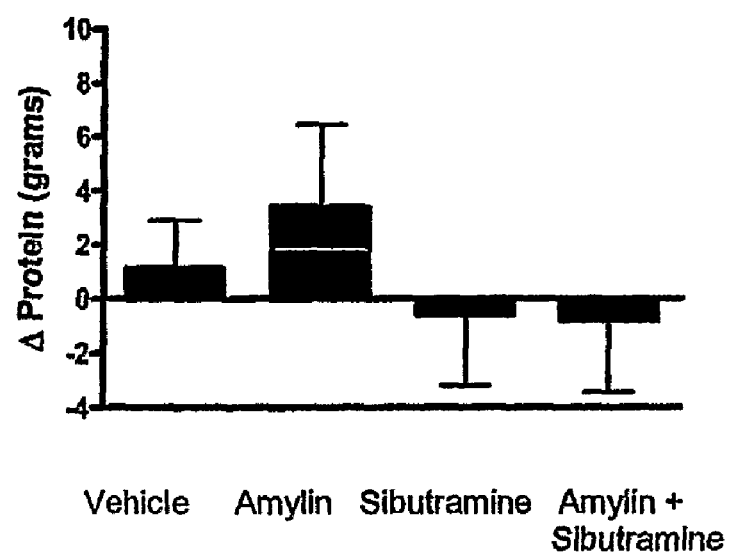

As shown in FIG. 15, an approximately 5% change in body weight (vehicle-corrected) was observed with the either amylin alone or sibutramine alone, while the combination of Amylin and sibutramine yielded approximately a 12% change in body weight (vehicle-corrected). Fat mass loss was also evident with the treatment of either amylin alone or sibutramine alone, and a synergistic effect was obtained when both amylin and sibutramine were administered in combination (FIG. 16A). When amylin was administered alone, lean (protein) mass was increased, while lean (protein) mass was relatively unchanged when sibutramine was administered alone or in combination with amylin (FIG. 16B).

Example 14

Combination Therapy: Amylin+CB-1 Antagonist

Figure 17:
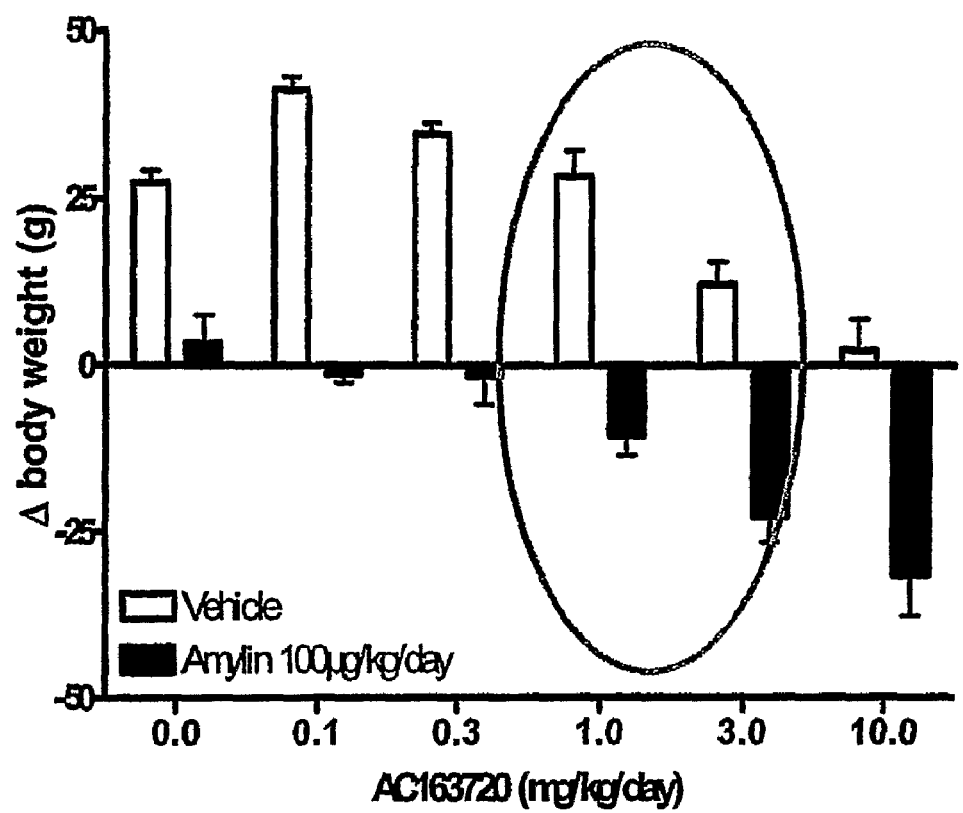
FIG. 17 is a graph depicting the effect of administration of a range of doses of a CB-1 antagonist, either alone or in combination with amylin (100 µg/kg/day), on body weight. The time course of the combinations in the circled area are depicted in FIGS. 18A and 18B.
Figure 18A:
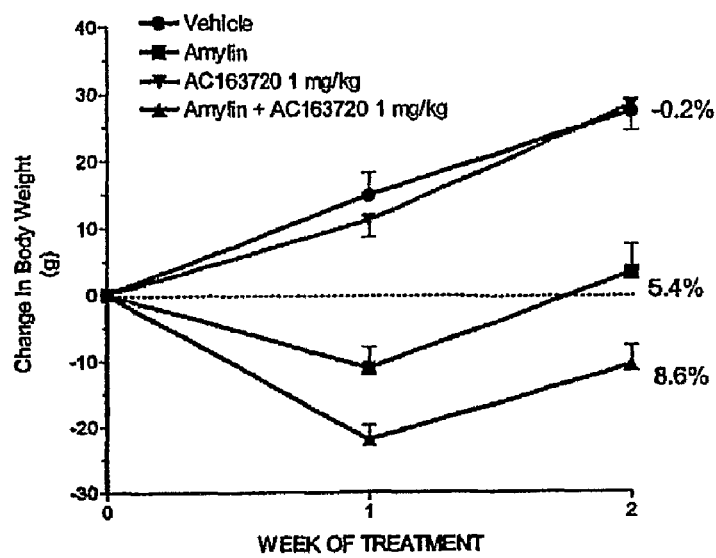
FIGS. 18A and 18B are graphs depicting the effect of administration of a CB-1 antagonist and amylin, either alone or in combination, on body weight.
Figure 18B:
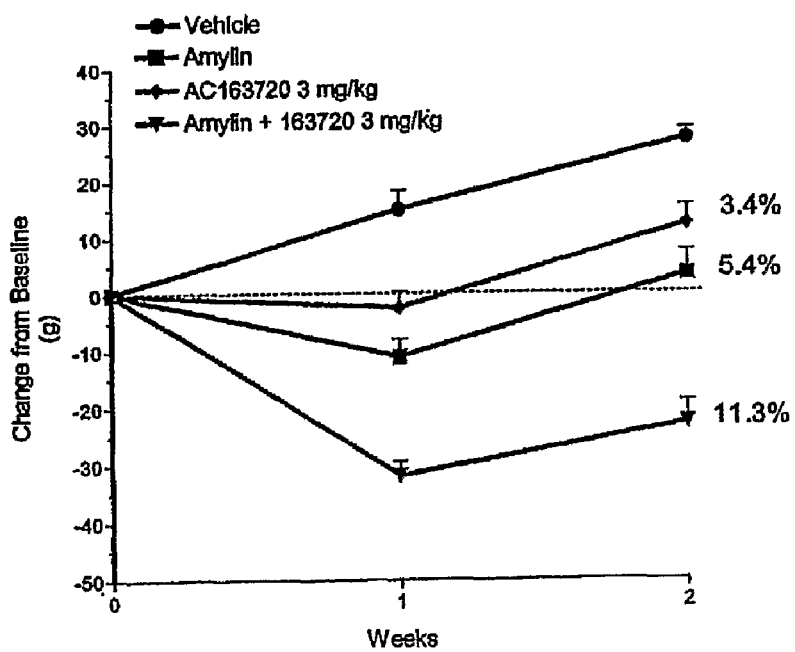

DIO prone rates (obtained from Charles Rives Labs) were housed individually in shoebox cages at 22° C. in a 12/12-hour light dark cycle. Rats were maintained ad-libitum on a moderately high fat diet (32% kcal from fat; Research Diets D1226B) for 6 weeks prior to drug treatment. At the end of the fattening period they typically have a mean body weight of 500 g. Rats were then divided into treatment groups and implanted with one subcutaneous mini-pump (Durect Corp) and inserted with an oral gavage. The mini-pump contained either vehicle (50% DMSO in water) or amylin (100 μg/kg/day) while the oral gavage administered either sterile water or a range of doses of a CB-1 antagonist (0.1, 0.3, 1.0, 3.0, 10.0 mg/kg/day). Change in body weight after 2 weeks is depicted in FIG. 17 and two of these combinations (circled) are highlighted in FIGS. 18A and 18B in more detail.

While the foregoing description discloses the present invention, with examples provided for the purpose of illustration, it will be understood that the practice of the present invention encompasses all of the usual variations, adaptations, or modifications as being within the scope of the claimed invention. Therefore, descriptions and examples should not be construed as limiting the scope of the invention.

What is claimed is:

1. A method of controlling binge eating in a human in need thereof comprising administering an effective amount of pramlintide to the human to control binge eating.

2. The method of claim 1, wherein the effective amount is 25 μg to 240 μg.

3. The method of claim 1, wherein pramlintide is in the form of a salt.

4. A method of controlling binge eating in a subject in need thereof comprising administering an effective amount of an amylin agonist to the subject to control binge eating.

5. The method of claim 4, wherein the amylin agonist is administered to the subject in an amount effective to reduce the subject's Binge Eating Scale total score as compared to the Binge Eating Scale total score in the absence of administration of the amylin agonist.

6. The method of claim 4, wherein the amylin agonist is administered to the subject in an amount effective to alter the subject's Binge Eating Scale category as compared to the Binge Eating Scale category in the absence of administration of the amylin agonist; wherein the Binge Eating Scale category is altered from severe to moderate, from severe to mild, or from moderate to mild.

7. The method of claim 4, wherein the amylin agonist is administered at one or more times of the day when the subject is most likely to binge eat.

8. The method of claim 4, wherein the subject binge eats when emotionally distressed.

9. The method of claim 4, wherein the subject has an anxiety disorder.

10. The method of claim 4, wherein the amylin agonist is a peptide comprising the amino acid sequence of any one of SEQ ID NOs:4-31.

11. The method of claim 4, where the amylin agonist is pramlintide.

12. The method of claim 4, wherein the effective amount is 25 μg to 240 μg.

13. The method of claim 4, wherein the amylin agonist is in the form of a salt.

14. The method of claim 4, wherein the subject is human.

15. The method of claim 4, further comprising administering an effect amount of a PYY, a PYY agonist, a GLP-1, a GLP-1 agonist, a DPPIV inhibitor, a CCK, a CCK agonist, an exendin, an exendin agonist, a GIP, a GIP agonist, leptin, or a leptin agonist.

16. A method of controlling binge eating in a human in need thereof comprising administering an effective amount of a peptide comprising the amino acid sequence of SEQ ID NO:3 to the human to control binge eating.

17. The method of claim 16, wherein the peptide comprises the amino acid sequence of any one of SEQ ID NOs:4-31.

18. The method of claim 16 wherein the peptide comprises the amino acid sequence of any one of SEQ ID NOs:4-9.

19. The method of claim 16, wherein the peptide comprises the amino acid sequence of SEQ ID NO:6.

20. The method of claim 16, wherein the peptide is in the form of a salt.

* * * * *